(12) United States Patent
Baker, Jr. et al.

(10) Patent No.: US 12,076,397 B2
(45) Date of Patent: Sep. 3, 2024

(54) EMULSION ADJUVANT FOR INTRAMUSCULAR, INTRADERMAL AND SUBCUTANEOUS ADMINISTRATION

(71) Applicants: The Regents of the University of Michigan, Ann Arbor, MI (US); NanoBio Corporation, Ann Arbor, MI (US)

(72) Inventors: James R. Baker, Jr., Ann Arbor, MI (US); Douglas M. Smith, Ann Arbor, MI (US); Susan Ciotti, Ann Arbor, MI (US)

(73) Assignees: THE REGENTS OF THE UNIVERSITY OF MICHIGAN, Ann Arbor, MI (US); BLUEWILLOW BIOLOGICS, INC., Ann Arbor, MI (US)

( * ) Notice: Subject to any disclaimer, the term of this patent is extended or adjusted under 35 U.S.C. 154(b) by 0 days.

(21) Appl. No.: 16/300,423

(22) PCT Filed: May 10, 2017

(86) PCT No.: PCT/US2017/031958
§ 371 (c)(1),
(2) Date: Nov. 9, 2018

(87) PCT Pub. No.: WO2017/196979
PCT Pub. Date: Nov. 16, 2017

(65) Prior Publication Data
US 2020/0405846 A1    Dec. 31, 2020

Related U.S. Application Data

(60) Provisional application No. 62/334,267, filed on May 10, 2016.

(51) Int. Cl.
| | |
|---|---|
| *A61K 39/395* | (2006.01) |
| *A61K 9/00* | (2006.01) |
| *A61K 9/107* | (2006.01) |
| *A61K 38/38* | (2006.01) |
| *A61K 39/12* | (2006.01) |
| *A61K 39/145* | (2006.01) |
| *A61K 39/39* | (2006.01) |
| *A61K 47/10* | (2017.01) |
| *A61K 47/18* | (2017.01) |
| *A61K 47/26* | (2006.01) |
| *A61K 47/34* | (2017.01) |
| *A61K 39/00* | (2006.01) |

(52) U.S. Cl.
CPC ............ *A61K 39/39* (2013.01); *A61K 9/0019* (2013.01); *A61K 9/0043* (2013.01); *A61K 9/107* (2013.01); *A61K 38/38* (2013.01); *A61K 39/12* (2013.01); *A61K 39/145* (2013.01); *A61K 47/10* (2013.01); *A61K 47/186* (2013.01); *A61K 47/26* (2013.01); *A61K 47/34* (2013.01); *A61K 2039/54* (2013.01); *A61K 2039/55566* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,675,189 A | 6/1987 | Kent et al. |
| 4,895,452 A | 1/1990 | Yiournas |
| 5,075,109 A | 12/1991 | Tice et al. |
| 5,103,497 A | 4/1992 | Hicks |
| 5,133,974 A | 7/1992 | Paradissis et al. |

(Continued)

FOREIGN PATENT DOCUMENTS

| | | |
|---|---|---|
| KR | 2007/0109411 | 11/2007 |
| WO | WO 1997/48440 | 12/1997 |

(Continued)

OTHER PUBLICATIONS

Lincopan et al, Vaccine, 2007, vol. 27, p. 5760-5771.*

(Continued)

*Primary Examiner* — Yunsoo Kim

(74) *Attorney, Agent, or Firm* — Casimir Jones SC; Tyler Sisk

(57) ABSTRACT

The present invention provides compositions comprising emulsion adjuvant and one or more active agents or substances formulated for infusion or injection into a subject (e.g., using a syringe and needle), as well as methods of formulating and using the same (e.g., as an injectable medicinal composition (e.g., a vaccine)). The emulsion adjuvant of an immunogenic composition of the invention in its preferred form comprises a cationic lipid containing a polar head group and a hydrophobic component (e.g., a dual chain hydrophobic group (e.g., the cationic surfactant dioctadecyl dimethyl ammonium chloride (DODAC) and dioctadecyl dimethyl ammonium bromine (DODAB))). Compositions of the invention comprising emulsion adjuvant and one or more active agents or substances formulated for administration via injection to a subject find use in treatment and/or prevention of infectious disease, cancer and/or allergy.

6 Claims, 34 Drawing Sheets

(56) References Cited

U.S. PATENT DOCUMENTS

| | | | |
|---|---|---|---|
| 5,407,686 A | 4/1995 | Patel et al. | |
| 5,510,104 A | 4/1996 | Allen | |
| 5,736,152 A | 4/1998 | Dunn | |
| 5,993,412 A | 11/1999 | Deily et al. | |
| 6,015,832 A | 1/2000 | Baker, Jr. et al. | |
| 6,506,803 B1 | 1/2003 | Baker, Jr. et al. | |
| 6,559,189 B2 | 5/2003 | Baker, Jr. et al. | |
| 6,635,676 B2 | 5/2003 | Baker, Jr. et al. | |
| 8,232,320 B2* | 7/2012 | Baker, Jr. ............ | A61K 45/06 514/642 |
| 2002/0045667 A1 | 4/2002 | Baker, Jr. et al. | |
| 2003/0194412 A1 | 10/2003 | Baker et al. | |
| 2004/0043041 A1 | 3/2004 | Baker, Jr. et al. | |
| 2005/0208083 A1 | 9/2005 | Annis | |
| 2005/0220814 A1 | 10/2005 | Dominowski et al. | |
| 2005/0281843 A1 | 12/2005 | Singh et al. | |
| 2006/0083780 A1* | 4/2006 | Heyes ............ | A61P 31/00 435/458 |
| 2006/0251684 A1 | 11/2006 | Annis et al. | |
| 2007/0036831 A1 | 2/2007 | Baker | |
| 2010/0016381 A1 | 1/2010 | Asakawa et al. | |

FOREIGN PATENT DOCUMENTS

| | | |
|---|---|---|
| WO | WO 1998/20734 | 5/1998 |
| WO | WO 1998/28037 | 7/1998 |
| WO | WO 1999/27961 | 6/1999 |
| WO | WO 2005/060330 A2 | 7/2005 |
| WO | WO 2012/006380 A2 | 1/2012 |
| WO | WO 2015/143386 | 9/2015 |
| WO | WO 2016/046357 | 3/2016 |
| WO | WO 2017/201390 A1 | 11/2017 |

OTHER PUBLICATIONS

Allen, T, et al. Liposomal drug delivery systems: from concept to clinical applications. Adv Drug Deliv Rev. Jan. 2013;65(1):36-48.
Audibert, F. M. et al. Adjuvants: current status, clinical perspectives and future prospects. Immunol Today. Jun. 1993;14(6):281-4.
Bazin, H., et al., Predominant contribution of IgA antibody-forming cells to an immune response detected in extraintestinal lymphoid tissues of germ-free mice exposed to antigen by the oral route. J Immunol. Oct. 1970;105(4):1049-51.
Cox et al., A fast track influenza virus vaccine produced in insect cells. J Invertebr Pathol. Jul. 2011;107 Suppl:S31-41.
Crabbe, P. A., et al., Antibodies of the IgA type in intestinal plasma cells of germfree mice after oral or parenteral immunization with ferritin. J Exp Med. Oct. 1, 1969;130(4):723-44.
Craig, S. W., et al., Peyer's patches: an enriched source of precursors for IgA-producing immunocytes in the rabbit. J Exp Med. Jul. 1, 1971;134(1):188-200.
Donovan et al., Prevention of murine influenza A virus pneumonitis by surfactant nano-emulsions. Antivir Chem Chemother. Jan. 2000;11(1):41-9.
Fasbender, et al., Optimization of cationic lipid-mediated gene transfer to airway epithelia. Am J Physiol. Jul. 1995;269(1 Pt 1):L45-51.
Felgner et al., Enhanced gene delivery and mechanism studies with a novel series of cationic lipid formulations. J Biol Chem. Jan. 28, 1994;269(4):2550-61.
Felgner, P, et al., Lipofection: a highly efficient, lipid-mediated DNA-transfection procedure. Proc Natl Acad Sci U S A. Nov. 1987;84(21):7413-7.
Goodman & Gilman's "The Pharmacological Basis of Therapeutics" Eds. Hardman et al., 9th Edition, Pub. McGraw Hill, chapters 43 through 50, 1996.
Halvorson et al., Biochemistry of spores of aerobic bacilli with special reference to germination. Bacteriol Rev. Jun. 1957;21(2):112-31.

Hamouda, et al. Antimicrobial mechanism of action of surfactant lipid preparations in enteric Gram-negative bacilli. J Appl Microbiol. Sep. 2000;89(3):397-403.
Hamouda, et al., A novel surfactant nanoemulsion with broad-spectrum sporicidal activity against *Bacillus* species. J Infect Dis. Dec. 1999;180(6):1939-49.
Heyes, J, et al. Synthesis of novel cationic lipids: effect of structural modification on the efficiency of gene transfer. J Med Chem. Jan. 3, 2002;45(1):99-114.
Hills, J. Chemical factors in the germination of spore-bearing aerobes: observations on the influence of species, strain and conditions of growth. J Gen Microbiol. Jan. 1950;4(1):38-47.
Ho, Ea, et al. Characterization of cationic liposome formulations designed to exhibit extended plasma residence times and tumor vasculature targeting properties.J Pharm Sci. Jun. 2010;99(6):2839-53.
Ilies, M. et al. Lipophilic Pyrylium Salts in the Synthesis of Efficient Pyridinium-Based Cationic Lipids, Gemini Surfactants, and Lipophilic Oligomers for Gene Delivery. J Med Chem. Jun. 29, 2006;49(13):3872-87.
International Search Report and Written Opinion, International Patent Application No. PCT/US2017/031958, mailed Aug. 4, 2017, 10 pages.
Janeway et al., Innate immune recognition. Annu Rev Immunol. 2002;20:197-216. Book: Table of Contents Provided.
Janeway, et al. in Immunobiology, "The Immune System in Health and Disease," Second Edition, Current Biology Ltd., London, Great Britain (1996). Book: Table of Contents Provided.
Jouani, et al., Synthesis and Liposome Formation of New Synthetic Perfluoroalkylated Cationic Lipids Derived from N-[[2-(F-Alkyl)Ethylthio]Methyl (Or Propyl] N'(2-Dimethylaminoethyl) Ureas. J. Liposome Research; 1999; 95-114.
Korsholm et al., "Cationic liposomal vaccine adjuvants in animal challenge models: overview and current clinical status." Expert Rev Vaccines. May 2012;11(5):561-77.
Leventis et al., Interactions of mammalian cells with lipid dispersions containing novel metabolizable cationic amphiphiles. Biochim Biophys Acta. Mar. 30, 1990;1023(1):124-32.
Manosroi, A. et al. Development of highly stable and low toxic cationic liposomes for gene therapy. Arzneimittelforschung. 2008;58(10):485-92.
Martin, Remington's Pharmaceutical Sciences, 15th Ed., Mack Publ. Co., Easton, Pa. (1975). Book: Table of Contents Provided.
McCutcheon's vol. 1: Emulsifiers and 20 Detergents North American Edition, 1996. Book: Table of Contents Provided.
McCutcheon's vol. 1: Emulsions and Detergents—North American Edition, 2000. Book: Table of Contents Provided.
Meyers, Surfactant Science and Technology, VCH Publishers Inc., New York, pp. 231-245 (1992).
Ozinsky et al., The repertoire for pattern recognition of pathogens by the innate immune system is defined by cooperation between toll-like receptors. Proc Natl Acad Sci U S A. Dec. 5, 2000;97(25):13766-71.
Perez, L, et al., Gemini surfactants from natural amino acids. Adv Colloid Interface Sci. Mar. 2014;205:134-55.
Shoji et al., Plant-based rapid production of recombinant subunit hemagglutinin vaccines targeting H1N1 and H5N1 influenza. Hum Vaccin. Jan.-Feb. 2011;7 Suppl:41-50.
Solodin et al., A novel series of amphiphilic imidazolinium compounds for in vitro and in vivo gene delivery. Biochemistry. Oct. 17, 1995;34(41):13537-44.
Stamatatos, et al., Interactions of cationic lipid vesicles with negatively charged phospholipid vesicles and biological membranes. Biochemistry. May 31, 1988;27(11):3917-25.
Tadros, T., Applied Surfactants: Principles and Applications (Copyright Aug. 2005 Wiley-VCH Verlag Gmbh & Co. KGaA, Weinheim ISBN: 3-527-30629-3. Book: Table of Contents Provided.
Treanor, JJ, et al., Protective efficacy of a trivalent recombinant hemagglutinin protein vaccine (FluBlok®) against influenza in healthy adults: a randomized, placebo-controlled trial. Vaccine. Oct. 13, 2011;29(44):7733-9.
Yanagita, Biochemical aspects on the germination of conidiospores of Aspergillus niger. Arch Mikrobiol. 1957;26(4):329-44.

(56) References Cited

OTHER PUBLICATIONS

Wong et al., "Formulation, high throughput in vitro screening and in vivo functional characterization of nanoemulsion-based intranasal vaccine adjuvants." PLoS One. May 11, 2015;10(5):e0126120.
Search Report of related 17796763.5, mailed Nov. 22, 2019, 12 pages.

* cited by examiner

FIG. 2

| Arm # | % NE | Surfactant Ratio Blend (Cationic:Nonionic) | Surfactant Ingredients (Cationic, Nonionic) or Other | %DODAC | %CPC |
|---|---|---|---|---|---|
| 1 | 5 | 1:6 | CPC/Tween 80 | - | 0.05% |
| 2 | 5 | 1:1:5 | DODAC/CPC/Tween 80 | 0.05% | 0.05% |
| 3 | 5 | 1:6 | DODAC/Tween 80 | 0.05% | - |
| 4 | 10 | 1:6 | DODAC/Tween 80 | 0.1% | - |
| 5 | 20 | 1:6 | DODAC/Tween 80 | 0.2% | - |
| 6 | - | - | Alum | - | - |
| 7 | - | - | PBS | - | - |

Intramuscular dosing schedule

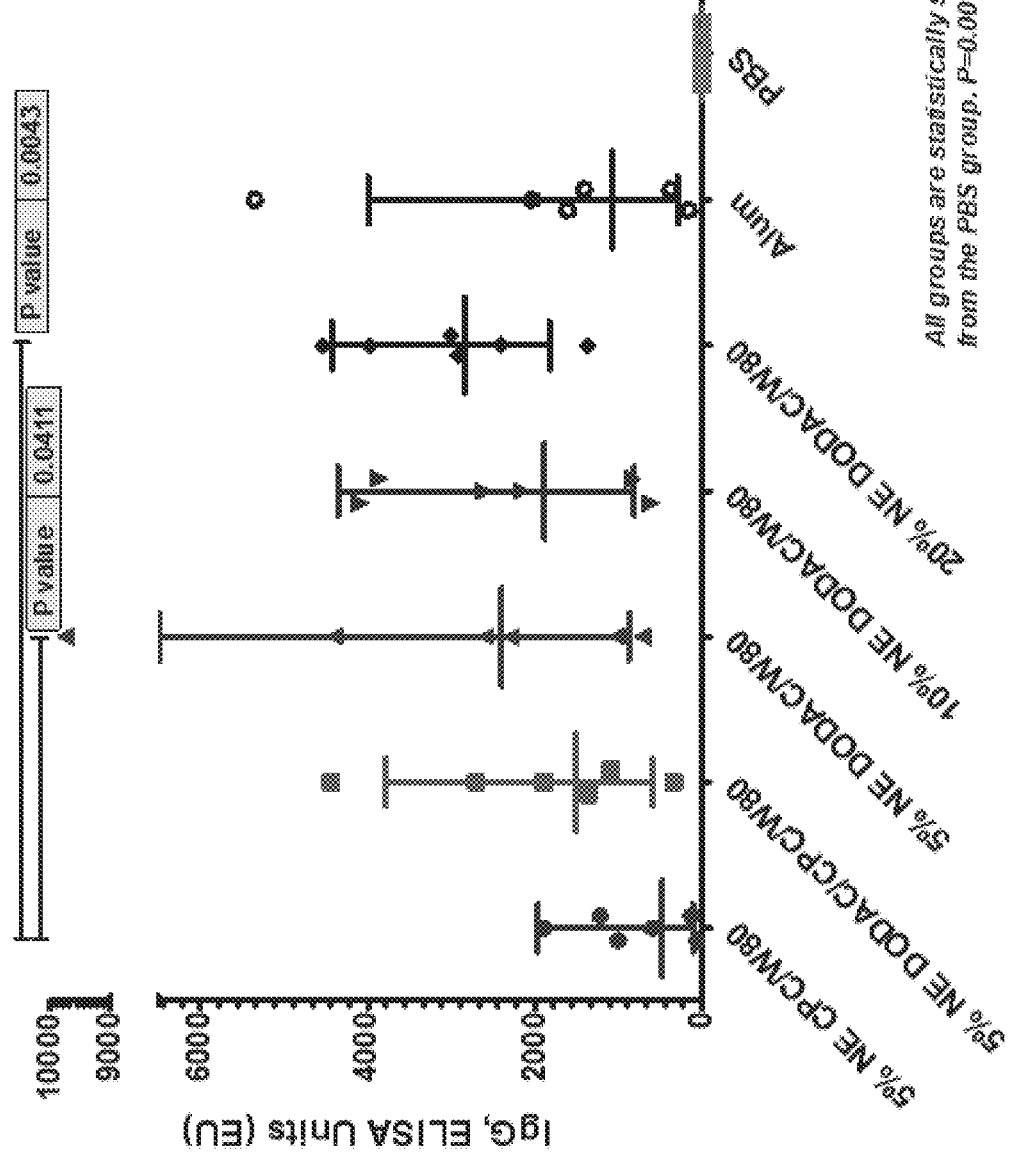

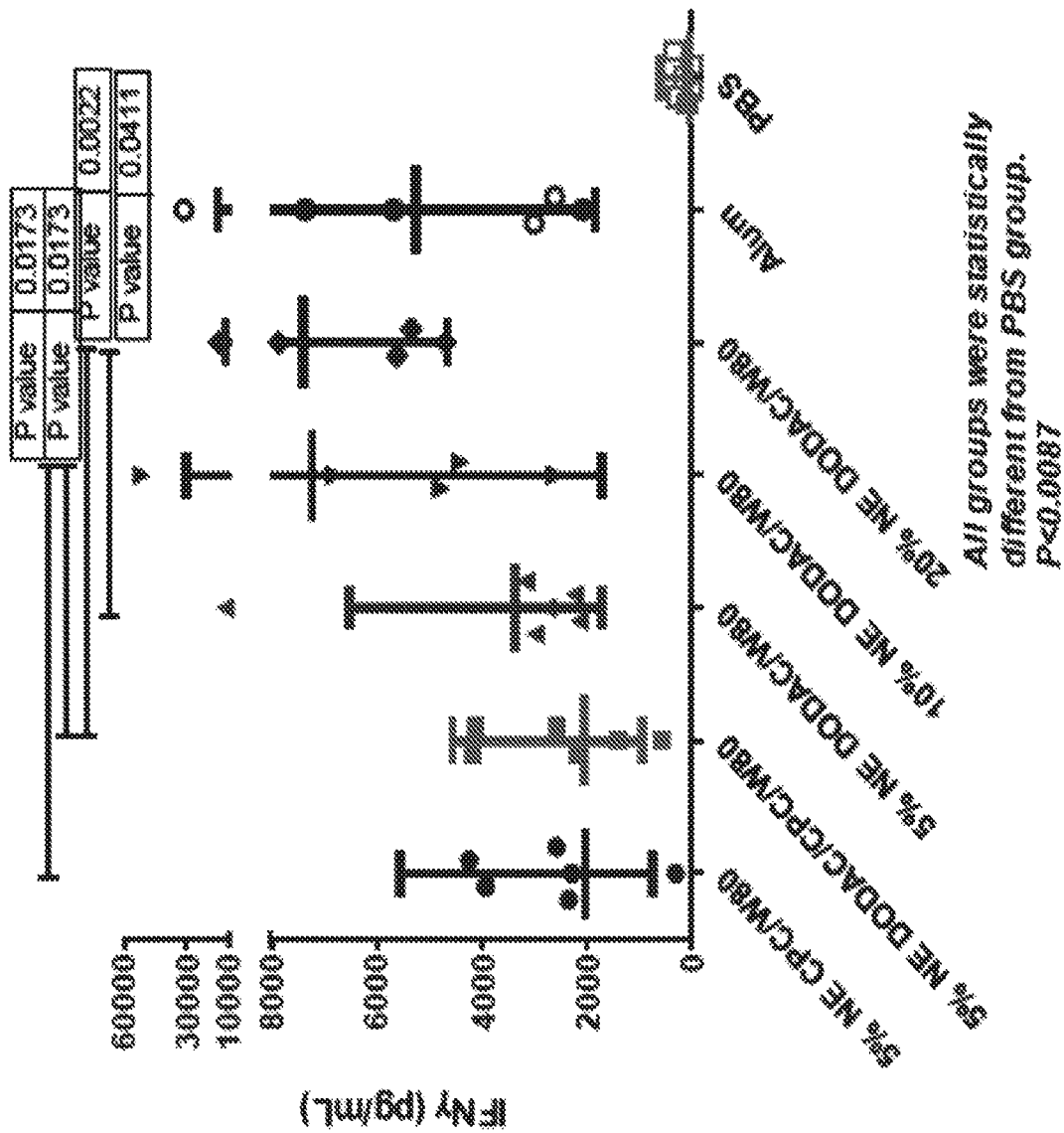

FIG. 9D

Geometric Mean Values for Cytokines

CYTOKINE PROFILE (pg/ml)

| VACCINE | IFNγ | IL-2 | TNFα | IL-4 | IL-5 | IL-10 | IL-13 | IL-17 |
|---|---|---|---|---|---|---|---|---|
| NAIVE | 2 | 1 | 1 | 0 | 1 | 1 | 0 | 0 |
| DODAC | 554 | 28 | 12 | 36 | 4683 | 5289 | 227 | 20 |
| W$_{80}$5EC | 358 | 41 | 16 | 9 | 1825 | 1406 | 255 | 29 |

Cetylpyridinium chloride (CPC)

Dioctadecyl dimethyl ammonium chloride (DODAC)

Serum after 2nd IN immunization

Serum after 2nd IM immunization

A

B

EMULSION ADJUVANT FOR INTRAMUSCULAR, INTRADERMAL AND SUBCUTANEOUS ADMINISTRATION

CROSS REFERENCE TO RELATED APPLICATIONS

This application is a national stage application under 35 U.S.C. § 371 of PCT/US17/31958, filed May 10, 2017, which claims priority to U.S. Provisional Application No. 62/334,267 filed May 10, 2016, each of which are hereby incorporated by reference in their entirety.

STATEMENT REGARDING FEDERALLY SPONSORED RESEARCH OR DEVELOPMENT

This invention was made with government support under HHSN272201300028C and HHSN272200900031C awarded by the National Institutes of Health/National Institute of Allergy and Infectious Diseases. The government has certain rights in the invention.

FIELD OF THE INVENTION

The present invention provides compositions comprising emulsion adjuvant and one or more active agents or substances formulated for infusion or injection into a subject (e.g., using a syringe and needle), as well as methods of formulating and using the same (e.g., as an injectable medicinal composition (e.g., a vaccine)). The emulsion adjuvant of an immunogenic composition of the invention in its preferred form comprises a cationic lipid containing a polar head group and a hydrophobic component (e.g., a dual chain hydrophobic group (e.g., the cationic surfactant dioctadecyl dimethyl ammonium chloride (DODAC) and dioctadecyl dimethyl ammonium bromine (DODAB))). Compositions of the invention comprising emulsion adjuvant and one or more active agents or substances formulated for administration via injection to a subject find use in treatment and/or prevention of infectious disease, cancer and/or allergy.

BACKGROUND OF THE INVENTION

A route of administration in medicine, pharmacology, and toxicology is the path by which a medicine, fluid, or other substance is taken into the body. Routes of administration are generally classified by the location at which the substance is applied. For example, common routes of administration are oral and via injection (e.g., intramuscular, intradermal and subcutaneous administration). Routes are also classified based on where the target of action occurs. For example, target action may be topical (local), enteral (system-wide action, but delivered through the gastrointestinal tract), or parenteral (system-wide action, but delivered by routes other than the gastrointestinal tract (e.g., via injection).

The body's immune system activates a variety of mechanisms for attacking foreign material (e.g., pathogens or antigenic portions thereof (See, e.g., Janeway, Jr, C A. and Travers P., eds., in Immunobiology, "The Immune System in Health and Disease," Second Edition, Current Biology Ltd., London, Great Britain (1996))). However, not all of these mechanisms are necessarily activated after immunization. For example, protective immunity induced by immunization is dependent upon the capacity of an immunogenic composition to elicit an appropriate immune response to resist or eliminate the foreign pathogen. Depending on the pathogen, cell-mediated and/or humoral immune responses are important for pathogen neutralization and/or elimination.

Many antigens are poorly immunogenic or non-immunogenic when administered by themselves. Accordingly, strong adaptive immune responses to antigens have generally required that antigens be administered together with an adjuvant, a substance that enhances the immune response (See, e.g., Audbert, F. M. and Lise, L. D. 1993 Immunology Today, 14: 281-284). Many adjuvants function Parenteral immunization regimens are usually ineffective in inducing secretory IgA responses. Secretory immunity is most often achieved through the direct immunization of mucosally associated lymphoid tissues. Following their induction at one mucosal site, the precursors of IgA-producing plasma cells extravasate and disseminate to diverse mucosal tissues where final differentiation to high-rate IgA synthesis occurs (See, e.g., Crabbe, P. A., et al., 1969 J. Exptl. Med., 130, 723-744; Bazin, H., et al., 1970 J. Immunol., 105, 1049-1051; Craig, S. W., and Cebra, J. J., 1971 J. Exptl. Med., 134, 188-200).

SUMMARY OF THE INVENTION

The present invention provides compositions comprising emulsion adjuvant and one or more active agents or substances formulated for infusion or injection into a subject (e.g., using a syringe and needle), as well as methods of formulating and using the same (e.g., as an injectable medicinal composition (e.g., a vaccine)). The emulsion adjuvant of an immunogenic composition of the invention in its preferred form comprises a cationic lipid containing a polar head group and a hydrophobic component (e.g., a dual chain hydrophobic group (e.g., the cationic surfactant dioctadecyl dimethyl ammonium chloride (DODAC) and dioctadecyl dimethyl ammonium bromine (DODAB))). Compositions of the invention comprising emulsion adjuvant and one or more active agents or substances formulated for administration via injection to a subject find use in treatment and/or prevention of infectious disease, cancer and/or allergy.

Accordingly, in one embodiment, the invention provides an injectable composition comprising a cationic lipid containing a polar head and a dual chain hydrophobic group attached to the polar head, a non-ionic surfactant, and an organic solvent. In another embodiment, the injectable composition further comprises oil and water. In still another embodiment, the injectable composition is an oil in water emulsion. The invention is not limited by the type of cationic lipid. Indeed, a variety of cationic lipids find use in the invention including, but not limited to, dioctadecyldimethylammonium chloride (DODAC), di(soyoylethyl) hydroxyethylmonium methosulfate (DSHM); N—[I-(2,3-dioleyloxy)propyl]-N,N,N-trimethylammonium bromide (DOTMA), 1,2-dimyristyloxypropyl-N,N-dimethyl-hydroxyethyl ammonium bromide (DMRIE), [N—(N,N'-dimethylaminoethane)carbamoyl] cholesterol (DC-Chol), dioctadecylamidoglycyl spermidine (DOGS), dimethyl dioctadecylammonium bromide (DDAB), dioleoyl phosphatidylethanolamine (DOPE), 2,3-dioleoyloxyl-N[2(sperminecarbozamide-O-ethyl]-N,N-dimethyl-propanaminium trifluoroacetate (DOSPA), I-[2-(oleoyloxy)-ethyl]-2-oleyl-3-(2-hydroxyethyl)imidazolinium chloride (DOTIM), 1,2-dioleoyloxy-3-(trimethylammonio)propane (DOTAP), 1,2-diacyl-3-trimethylammonium propane (TAP), 1,2-diacyl-3-dimethylammonium propane (DAP), a quaternary dimethyldiacyl amines possessing from 8 carbon atoms to 30 carbon atoms, dicocodimonium chloride (Quaternium 34), quaternary dimethyldiacyl amines wherein the acyl groups have from 8 carbon atoms to 30 carbon atoms, dimethyl dihydrogenated tallow ammonium chloride (Quaternium 18), and/or decyl dimethyl octyl ammonium chloride (Quaternium 24). In one preferred embodiment, the cationic lipid is DODAC. In another preferred embodiment, the cationic lipid is DODAB. The invention is likewise not limited by the type of nonionic surfactant. The nonionic surfactant may be one or more of an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis(imidazoyl carbonyl)), nonoxynol-9, Bis(polyethylene glycol bis(imidazoyl carbonyl)), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methyl-glucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, a poloxamer, semi-synthetic derivatives thereof, or combinations thereof. In a preferred embodiment, the nonionic surfactant is a polysorbate (e.g., polysorbate 20 and/or polysorbate 80). In a preferred embodiment, the injectable composition is physically stable after undergoing means of sterilization. The invention is not limited by the means of sterilization. In one embodiment, sterilization comprises autoclaving (e.g., heating at 121 C for 15 minutes). In one embodiment, the injectable composition further comprises and antigen and/or immunogen. The invention is not limited by the type of antigen and/or immunogen used. Exemplary antigens and/or immunogens include, but are not limited to, an inactivated microbial pathogen, an isolated and/or recombinant peptide, an isolated and/or recombinant protein, a glycoprotein, a lipoprotein, a glycopeptide, a lipopeptide, a toxoid, a carbohydrate, and/or a tumor-specific antigen. In one embodiment, the injectable composition is a component of a pharmaceutical composition. In another embodiment, the injectable composition is or is a component of a vaccine.

In some embodiments, an injectable composition of the invention is formulated to comprise between 0.1 and 500 µg of a protein antigen (e.g., derived or isolated from a pathogen and/or a recombinant form of an immunogenic pathogen component). However, the present invention is not limited to this amount of protein antigen. For example, in some embodiments, more than 500 µg of protein antigen is present in an injectable composition for administration to a subject. In some embodiments, less than 0.1 µg of protein antigen is present in an injectable composition for administration to a subject.

In some embodiments, an injectable composition comprises one or more inactivated pathogens (e.g., an inactivated virus, inactivated bacteria, etc.) for administration to a subject (e.g., such that between about 10 and $10^7$ pfu (e.g., about $10^2$, $10^3$, $10^4$, $10^5$, or $10^6$ pfu) of the inactivated pathogen is present in a dose administered to the subject). However, the present invention is not limited to this amount of inactivated pathogen present in an injectable composition. For example, in some embodiments, more than $10^7$ pfu of inactivated pathogen (e.g., $10^8$ pfu, $10^9$ pfu, or more) is present in a dose administered to the subject.

In one embodiment, a composition comprising a 10% nanoemulsion solution is utilized (e.g., in an injectable composition of the invention (e.g., an injectable immunogenic composition (e.g., an injectable vaccine))). However, the present invention is not limited to this amount (e.g., percentage) of nanoemulsion. For example, in some embodiments, an injectable composition comprises less than 10% nanoemulsion (e.g., 9%, 8%, 7%, 6%, 5%, 4%, 3%, 2%, 1%, 0.5% or less). In some embodiments, an injectable composition comprises more than 10% nanoemulsion (e.g., 15%, 20%, 25%, 30%, 35%, 40%. 45%, 50%, 60%, 70%, 80%, 90%, or more). In one embodiment, an immune responses in a subject resulting from administration via injection of an injectable composition of the invention prevents a subject from displaying signs or symptoms of disease, or treats signs, symptoms or the underlying etiology of disease.

In one embodiment, the invention provides an immunogenic composition formulated for administration via injection, the immunogenic composition not being detectably immunogenic or less immunogenic when administered mucosally, the immunogenic composition comprising an oil in water emulsion comprising a cationic lipid containing a polar head and a dual chain hydrophobic group attached to the polar head, a non-ionic surfactant, an organic solvent, oil and water; and an antigen. In one embodiment, the immunogenic composition is significantly less immunogenic when administered mucosally (e.g., when administered via injection, the immunogenic composition is significantly more immunogenic than when administered mucosally (e.g., intranasally)). By immunogenic, it is meant that when administered to a subject, the immunogenic composition induces an immune response. The invention is not limited by the type of immune response generated and refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response). Immune responses include, but are not limited to, detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, B cell activation (e.g., antibody generation and/or secretion), binding of an immunogen (e.g., antigen (e.g., immunogenic polypeptide)) to an MHC molecule and inducing a cytotoxic T lymphocyte ("CTL") response, inducing a B cell response (e.g., antibody production), T-helper lymphocyte response, a delayed type hypersensitivity (DTH) response against antigen (e.g., from which an immunogenic polypeptide is derived), expansion (e.g., growth of a population of cells) of cells of the immune system (e.g., T cells, B cells (e.g., of any stage of development (e.g., plasma cells), and/or increased processing and presentation of antigen by antigen presenting cells. In some embodiments the immunogenic composition formulated for administration via injection fails to produce a detectable Th1 response (e.g., comprising detectable levels of IFN-γ) when administered mucosally (e.g., intranasally). The invention is not limited by the route of injectable administration. Indeed, a variety of routes of administration via injection and/or infusion find use with the compositions and methods of the invention including, but not limited to, intradermal, subcutaneous, intramuscular, intravenous, intraosseous, intraperitoneal, intrathecal, epidural, intracardiac, intraarticular, intracavernous, micropenetrators, microdialysis, and/or intravitreal.

The invention also provides, in one embodiment, a method of inducing an immune response to an antigen in a subject comprising administering via injection to the subject an effective amount of an immunogenic composition comprising an oil in water emulsion comprising a cationic lipid containing a polar head and a dual chain hydrophobic group attached to the polar head, a non-ionic surfactant, an organic solvent, oil and water; and an antigen. The invention is not limited by the type of immunogenic composition comprising an oil in water emulsion comprising a cationic lipid containing a polar head and a dual chain hydrophobic group attached to the polar head. Indeed, any immunogenic composition comprising an oil in water emulsion comprising a cationic lipid containing a polar head and a dual chain hydrophobic group attached to the polar head described herein may be used. In one embodiment, the effective amount of the immunogenic composition produces a lower antigen specific immune response (e.g., a significantly lower antigen specific immune response or the absence of a detectable antigen specific immune response) when administered mucosally to a control subject (e.g. the immunogenic composition induces a significantly greater immune response when administered via injection than when administered via a mucosal route (e.g., intranasally)). The invention is not limited by the type of immune response induced using an immunogenic composition of the invention. Indeed, any immune response described herein (e.g., that is measurable) may be induced. The invention is not limited by the route of injectable administration. Indeed, a variety of routes of administration via injection and/or infusion find use with the compositions and methods of the invention including, but not limited to, intradermal, subcutaneous, intramuscular, intravenous, intraosseous, intraperitoneal, intrathecal, epidural, intracardiac, intraarticular, intracavernous, micropenetrators, microdialysis, and/or intravitreal.

In another embodiment, the invention provides a composition (e.g., a syringe) comprising an immunogenic composition formulated for administration via injection of the invention.

In another embodiment, the invention provides a method of formulating a composition comprising an immunogenic composition for administration via injection of the invention (e.g., using any one or more of the formulation methods described herein).

DESCRIPTION OF THE DRAWING

The following figures form part of the present specification and are included to further demonstrate certain aspects and embodiments of the present invention. The invention may be better understood by reference to one or more of these figures in combination with the description of specific embodiments presented herein.

FIG. 1A shows a summary of stability analysis of tested emulsions (light grey: stable, dark grey: unstable). A significant amount of instability was observed for emulsions formulated with Benzalkonium Chloride (BAC). FIG. 1B shows a three-dimensional analysis of mucoadhesion, antigen uptake and cell cytotoxicity with varying cationic surfactant families within a multitude of nanoemulsion formulations analyzed and characterized. Reactivity patterns of different formulations within the nanoemulsion library as determined by high-throughput screening assays for cell cytotoxicity, mucoadhesion, and NE-facilitated antigen uptake with varying cationic surfactant defines the clustering shown. The cationic surfactant is dominant while the nonionic surfactant provides additional diversity.

FIG. 2 shows the study design used for experiments comparing different nanoemulsion formulations combined with RSV F protein for intramuscular administration in one embodiment of the invention.

FIG. 3 shows administration of immunogenic compositions, analysis dates and sacrifice dates for mice intramuscularly administered various nanoemulsion formulations in combination with RSV F protein.

FIG. 4 shows IgG titers generated at day 14 in mice administered various nanoemulsion formulations in combination with RSV F protein. Animals were vaccinated intramuscularly with vaccines containing 2 μg of F protein/dose, adjuvanted with either 5% W805EC, or 5, 10, or 20% DODAC nanoemulsions. Alum-adjuvanted vaccine with the same amount of antigen was used as a positive control. Sera was collected and analyzed by ELISA as described in Materials and Methods. Levels of IgG are expressed in ELISA Units (EU)

FIG. 5A shows IgG titers responses generated at two weeks after second vaccination. Animals were vaccinated intramuscularly with vaccines containing 2 µg of F protein/dose, adjuvanted with either 5% W805EC, or 5, 10, or 20% DODAC nanoemulsions. Alum-adjuvanted vaccine with the same amount of antigen was used as a positive control. Sera was collected and analyzed by ELISA as described in Example 2. Levels of IgG are expressed in ELISA Units (EU). FIG. 5B also shows neutralization activity at 2 weeks after the second vaccination. Animals were vaccinated intramuscularly with vaccines containing 2 µg of F protein/dose, adjuvanted with either 5% W805EC, or 5, 10, or 20% DODAC nanoemulsions. Alum-adjuvanted vaccine with the same amount of antigen was used as a positive control. Virus neutralization activity in the sera of vaccinated animals was analyzed as described Example 2. Neutralizing antibody titers are expressed in neutralization units at 50%, which was determined as a reciprocal of the sera dilution that reduces number of the plaques by 50%.

FIG. 6 shows Th1/Th17 cytokine production in mice administered various nanoemulsion formulations in combination with RSV F protein. Cytokine profiles in stimulated solenocytes were measured by Milliplex 2 weeks after second immunization: IFN-γ (A); TNF-α (B); IL-2 (C); IL-17 (D). Cells were plated at $5\times10^5$ cells/well in 150 µl of media in 96-well plates and stimulated with 5 µg/ml RSV F protein for 96 hours as described in Example 2.

FIG. 7 shows Th2 cytokine production in mice administered various nanoemulsion formulations in combination with RSV F protein. Cytokine profiles in stimulated solenocytes were measured by Milliplex 2 weeks after second immunization: IL-4 (A); IL-5 (B); IL-10 (C); IL-13 (D). Cells were plated at $5\times10^5$ cells/well in 150 µl of media in 96-well plates and stimulated with 5 µg/ml RSV F protein for 96 hours as described in Example 2.

FIG. 8 shows the evaluation of serum rH5-specific antibody responses after intramuscular immunization of CD-1 mice using nanoemulsion formulations containing CPC or DODAC (DD) as the cationic surfactant. CD-1 mice received a series of 3 intramuscular immunizations using 5% nanoemulsion consisting of $W_{80}EC$ (CPC cationic surfactant) or DODAC (DD) NE in combination with 10 µg rH5 antigen at 2 week intervals. rH5-specific IgG was determined in serum by ELISA at week 4 after 2 immunizations, or at week 6 after 3 immunizations (Panel A). Similarly, "functional" hemagglutination inhibiting (HAI) antibodies were evaluated in serum at week 6 after 3 immunizations (Panel B) using horse red blood cells as described in the Methods section. A cut-off endpoint titer of ≥1:40 has been established as a correlate of protection for HAI antibody responses (dotted line), and the percentage of responders for each group is shown at top. Error bars show geometric mean titer with 95% confidence intervals.

FIG. 9 shows evaluation of rH5-specific cell-mediated immunity after intramuscular immunization of mice using emulsion formulations containing CPC or DODAC as the cationic surfactant. Spleen cells were harvested from CD-1 mice at the time of sacrifice at week 6 (2 weeks after the third intramuscular immunization). The cells were cultured in medium alone, or with addition of 5 µg/ml rH5 antigen. Cell-free supernatants harvested at 72 hours were evaluated for cytokine profiles by LUMINEX™ multiplex analysis. The concentration of cytokines produced in medium control cultures (background) was subtracted from the concentration produced in antigen-stimulated cultures (pg/ml). Error bars show geometric mean (pg/ml) and 95% confidence interval (Panels A-C). Geometric mean values for each group are also tabulated (Panel D).

Figure 16:
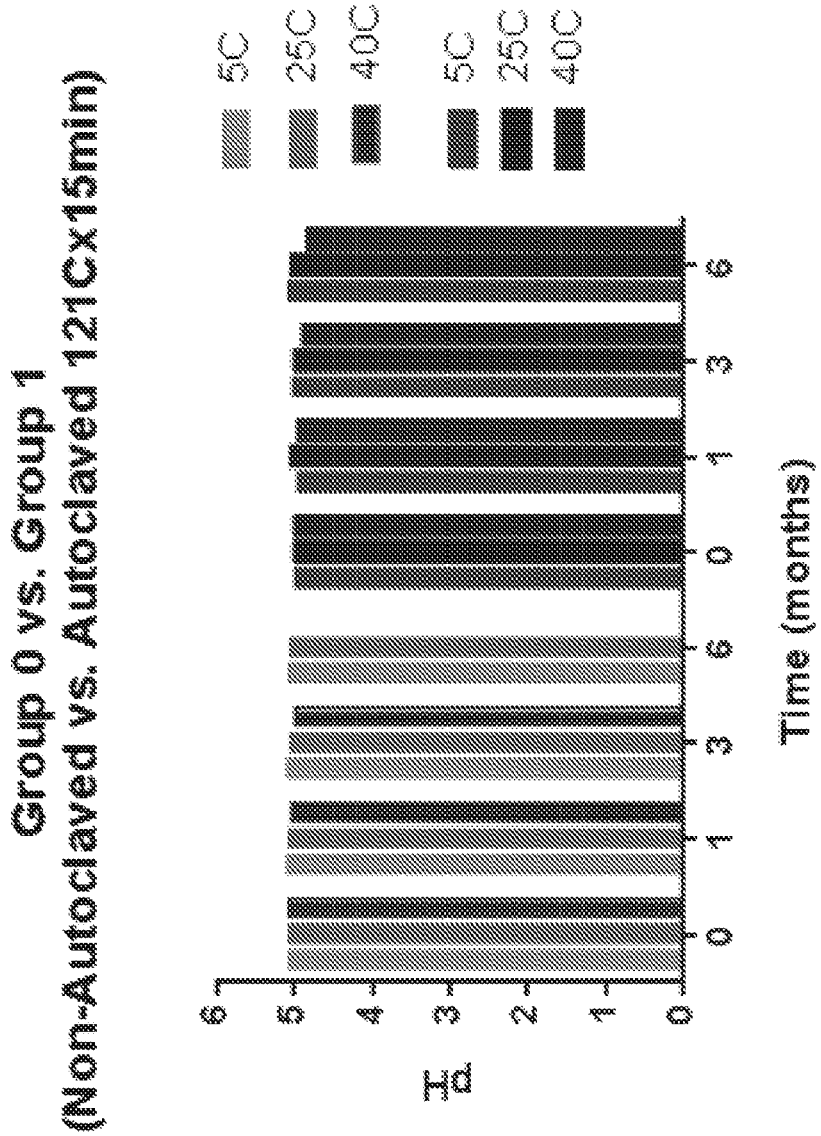

FIG. 16 shows pH after storage of autoclaved emulsion 60% $W_{80}5EC$ over 6 months at 5° C., 25° C. or 40° C. and 6 months storage at 5° C. and 25° C.

Figure 17:
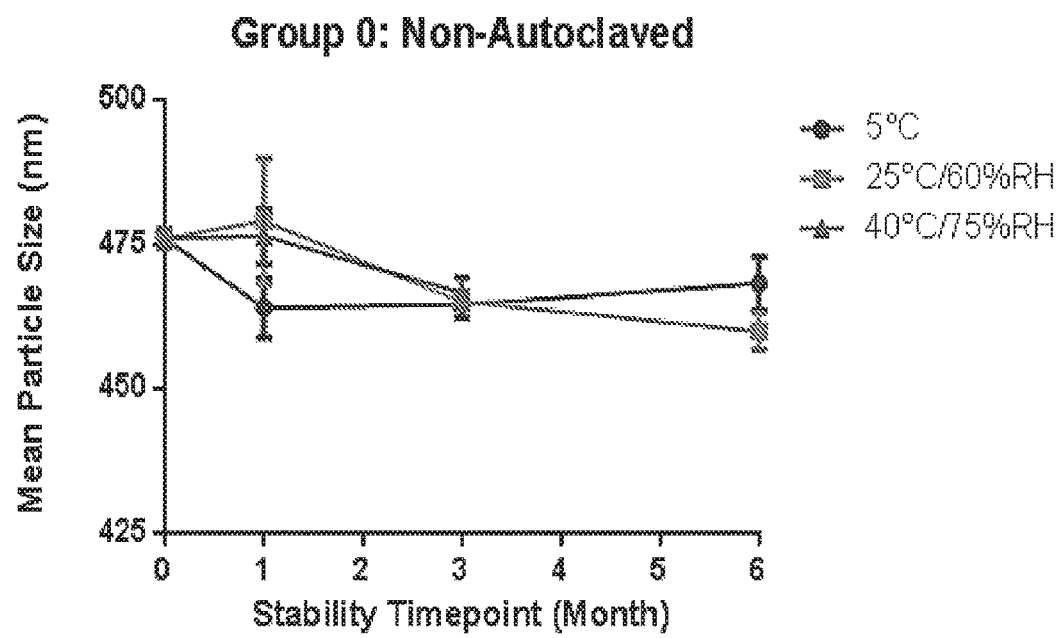
Figure 17:
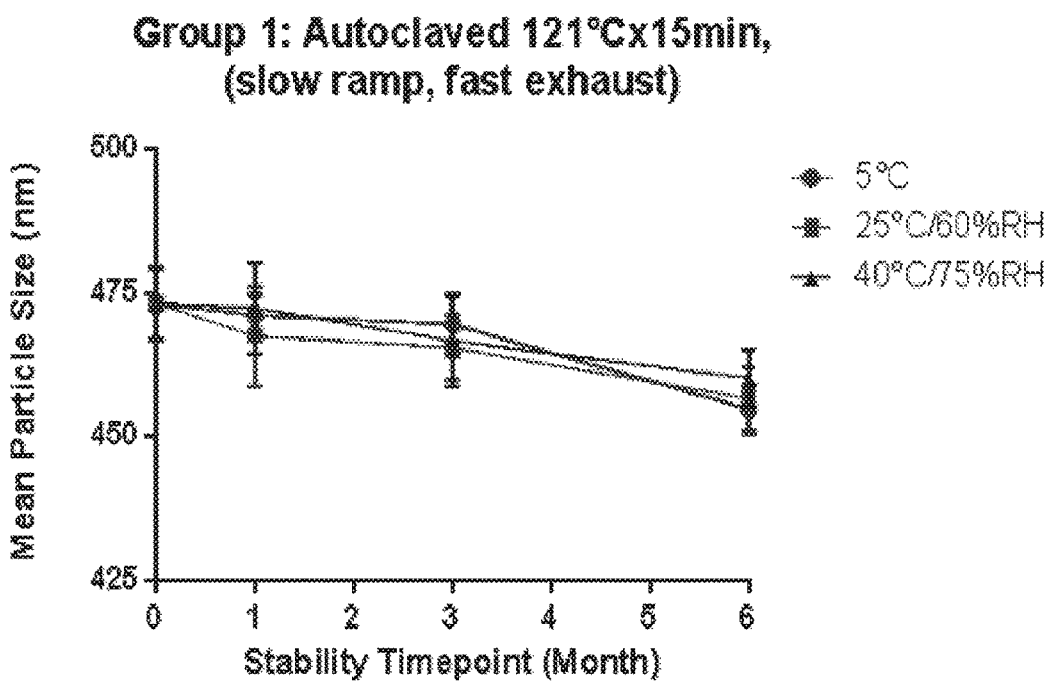

FIG. 17 shows Mean Particle Size (Z-average) of 60% $W_{80}5EC$ A) Non-Autoclaved and B) Autoclaved at 5° C., 25° C. and 40° C. up to 6 months.

Figure 18:
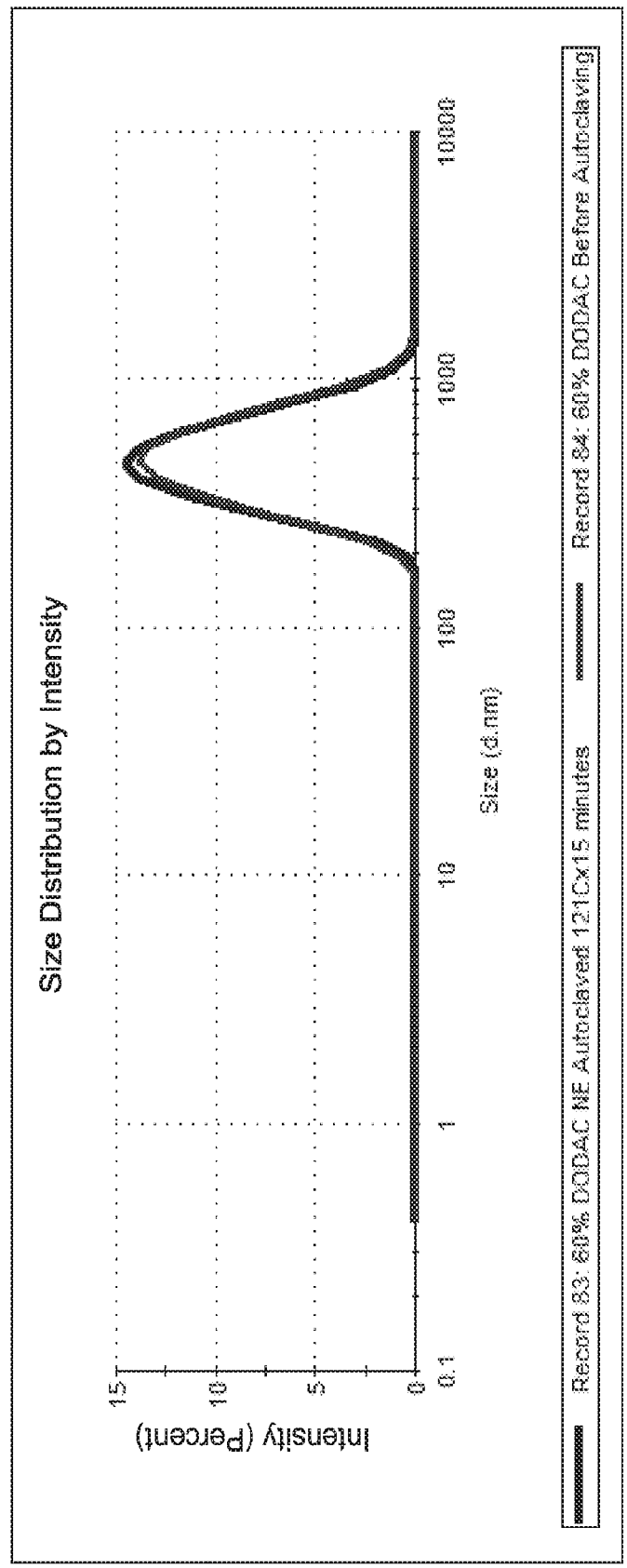

FIG. 18 shows Particle Size Overlay Profiles of the 60% DODAC Formulation Before and After Autoclaving at 121° C. for 15 minutes.

DEFINITIONS

To facilitate an understanding of the present invention, a number of terms and phrases are defined below.

As used herein, the term "microorganism" refers to any species or type of microorganism, including but not limited to, bacteria, viruses, archaea, fungi, protozoans, *mycoplasma*, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, *mycoplasma*, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Strepto-*

*myces*, and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, hyper-immune responses, hyper-sensitivity, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., allergens, malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered (e.g., injectably administered)) compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered (e.g., injectably administered) or who has been administered one or more compositions of the present invention (e.g., an injectable composition for inducing an immune response comprising a select nanoemulsion formulated for injection and one or more antigens).

As used herein, the terms "inactivating," "inactivation" and grammatical equivalents, when used in reference to a microorganism (e.g., a pathogen (e.g., a bacterium or a virus)), refer to the killing, elimination, neutralization and/or reducing of the capacity of the microorganism (e.g., a pathogen (e.g., a bacterium or a virus)) to infect and/or cause a pathological response and/or disease in a host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium or bacterial spore). In preferred embodiments of the present invention, the presence of a lysogenic and a fusigenic agent in the same composition produces an enhanced inactivating effect compared to either agent alone. Methods and compositions (e.g., for inducing an immune response (e.g., used as a vaccine) using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in some embodiments, the nanoemulsions comprise an oil phase having droplets with a mean particle size of approximately 0.1 to 5 microns (e.g., about 100, 150, 200, 250, 300, 350, 400, 450, 500 nm or larger in diameter), although smaller and larger particle sizes are contemplated. The terms "emulsion" and "nanoemulsion" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion inactivates the microorganism or pathogenic agent, if present. The present invention is not limited by the amount or type of nanoemulsion used for microorganism inactivation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion (e.g., sufficient for inactivating the microorganism (e.g., virus inactivation)) and microorganisms (e.g., sufficient to provide an antigenic composition (e.g., a composition capable of inducing an immune response)) are contemplated in the present invention including, but not limited to, those described herein.

The term "surfactant" refers to any molecule having both a polar head group, which energetically prefers solvation by water, and a hydrophobic tail that is not well solvated by water. The term "cationic surfactant" refers to a surfactant with a cationic head group. The term "cationic lipid" refers to a positively charged molecule comprising a positively charged head group and one or more (e.g., two, three or more) hydrocarbon chains. The term "anionic surfactant" refers to a surfactant with an anionic head group. When a single surfactant molecule exhibit both anionic and cationic dissociations it is called amphoteric or zwitterionic. For example, this is the case of synthetic products like betaines or sulfobetaines and natural substances such as amino acids and phospholipids. Polymeric surfactants and surface active polymers result from the association of one or several macromolecular structures exhibiting hydrophilic and lipophilic characters, either as separated blocks or as grafts.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, *Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis (oxyethylenenitrilo)tetraacetic acid (EGTA), and the like) and certain biological agents (e.g., bovine serum albumin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., modulating an existing immune response (e.g., an allergic immune response) and/or resulting in total or partial immunity to a microorganism (e.g., pathogen) capable of causing disease). In preferred embodiments of the invention, the composition comprises a nanoemulsion formulated for injectable administration and one or more immunogens. In further preferred embodiments, the composition comprising a nanoemulsion formulated for injectable administration and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, a composition comprising a nanoemulsion formulated for injectable administration and an immunogen is administered to a subject as a vaccine (e.g., to prevent or attenuate a disease (e.g., allergic disease (e.g., by providing to the subject total or partial immunity against the disease or the total or partial attenuation (e.g., suppression) of a sign, symptom or condition of the disease (e.g., sign, symptom or condition of an allergic disease)))).

As used herein, the term "adjuvant" refers to any substance that can stimulate an immune response. Some adjuvants can cause activation of a cell of the immune system (e.g., an adjuvant can cause an immune cell to produce and secrete a cytokine). Examples of adjuvants that can cause activation of a cell of the immune system include, but are not limited to, the nanoemulsions formulated for injectable administration described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). Traditional adjuvants are well known in the art and include, for example, aluminum phosphate or hydroxide salts ("alum").

As used herein, the term "an amount effective to induce an immune response" (e.g., of a composition for inducing an immune response comprising a nanoemulsion formulated for injectable administration), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route. Accordingly, a "therapeutically effective amount" (e.g., of a composition for inducing an immune response comprising a nanoemulsion formulated for injectable administration), refers to the dosage level or amount of a composition required (e.g., when administered to a subject (e.g., administered via injection)) to stimulate, generate and/or elicit a therapeutic benefit in a subject. An therapeutically effective amount can be administered in one or more administrations (e.g., via the same or different route), applications or dosages and is not intended to be limited to a particular formulation or administration route.

As used herein, the term "under conditions such that said subject generates an immune response" and grammatical equivalents refer to any qualitative or quantitative induction, generation, and/or stimulation of an immune response (e.g., innate or acquired).

A used herein, the term "immune response" and grammatical equivalents refer to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the terms "toll receptors" and "TLRs" refer to a class of receptors (e.g., TLR1, TLR2, TLR3, TLR4, TLR5, TLR6, TLR7, TLR8, TLR9, TLR10, TLR 11) that recognize special patterns of pathogens, termed pathogen-associated molecular patterns (See, e.g., Janeway and Medzhitov, (2002) Annu. Rev. Immunol. 20, 197-216). These receptors are expressed in innate immune cells (e.g., neutrophils, monocytes, macrophages, dendritic cells) and in other types of cells such as endothelial cells. Their ligands include bacterial products such as LPS, peptidoglycans, and lipopeptides. TLRs are receptors that bind to exogenous ligands and mediate innate immune responses leading to the elimination of invading microbes. The TLR-triggered signaling pathway leads to activation of transcription factors including NFkB, which is important for the induced expression of proinflammatory cytokines and chemokines. TLRs also interact with each other. For example, TLR2 can form functional heterodimers with TLR1 or TLR6. The TLR2/1 dimer has different ligand binding profile than the TLR2/6 dimer (Ozinsky et al., 2000). In some embodiments, a nanoemulsion adjuvant activates cell signaling through a TLR (e.g., TLR2 and/or TLR4). Thus, methods described herein include a nanoemulsion adjuvant composition (e.g., composition comprising NE adjuvant optionally combined with one or more immunogens (e.g., proteins and/or NE adjuvant inactivated pathogen (e.g., a virus (e.g., VV)))) that when administered to a subject, activates one or more TLRs and stimulates an immune response (e.g., innate and/or adaptive/acquired immune response) in a subject. Such an adjuvant can activate TLRs (e.g., TLR2 and/or TLR4) by, for example, interacting with TLRs (e.g., NE adjuvant binding to TLRs) or activating any downstream cellular pathway that occurs upon binding of a ligand to a TLR. NE adjuvants described herein that activate TLRs can also enhance the availability or accessibility of any endogenous or naturally occurring ligand of TLRs. A NE adjuvant that activates one or more TLRs can alter transcription of genes, increase translation of mRNA or increase the activity of proteins that are involved in mediating TLR cellular processes. For example, NE adjuvants described herein that activate one or more TLRs (e.g., TLR2 and/or TLR4) can induce expression of one or more cytokines (e.g., IL-8, IL-12p40, and/or IL-23).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired/adaptive (e.g., immune responses that are mediated by B and T cells following a previous exposure to antigen (e.g., that exhibit increased specificity and reactivity to the antigen)).

As used herein, the terms "immunogen" and "antigen" are used interchangeably to refer to an agent (e.g., a microorganism (e.g., bacterium, virus or fungus) and/or portion or component thereof (e.g., protein, glycoprotein, lipoprotein, peptide, glycopeptide, lipopeptide, toxoid, carbohydrate, tumor-specific antigen, etc.)) that is capable of eliciting an immune response in a subject. In preferred embodiments, immunogens elicit immunity against the immunogen (e.g., microorganism (e.g., pathogen or a pathogen product), cancer and/or tumor, etc.) when administered in combination with a nanoemulsion formulated for administration via injection of the present invention.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response (e.g., a composition comprising a nanoemulsion formulated for administration via injection and an immunogen)) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like. A preferred route of administration, according to the invention, is via injection (e.g., intradermal, subcutaneous, intramuscular, intravenous, intraosseous, intraperitoneal, intrathecal, epidural, intracardiac, intraarticular, intracavernous, micropenetrators, microdialysis, and/or intravitreal).

As used herein, the terms "co-administration" and "co-administering" refer to the administration of at least two agent(s) (e.g., a composition comprising a nanoemulsion formulated for administration via injection and an immunogen and one or more other agents or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., microorganisms (e.g., pathogens)) at or near the same time (e.g., when a subject is unlikely to be available for subsequent administration of a second, third, or more composition for inducing an immune response).

As used herein, the term "topically" refers to application to the surface of the skin and/or mucosal cells and tissues (e.g., alveolar, buccal, lingual, masticatory, vaginal or nasal mucosa, and other tissues and cells which line hollow organs or body cavities). Topical administration may utilize a spray (e.g., a nasal spray), a cream, or other viscous solution.

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

"Vaginal application", as used herein, means applied into or through the vagina so as to contact vaginal mucosa. The application may contact the urethra, cervix, fornix, uterus or other area surrounding the vagina. The application may, for example, be done by drops, sprays, mists, coatings, lubricants or mixtures thereof applied to the vagina or surrounding tissue.

As used herein, the term "kit" refers to any delivery system for delivering materials. In the context of immunogenic agents (e.g., compositions comprising a nanoemulsion formulated for administration via injection and an immunogen), such delivery systems include systems that allow for the storage, transport, or delivery of immunogenic agents and/or supporting materials (e.g., written instructions for using the materials, a syringe and/or needle, etc.). For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion and an immunogen for a particular use, while a second container contains a second agent (e.g., a syringe and/or needle). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

DETAILED DESCRIPTION OF THE INVENTION

Development of dialkyl (dual chained) cationic surfactants has attracted considerable interest because of their use in biomedical applications (See, e.g., Pérez, L, et al., Adv. Colloid Interface Sci. 205(2014) 134; Manosroi, A. et al. Gene Ther. 58 (2008) 485). Most of the studies use dual chained lipid to construct the bilayers in a liposomal system. For example, Ho et al. showed that cationic liposomes prepared of DSPC, cationic lipids (DODAC, DOTAP, or DC-CHOL), and DSPE-PEG(2000) exhibit both extended circulation lifetimes and tumor vascular targeting properties (See, e.g., Ho E A, et al. J Pharm Sci. 2010 June; 99(6): 2839-53). Several cationic lipids such as DOTMA (1,2-dioctadecenyl-3-trimethylammonium propane) or DOTAP (1,2-dioleoyl-3-trimethylammonium-propane) have been used to prepare cationic niosomes for pharmaceutical applications (See, e.g., Llies, M. et al. J. Med. Chem. 49 (2006) 3872; Heyes, J, et al. J. Med. Chem. 45(2002) 99). However, the inclusion of a cationic dual chained lipid/surfactant in an emulsion has not been the focus of research and it is unknown how the presence of a cationic dual chained lipid/surfactant in an emulsion would behave and how it would alter the properties of the emulsion itself (e.g., its stability, charge, usefulness, etc.).

Liposomes contain dual chained lipids. Neutral liposomes do not interact significantly with cells, and this causes drug release from the liposomes in the extracellular space. The art describes several studies carried out on the potential use of charged liposomes for biomedical applications. Negatively charged liposomes are generally constituted by anionic lipids, such as dimyristoyl phosphatidylglycerol and dipalmitoyl phosphatidylglycerol. The art also describes that the negative charged liposomes, due to their electrostatic properties, are less stable than neutral and positive liposomes when injected into the blood circulation. Anionic liposomes rapidly interact with the biological system subsequently to their opsonization with complement and other circulating proteins. Cationic liposomes first described in 1987 by Felgner et al. are typically used for gene delivery, based on the electrostatics between positively charged lipids and negatively charged nucleic acids (See, e.g., Felgner P, et al., Proc Natl Acad Sci USA. 1987; 84:7413-7417). They consist of natural neutral phospholipids and positively charged lipids. Commonly used neutral phospholipids include dioleoyl phosphatidylethanolamine (DOPE) or dioleoyl phosphatidylcholine, and are in most cases required for the stabilization of the liposome/DNA complex.

A variety of liposomal formulations with a positive charge are available in the marketplace such as DC-cholesterol HCl, (3β-[N—(N',N'-dimethylaminoethane)-carbamyl]cholesterol hydrochloride), DOTAP (1,2-dioleoyl-3-trimethylammonium-propane [chloride salt]), DOBAQ (N-[4-carboxybenzyl]-N,N-dimethyl-2,3-bis(oleoyloxy) propan-1-aminium), DDAB (dimethyldioctadecylammonium [bromide salt]), and MLVS (N1-[2-((1S)-1-[(3-aminopropyl) amino]-4-[di(3-amino-propyl)amino]butylcarboxamido) ethyl]-3,4-di[oleyloxy]-benzamide), and many others are under development. [Allen, T, et al. Advanced Drug Delivery Reviews 65(1), 2013, 36-48.].

The present invention provides compositions comprising emulsion adjuvant and one or more active agents or substances formulated for infusion or injection into a subject (e.g., using a syringe and needle), as well as methods of formulating and using the same (e.g., as an injectable medicinal composition (e.g., a vaccine)). The emulsion adjuvant of an immunogenic composition of the invention in its preferred form comprises a cationic lipid containing a polar head group and a hydrophobic component (e.g., a dual chain hydrophobic group (e.g., the cationic surfactant dioctadecyl dimethyl ammonium chloride (DODAC) and dioctadecyl dimethyl ammonium bromine (DODAB)). Compositions of the invention comprising emulsion adjuvant and one or more active agents or substances formulated for administration via injection to a subject find use in treatment and/or prevention of infectious disease, cancer and/or allergy.

Experiments conducted during development of embodiments of the invention have identified and characterized new emulsion compositions (e.g., adjuvant compositions) containing a cationic lipid possessing a relatively small polar head group (e.g., compared to a polar head group found on other cationic surfactants (e.g., cetylpyridinium chloride (CPC)) and that also possesses a dual chain hydrophobic component (e.g., two or more lipophilic side chains (e.g., that are attached to the polar head group))) and methods of using the same. For example, emulsion compositions (e.g., adjuvant compositions) containing a cationic lipid possessing a relatively small polar head group and a dual chain hydrophobic component (e.g., two or more lipophilic side chains (e.g., that are attached to the polar head group))) described herein were discovered to be surprisingly efficacious at inducing robust immune responses when administered via injection (e.g., intramuscularly) but failed to induce the same when administered via mucosal route (e.g., intranasally) (See, e.g., Examples 1-4).

Experiments conducted during development of embodiments of the invention identified a surprising, dominant role for cationic lipid in the biological activity of a variety of nanoemulsions manufactured and assessed by high-throughput screening (See, e.g., Examples 1-4). For example, nanoemulsions formulated using a cationic lipid possessing a small polar head group and a dual chain hydrophobic component (e.g., two or more lipophilic side chains (e.g., that are attached to the polar head group (e.g., dioctadecyl dimethyl ammonium chloride (DODAC) or dioctadecyl dimethyl ammonium bromide (DODAB))) demonstrated a uniquely high antigen uptake into cells concomitant with very low cellular toxicity (50% inhibitory concentration, IC50, >0.5%) when compared to other nanoemulsion formulations including nanoemulsions containing the cationic surfactant cetyl pyridinium chloride (CPC) (See Example 1).

Nanoemulsions formulated with a cationic surfactant containing a large polar head group (e.g., $W_{80}5EC$ formulated using cetylpyridinium chloride (CPC) as the cationic surfactant) were characterized by comparatively higher cell cytotoxicity (IC50<0.01) than nanoemulsions formulated with cationic surfactant containing a small polar head group and a dual chain hydrophobic component (e.g., DODAC formulations), low or intermediate uptake of antigen into epithelial or dendritic cells in screening assays in vitro, and strong induction in vivo of humoral and cellular immune responses (Th1, Th2 and Th17) when evaluated via the intranasal route of vaccine administration. In sharp contrast, nanoemulsions formulated with a cationic surfactant possessing a small polar head group and a dual chain hydrophobic component (e.g., two or more lipophilic side chains (e.g., that are attached to the polar head group)) display comparatively low cell cytotoxicity, activate low Th1 and Th2 cell-mediated immune responses without induction of Th17-type immunity, and generally provide poor adjuvant activity when administered by the intranasal route.

Although nanoemulsions formulated with a cationic surfactant possessing a small polar head group and a dual hydrophobic chain tail group (e.g., the cationic surfactant dioctadecyl dimethyl ammonium chloride (DODAC) and dioctadecyl dimethyl ammonium bromine (DODAB)) were characterized as being poor/suboptimal as intranasal adjuvants, additional experiments conducted during development of embodiments of the invention identified these formulations and being surprising robust immune stimulators when administered via injection (See Examples 1-4). In particular, and quite unexpectedly, the present invention provides emulsion formulations that did not meet minimal requirements for being useful as an adjuvant for mucosal (e.g., intranasal) administration that displayed surprisingly robust adjuvant activity when used as an adjuvant for injectable administration.

For example, in one embodiment, the invention provides immunogenic compositions containing an antigen and an emulsion formulated with a cationic lipid containing a small polar head group and a dual chain hydrophobic component (e.g., two or more lipophilic side chains (e.g., that are attached to the polar head group)) that displays significantly higher efficacy for induction of functional and protective immune responses (e.g., antigen-specific antibody responses and/or Th1 cellular immune responses) when administered via injection (e.g., via intramuscular injection) compared both to positive controls specific for the antigen (e.g., alum based positive controls) as well as compared to immunogenic compositions containing emulsion formulated with other cationic surfactants lacking a small polar head group and a dual chain hydrophobic component (e.g., two or more lipophilic side chains (e.g., that are attached to the polar head group (e.g., CPC that has a large polar head group and absence of dual chain hydrophobic component (See, e.g., Examples 1-4)))). In another embodiment, the invention provides immunogenic compositions containing an antigen and an emulsion formulated with a cationic lipid containing a small polar head group and a dual chain hydrophobic component (e.g., two or more lipophilic side chains (e.g., that are attached to the polar head group)) that displays significantly higher efficacy for induction of functional and protective immune responses (e.g., antigen-specific antibody responses and/or Th1 cellular immune responses) when administered via injection (e.g., via intramuscular injection) compared the same immunogenic composition when administered via a mucosal route (e.g., intranasally (e.g., that produces little to no functional and/or protective immune response)).

For example, in one embodiment, the invention provides an immunogenic composition containing an respiratory syncytial virus (RSV) antigen (e.g., recombinant F protein of RSV) and emulsion formulated with a cationic lipid with a small polar head group and a dual chain hydrophobic component (e.g., two or more lipophilic side chains (e.g., that are attached to the polar head group)) that induces a significantly higher induction of functional and protective RSV-specific antibody responses and Th1 cell mediated immune responses when administered via injection (e.g., via intramuscular injection) compared both to an alum based positive control as well as to an immunogenic compositions containing emulsion formulated with CPC (large polar head group and absence of dual chain hydrophobic component) (See, e.g., Example 2).

In another embodiment, the invention provides that immunogenic compositions containing emulsion formulated with a cationic lipid with a small polar head group and a dual chain hydrophobic component (e.g., two or more lipophilic side chains (e.g., that are attached to the polar head group (e.g., DODAC)))) display significant efficacy for induction of functional and protective antibody responses when administered via injection (e.g., via intramuscular injection) whereas immunogenic compositions containing emulsion formulated with CPC (large polar head group and absence of dual chain hydrophobic component) fail to display significant efficacy when administered via injection (e.g., intramuscular route) (See, e.g., Example 3).

For example, in one embodiment, the invention provides an immunogenic composition containing an influenza virus antigen (e.g., recombinant H5 hemagglutinin protein (rH5) influenza vaccine) and emulsion formulated with a cationic lipid with a small polar head group and a dual chain hydrophobic component (e.g., two or more lipophilic side chains (e.g., that are attached to the polar head group)) that induces a significantly higher induction of functional and protective influenza-specific antibody responses and Th1 cell mediated immune responses when administered via injection (e.g., via intramuscular injection) compared to an immunogenic compositions containing emulsion formulated with CPC ($W_{80}5EC$, CPC having a large polar head group and absence of dual chain hydrophobic component) (See, e.g., Example 3). Thus, the invention identifies and provides immunogenic compositions containing emulsion formulated with a small polar head groups and a dual chain hydrophobic component as a significantly efficacious emulsion-based vaccine (e.g., formulated for injectable administration (e.g., against H5 pandemic influenza (See, e.g., Example 3)).

Additionally, the invention provides, in one embodiment, that the addition of a cationic lipid (e.g. cationic lipid with a small polar head group and a dual chain hydrophobic component (e.g., two or more lipophilic side chains (e.g., that are attached to the polar head group)) to an immunogenic composition comprising a nanoemulsion formulated without the cationic lipid that is not effective at inducing robust immune responses when administered via injection transforms the immunogenic composition into one that is useful for injectable administration (See, e.g., Example 4). For example, the presence of at least one cationic lipid/surfactant containing a polar head and a dual chain hydrophobic component (e.g., two or more lipophilic side chains (e.g., that are attached to the polar head group)) within an emulsion of an immunogenic composition was sufficient and required to obtain significant and robust immune responses to an antigenic component of the immunogenic composition when administered to a subject via injection (See Example 4).

The invention is not limited by the type of cationic lipid utilized in an emulsion and/or composition (e.g. immunogenic composition (e.g. vaccine)) formulated for injectable administration. Multiple lipophilic side chain amphiphilic substances that have two or more lipophilic side chains (e.g., attached to a polar head group) may be used. Such lipids may be nonionic, cationic, anionic, or zwitterionic in nature. Examples of suitable multiple lipophilic side chain amphiphilic substances include, but are not limited to, saturated or unsaturated fatty acid chains (e.g., side chains having from about 8 to about 30 carbon atoms). Examples of cationic dual chain lipids/surfactants include, but are not limited to, dioctadecyldimethylammonium chloride (DODAC); di(s-oyoylethyl) hydroxyethylmonium methosulfate (DSHM); N—[I-(2,3-dioleyloxy)propyl]-N,N,N-trimethylammonium bromide (DOTMA); 1,2-dimyristyloxypropyl-N,N-dimethyl-hydroxyethyl ammonium bromide (DMRIE); [N—(N,N'-dimethylaminoethane)carbamoyl]cholesterol (DC-Chol); dioctadecylamidoglycyl spermidine (DOGS); dimethyl dioctadecylammonium bromide (DDAB); dioleoyl phosphatidylethanolamine (DOPE); 2,3-dioleoyloxyl-N[2(sperminecarbozamide-O-ethyl]-N,N-dimethyl-propanaminium trifluoroacetate (DOSPA); I-[2-(oleoyloxy)-ethyl]-2-oleyl-3-(2-hydroxyethyl)imidazolinium chloride (DOTIM); 1,2-dioleoyloxy-3-(trimethylammonio)propane (DOTAP); 1,2-diacyl-3-trimethylammonium propane (TAP); 1,2-diacyl-3-dimethylammonium propane (DAP); quaternary dimethyldiacyl amines wherein the acyl groups have from about 8 carbon atoms to about 30 carbon atoms (such as from about 10 carbon atoms to about 24 carbon atoms), fatty acid salts of quaternary amines such as dicocodimonium chloride (Quaternium 34), and quaternary dimethyldiacyl amines wherein the acyl groups have from about 8 carbon atoms to about 30 carbon atoms (e.g., from about 10 carbon atoms to about 30 carbon atoms), and derivatives thereof such as ammonium derivatives, i.e. dimethyl dihydrogenated tallow ammonium chloride (Quaternium 18), and decyl dimethyl octyl ammonium chloride (Quaternium 24), and derivatives thereof. Other cationic dual chain lipids/surfactants may be used (See, e.g., Fasbender et al., 269 *Am J Physiol* L45-L5 1 (1995); Solodin et al., 34 *Biochemistry* 13537-13544 (1995); Feigner et al., 269 *J Biol Chem* 2550-2561(1994); Stamatatos et al., 27 *Biochemistry* 3917-3925 (1988); and Leventis and Silvius, 1023 *Biochim Biophys Acta* 124-132 (1990), and Jouani et al., 9 J. Liposome Research 95-114 (1999), each of which is hereby incorporated by reference in its entirety).

Several of these cationic dual chain lipids, such as TAP and DAP, may possess a variety of types of chain groups having carbon atom to number of saturated bonds ratios of, for example, 14:0, 16:0, 18:0, and 18:1, as well as a variety of types of acyl groups having from about 10 carbon atoms to about 18 carbon atoms such as dimyristoyl, dipalmitoyl, distearoyl, and dioleoyl. The invention is not limited by the amount of dual chain lipids/surfactant in an emulsion and may range from, based upon the total weight of the composition, from about 0.1 percent to about 95 percent (such as from about 10 percent to about 65 percent).

Emulsions of the invention are formed by emulsification of an oil, purified water, nonionic detergent, organic solvent and surfactant, such as a cationic surfactant and/or cationic lipid (See, e.g., Example 1). In a preferred embodiment, all components of emulsion compositions of the invention are included on the FDA list of approved inactive ingredients for Approved Drug Products. The constituents (w/w %) of two emulsions are provided in the table below.

| Ingredients | 60% $W_{80}5EC$ | 60% DODAC NE |
|---|---|---|
| Purified Water, USP | 54.10% | 54.10% |
| Soybean Oil, USP | 37.67% | 37.67% |
| Dehydrated Alcohol, USP (anhydrous ethanol) | 4.04% | 4.04% |
| Polysorbate 80, NF | 3.55% | 3.55% |
| Cetylpyridinium Chloride (CPC), USP | 0.64% | — |
| Dioctadecyldimethylammonium chloride (DODAC) | — | 0.64% |

For the purposes of the present disclosure, a nanoemulsion as provided here (e.g. $W_{80}5EC$ or DODAC NE) can make up between 1-99% (w/w %) of an injectable composition (e.g., an immunogenic composition (e.g., a vaccine)) of the invention. For instance, the nanoemulsion can be about 1, about 5, about 10, about 15, about 20, about 25, about 30, about 35, about 40, about 45, about 50, about 55, about 60, about 65, about 70, about 75, about 80, about 85, about 90, about 95, or about 99% of an injectable composition (e.g., an immunogenic composition (e.g., a vaccine)) of the invention.

Methods of manufacture. The nanoemulsion adjuvants of the invention can be formed using classic emulsion forming techniques (See e.g., U.S. Pat. Pub. No. 2004/0043041). In an exemplary method, the oil is mixed with the aqueous phase under relatively high shear forces (e.g., using high hydraulic and mechanical forces) to obtain a nanoemulsion comprising oil droplets having an average diameter of less than about 1000 nm, although larger (greater than 1000 nm) droplets may be used. I some embodiments, a nanoemulsion has an oil phase comprising an alcohol (e.g., ethanol, methanol, glycerol, etc.). The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, each of which is hereby incorporated by reference in its entirety.

In an exemplary embodiment, the nanoemulsions used in the methods and compositions of the disclosed comprise droplets of an oily discontinuous phase dispersed in an aqueous continuous phase, such as water or PBS. Nanoemulsions of the invention are stable, and do not deteriorate even after long storage periods (See Example 1). In a preferred embodiment, nanoemulsions of the invention remain stable after a sterilization technique (e.g., autoclaving). Preferred nanoemulsions of the invention are non-toxic and safe when swallowed, inhaled, or contacted to the skin of a subject.

In further preferred embodiments, vaccine compositions of the invention (e.g., comprising emulsions formulated for injection of the invention) are produced in large quantities and are stable for many months at a broad range of temperatures. The nanoemulsion adjuvants can have any textures suitable for injectable administration including, but not limited to, that of a liquid. In one embodiment, at least a portion of the emulsion is in the form of lipid structures including, but not limited to, unilamellar, multilamellar, and pauciamellar lipid vesicles, micelles, and lamellar phases.

The present disclosure contemplates that many variations of the described vaccines will be useful in the methods of the present disclosure. To determine if a candidate vaccine is suitable for use with the present disclosure, three criteria are analyzed. Using the methods and standards described herein, candidate vaccines can be easily tested to determine if they are suitable. First, the desired ingredients are prepared using the methods described herein, to determine if a vaccine can be formed. If a vaccine cannot be formed, the candidate is rejected. Second, the candidate vaccine should be stable; e.g., if the vaccine is a nanoemulsion vaccine, then the nanoemulsion should be stable. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate vaccines should have efficacy for its intended use. For example, the vaccines of the invention should induce a protective immune response to a detectable level when administered via injection.

Compositions of the invention can be provided in many different types of containers and delivery systems. For example, in one embodiment, a composition of the invention (e.g., an immunogenic composition formulated for administration via injection comprising an oil in water emulsion comprising a cationic lipid containing a polar head group and a dual chain hydrophobic group, a non-ionic surfactant, an organic solvent, oil and water; and an antigen) is provided in a syringe. Compositions can be delivered (e.g., to a subject or customers) in any suitable container. Suitable containers can be used that provide one or more single use or multi-use dosages of the compositions (e.g., vaccines) for the desired application. Containers can be packaged with instructions for use to form kits.

Accordingly, in one embodiment, the present invention provides methods and compositions for the stimulation of immune responses and for treating or preventing disease. In particular, the present invention provides nanoemulsion compositions formulated for administration via injection and methods of using the same for the induction of immune responses (e.g. protective and/or therapeutic cellular and/or humoral immune responses).

Accordingly, in a preferred embodiment, the invention provides a method for treating and/or preventing a disease in a subject comprising administering to the subject a therapeutically effective amount of a vaccine comprising an emulsion formulated for administration via injection.

In one embodiment, a vaccine comprising an emulsion formulated for administration via injection is used to modulate (e.g., reduce or skew away from) Th2 immune responses (e.g., underling allergic disease) and promote Th1/Th17 immunity (e.g., skew towards a Th1 type immune response and/or a more balanced Th1/Th2 immune response) as a therapeutic for allergic disease, inflammatory disease, or any other disease associated with Th2 immunity. The invention is not limited to any particular allergic disease. Indeed, compositions and methods of the invention may be utilized to prevent and/or treat a variety of allergic diseases including but not limited to asthma, respiratory allergy (e.g., pollen allergy), stinging insect allergy, allergic rhinitis (hay fever), food allergy, drug allergy, latex allergy, atopic dermatitis (eczema), or other allergic disease known in the art. In one embodiment, the invention provides methods of modulating existing Th2 immune responses with a mucosal nanoemulsion-based vaccine (e.g., vaccinate a subject against a certain allergy (e.g., a peanut allergy)). This means that a vaccine comprising an emulsion formulated for administration via injection can be used to vaccinate people against allergies (e.g., peanut, etc.). In another embodiment, the invention provides the ability to redirect Th2-polarized immune responses in a subject (e.g., in a subject with Th2 mediated disease) toward a Th1-type immune response (e.g., skew toward a Th1 type immune response and/or generate a more balanced Th1/Th2 type immune response) via administering via injection to the subject to (e.g., nasally administering) a vaccine comprising an emulsion formulated for administration via injection.

In another embodiment, the invention provides a method for treating and/or preventing an infectious disease in a subject comprising administering to the subject a therapeutically effective amount of a vaccine comprising an emulsion formulated for administration via injection. In some embodiments, a composition of the invention (e.g., a vaccine comprising an emulsion formulated for administration via injection) induces (e.g., when administered to a subject) both systemic and mucosal immune responses (e.g., generates systemic and or mucosal immunity (e.g., thereby reducing or preventing signs, symptoms or conditions of infectious disease)). Thus, in some embodiments, administration of a composition of the present invention to a subject results in protection against an exposure to one or a plurality pathogens (e.g., pathogenic bacteria, pathogenic virus, pathogenic fungi, etc.).

Nanoemulsion compositions utilized in some embodiments of the present invention, in contrast to other nanoemulsions known in the art, demonstrate little to no anti-pathogen effect (e.g., killing and/or prohibiting growth of a pathogen). For example, in one embodiment, an emulsion formulated with a cationic lipid containing a small polar head group and a dual chain hydrophobic component (e.g., two or more lipophilic side chains (e.g., that are attached to the polar head group)) displays little to no ability to inactivate bacteria (both vegetative and spore forms), virus, and fungi.

In some embodiments, the present invention provides compositions for inducing immune responses comprising an emulsion formulated with a cationic lipid containing a small polar head group and a dual chain hydrophobic component (e.g., two or more lipophilic side chains (e.g., that are attached to the polar head group)) and one or more immunogens (e.g., one or more antigens, inactivated microbial pathogens and/or pathogen products, peptides, proteins, glycoproteins lipoproteins, glycopeptides, lipopeptides, toxoids, carbohydrates, tumor-specific antigens) and/or one or more allergens, allergenic substance or other material that causes an allergic response.

Immunogenic compositions (e.g., vaccines) comprising emulsions formulated with a cationic lipid containing a small polar head group and a dual chain hydrophobic component (e.g., two or more lipophilic side chains (e.g., that are attached to the polar head group)) of the present invention may be combined in any suitable amount utilizing a variety of delivery methods. Any suitable pharmaceutical formulation may be utilized, including, but not limited to, those disclosed herein. Suitable formulations may be tested for immunogenicity using any suitable method. For example, in some embodiments, immunogenicity is investigated by quantitating both specific T-cell responses (e.g., cytokine profiles) and antibody titer. Immunogenic compositions of the present invention may also be tested in animal models of infectious disease states. Suitable animal models, pathogens, and assays for immunogenicity include, but are not limited to, those described herein.

In some embodiments, the present invention provides methods of inducing an immune response and compositions useful in such methods (e.g., a nanoemulsion adjuvant composition). In some embodiments, methods of inducing an immune response in a host subject provided by the present invention are used for vaccination. For example, in some embodiments, the present invention provides a composition comprising a nanoemulsion adjuvant and one or a plurality of immunogens (e.g., derived from a plurality of pathogens (e.g., one or a plurality of pathogens inactivated by a nanoemulsion of the present invention and/or one or a plurality of protein and/or peptide antigens derived from (e.g., isolated and/or recombinantly produced from) one or a plurality of pathogens)); as well as methods of administering the composition (e.g., via injection) to a subject under conditions such that the subject generates an immune response to the one or a plurality of pathogens and/or immunogens. In some embodiments, inducing an immune response induces immunity to one or a plurality of immunogens in the subject. In some embodiments, immunity comprises systemic immunity. In some embodiments, immunity comprises mucosal immunity. In some embodiments, the immune response comprises a systemic IgG response to the immunogens. In some embodiments, the immune response comprises a mucosal IgA response to the immunogens. In some embodiments, the immune response is characterized by a balanced Th1/Th2 polarization (e.g., an IgG subclass distribution and cytokine response indicative of a balanced Th1/Th2 response).

Thus, as described herein, the present invention, in one embodiment, provides adjuvant mixtures useful for formulating immunogenic compositions, suitable to be used as, for example, vaccines. As described in Examples 1-4, the immunogenic composition elicits an immune response by the host (e.g., host cells) to which it is administered (e.g., including the production of cytokines and other immune factors). In some embodiments, an adjuvant composition is formulated to include at least one antigen (e.g., pathogenic antigen or allergic antigen). An antigen may be an inactivated pathogen or an antigenic fraction of a pathogen, or an allergen, allergenic substance or other material that causes an allergic response. The pathogen may be, for example, a virus, a bacterium or a parasite. The pathogen may be inactivated by a chemical agent, such as formaldehyde, glutaraldehyde, beta-propiolactone, ethyleneimine and derivatives, or other compounds. The pathogen may also be inactivated by a physical agent, such as UV radiation, gamma radiation, "heat shock" and X-ray radiation. An antigenic fraction of a pathogen can be produced by means of chemical or physical decomposition methods, followed, if desired, by separation of a fraction by means of chromatography, centrifugation and similar techniques. Alternatively, antigens or haptens can be prepared by means of organic synthetic methods, or, in the case of, for example, polypeptides and proteins, by means of recombinant DNA methods. In some embodiments, an adjuvant composition of the invention is co-administered with a vaccine available in the marketplace (e.g., in order to generate a more robust immune response, in order to skew the immune response (e.g., toward a Th1 and away from a Th2 response) or to balance the type of immune response elicited by the vaccine).

The present invention is not limited by the type of nanoemulsion adjuvant that is benefited by inclusion of or addition of a cationic lipid (e.g. cationic lipid with a small polar head group and a dual chain hydrophobic component (e.g., two or more lipophilic side chains (e.g., that are attached to the polar head group)) described herein.

For example, in some embodiments, a nanoemulsion comprising (i) an aqueous phase; (ii) an oil phase; and at least one additional compound is benefited by inclusion of or addition of a cationic lipid (e.g. cationic lipid with a small polar head group and a dual chain hydrophobic component (e.g., two or more lipophilic side chains (e.g., that are attached to the polar head group)) described herein. In some embodiments of the present invention, a cationic lipid is admixed into either the aqueous or oil phases of the composition. In other embodiments, a cationic lipid is admixed into a composition of previously emulsified oil and aqueous phases. In certain of these embodiments, a cationic lipid and/or one or more additional compounds are admixed into an existing emulsion composition immediately prior to its use. In other embodiments, a cationic lipid and/or one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweeteners, bulking agents, and the like) and pharmaceutically acceptable compounds (e.g., carriers). Certain exemplary embodiments of the various compounds contemplated for use in the compositions of the present invention are described herein. Unless described otherwise, nanoemulsions are described in undiluted form.

Nanoemulsion adjuvant compositions are not limited to any particular nanoemulsion. Any number of suitable nanoemulsion compositions may be utilized in the vaccine compositions of the present invention, including, but not limited to, those disclosed in Hamouda et al., J. Infect Dis., 180: 1939 (1999); Hamouda and Baker, J. Appl. Microbiol., 89:397 (2000); and Donovan et al., Antivir. Chem. Chemother., 11:41 (2000). Preferred nanoemulsions of the present invention are those that are non-toxic to animals. In preferred embodiments, nanoemulsions utilized in the methods of the present invention are stable, and do not decompose even after long storage periods (e.g., one or more years). Additionally, preferred emulsions maintain stability even after exposure to high temperature and freezing. This is especially useful if they are to be applied in extreme conditions (e.g., extreme heat or cold).

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Nanoemulsions formulated for administration via injection

As described herein, experiments conducted during development of embodiments of the invention identified certain, specific nanoemulsion formulations that lacked useful adjuvant activity when used for mucosal (e.g., intranasal) administration but that, unexpectedly, provided surprisingly robust and highly beneficial adjuvant activity when administered via injection (e.g., intramuscularly) (See, e.g., Examples 1-5). Specific nanoemulsion formulations falling into this category include, but are not limited to, nanoemulsions comprising a cationic lipid described herein.

Emulsion formulations for administration via injection described herein are simply examples to illustrate the variety of nanoemulsion adjuvants that find use in the present invention. The present invention contemplates that many variations of the these formulations, as well as additional nanoemulsions, find use in the methods of the present invention. Candidate emulsions can be easily tested to determine if they are suitable of injectable administration (e.g., versus mucosal (e.g., intranasal) administration.

In preferred embodiments of the present invention, emulsion formulations for administration via injection are non-toxic (e.g., to humans, plants, or animals), non-irritant (e.g., to humans, plants, or animals), and non-corrosive (e.g., to humans, plants, or animals or the environment), while retaining stability when mixed with other agents (e.g., a composition comprising an immunogen (e.g., bacteria, fungi, viruses, and spores).

In some embodiments, emulsion formulations for administration via injection comprise surfactant lipid preparations (SLPs) for use as broad-spectrum antimicrobial agents that are effective against bacteria and their spores, enveloped viruses, and fungi. In preferred embodiments, these SLPs comprise a mixture of oils, detergents, solvents, and cationic halogen-containing compounds in addition to several ions that enhance their biocidal activities. These SLPs are characterized as stable, non-irritant, and non-toxic compounds compared to commercially available bactericidal and sporicidal agents, which are highly irritant and/or toxic.

Ingredients for use in the non-toxic nanoemulsions include, but are not limited to: detergents (e.g., TRITON X-100 (5-15%) or other members of the TRITON family, TWEEN 60 (0.5-2%) or other members of the TWEEN family, or TYLOXAPOL (1-10%)); solvents (e.g., tributyl phosphate (5-15%)); alcohols (e.g., ethanol (5-15%) or glycerol (5-15%)); oils (e.g., soybean oil (40-70%)); cationic halogen-containing compounds (e.g., cetylpyridinium chloride (0.5-2%), cetylpyridinium bromide (0.5-2%)), or cetyldimethylethyl ammonium bromide (0.5-2%)); quaternary ammonium compounds (e.g., benzalkonium chloride (0.5-2%), N-alkyldimethylbenzyl ammonium chloride (0.5-2%)); ions (calcium chloride (1 mM-40 mM), ammonium chloride (1 mM-20 mM), sodium chloride (5 mM-200 mM), sodium phosphate (1 mM-20 mM)); nucleosides (e.g., inosine (50 μM-20 mM)); and amino acids (e.g., L-alanine (50 μM-20 mM)).

Quaternary ammonium compounds for use in the invention include, but are not limited to, N-alkyldimethyl benzyl ammonium saccharinate; 1,3,5-Triazine-1,3,5(2H,4H,6H)-triethanol; 1-Decanaminium, N-decyl-N, N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxethyl)-2-imidazolinium chloride; alkyl bis(2-hydroxyethyl) benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis (2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-tris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

1. Aqueous Phase

In some embodiments, the emulsion comprises an aqueous phase. In certain preferred embodiments, the emulsion comprises about 5 to 50, preferably 10 to 40, more preferably 15 to 30, vol. % aqueous phase, based on the total volume of the emulsion (although other concentrations are also contemplated). In preferred embodiments, the aqueous phase comprises water at a pH of about 4 to 10, preferably about 6 to 8. The water is preferably deionized (hereinafter "$DiH_2O$"). In some embodiments, the aqueous phase comprises phosphate buffered saline (PBS). In some preferred embodiments, the aqueous phase is sterile and pyrogen free.

2. Oil Phase

In some embodiments, the emulsion comprises an oil phase. In certain preferred embodiments, the oil phase (e.g., carrier oil) of the emulsion of the present invention comprises 30-90, preferably 60-80, and more preferably 60-70, vol. % of oil, based on the total volume of the emulsion (although higher and lower concentrations also find use in emulsions described herein).

The oil in the nanoemulsion adjuvant of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, *sassafras* Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, *chenopodium* oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

Organic Solvent

In some embodiments, the oil phase comprises 3-15, and preferably 5-10 vol. % of an organic solvent, based on the total volume of the emulsion. While the present invention is not limited to any particular mechanism, it is contemplated that the organic phosphate-based solvents employed in the emulsions serve to remove or disrupt the lipids in the membranes of the pathogens. Thus, any solvent that removes the sterols or phospholipids in the microbial membranes finds use in the methods of the present invention. Suitable organic solvents include, but are not limited to, organic phosphate based solvents or alcohols. In some preferred embodiments, non-toxic alcohols (e.g., ethanol) are used as a solvent. The oil phase, and any additional compounds provided in the oil phase, are preferably sterile and pyrogen free.

3. Surfactants and Detergents

In some embodiments, emulsion formulations for administration via injection further comprises a surfactant or detergent. In some preferred embodiments, the emulsion comprises from about 3 to 15%, and preferably about 10% of one or more surfactants or detergents (although other concentrations are also contemplated). While the present invention is not limited to any particular mechanism, it is contemplated that surfactants, when present in the emulsions, help to stabilize the emulsions. Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers.

The surfactant in the nanoemulsion adjuvant of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference. Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thiglycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isopropyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5-(OCH_2CH_2)_y-OH$, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23. In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis(imidazoyl carbonyl)), nonoxynol-9, Bis(polyethylene glycol bis(imidazoyl carbonyl)), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quaternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-Triazine-1,3,5(2H,4H,6H)-triethanol, 1-Decanaminium, N-decyl-N,N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Alkyl 1 or 3 benzyl-1-(2-hydroxethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl dimethyl benzyl ammonium chloride, Alkyl didecyl dimethyl ammonium chloride, Alkyl dimethyl benzyl ammonium chloride, Alkyl dimethyl benzyl ammonium chloride (C12-16), Alkyl dimethyl benzyl ammonium chloride (C12-18), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 30% C14, 17% C16, 3% C18), Alkyl trimethyl ammonium chloride (58% C18, 40% C16, 1% C14, 1% C12), Alkyl trimethyl ammonium chloride (90% C18, 10% C16), Alkyldimethyl(ethylbenzyl) ammonium chloride (C12-18), Di-(C8-10)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio) propanesulfonate, 3-(N,N-Dimethyloctadecylammonio)propanesulfonate, 3-(N,N-Dimethyloctylammonio) propanesulfonate inner salt, 3-(N,N-Dimethylpalmitylammonio)propanesulfonate, semi-synthetic derivatives thereof, and combinations thereof.

The present invention is not limited to the surfactants disclosed herein. Additional surfactants and detergents useful in the compositions of the present invention may be ascertained from reference works (e.g., including, but not limited to, McCutheon's Volume 1: Emulsions and Detergents—North American Edition, 2000) and commercial sources.

4. Cationic Halogens Containing Compounds

In some embodiments, the emulsions further comprise a cationic halogen containing compound. In some preferred embodiments, the emulsion comprises from about 0.5 to 1.0 wt. % or more of a cationic halogen containing compound, based on the total weight of the emulsion (although other concentrations are also contemplated). In preferred embodiments, the cationic halogen-containing compound is preferably premixed with the oil phase; however, it should be understood that the cationic halogen-containing compound may be provided in combination with the emulsion composition in a distinct formulation. Suitable halogen containing compounds may be selected from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), and cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen-containing compound is CPC, although the compositions of the present invention are not limited to formulation with any particular cationic containing compound.

5. Germination Enhancers

In other embodiments of the present invention, the nanoemulsions further comprise a germination enhancer. In some preferred embodiments, the emulsions comprise from about 1 mM to 15 mM, and more preferably from about 5 mM to 10 mM of one or more germination enhancing compounds (although other concentrations are also contemplated). In preferred embodiments, the germination enhancing compound is provided in the aqueous phase prior to formation of the emulsion. The present invention contemplates that when germination enhancers are added to the nanoemulsion compositions, the sporicidal properties of the nanoemulsions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the nanoemulsion preferentially occurs when the spores initiate germination.

In specific embodiments, it has been demonstrated that the emulsions utilized in the vaccines of the present invention have sporicidal activity. While the present invention is not limited to any particular mechanism and an understanding of the mechanism is not required to practice the present invention, it is believed that the fusigenic component of the emulsions acts to initiate germination and before reversion to the vegetative form is complete the lysogenic component of the emulsion acts to lyse the newly germinating spore. These components of the emulsion thus act in concert to leave the spore susceptible to disruption by the emulsions. The addition of germination enhancer further facilitates the anti-sporicidal activity of the emulsions, for example, by speeding up the rate at which the sporicidal activity occurs.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine stimulates bacterial spore germination (See e.g., Hills, J. Gen. Micro. 4:38 (1950); and Halvorson and Church, Bacteriol Rev. 21:112 (1957)). L-alanine and L-proline have also been reported to initiate fungal spore germination (Yanagita, Arch Mikrobiol 26:329 (1957)). Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate, which is the end product of glycolytic metabolism (Embden-Meyerhof Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle), which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

In certain embodiments, suitable germination enhancing agents of the invention include, but are not limited to, α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104; herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the nanoemulsions utilized in some embodiments of the present invention. A candidate germination enhancer should meet two criteria for inclusion in the compositions of the present invention: it should be capable of being associated with the emulsions disclosed herein and it should increase the rate of germination of a target spore when incorporated in the emulsions disclosed herein. One skilled in the art can determine whether a particular agent has the desired function of acting as an germination enhancer by applying such an agent in combination with the nanoemulsions disclosed herein to a target and comparing the inactivation of the target when contacted by the admixture with inactivation of like targets by the composition of the present invention without the agent. Any agent that increases germination, and thereby decreases or inhibits the growth of the organisms, is considered a suitable enhancer for use in the nanoemulsion compositions disclosed herein.

In still other embodiments, addition of a germination enhancer (or growth medium) to a neutral emulsion composition produces a composition that is useful in inactivating bacterial spores in addition to enveloped viruses, Gram negative bacteria, and Gram positive bacteria for use in the vaccine compositions of the present invention.

6. Interaction Enhancers

In still other embodiments, nanoemulsions comprise one or more compounds capable of increasing the interaction of the compositions (i.e., "interaction enhancer" (e.g., with target pathogens (e.g., the cell wall of Gram negative bacteria such as *Vibrio*, *Salmonella*, *Shigella* and *Pseudomonas*)). In preferred embodiments, the interaction enhancer is preferably premixed with the oil phase; however, in other embodiments the interaction enhancer is provided in combination with the compositions after emulsification. In certain preferred embodiments, the interaction enhancer is a chelating agent (e.g., ethylenediaminetetraacetic acid (EDTA) or ethylenebis (oxyethylenenitrilo)tetraacetic acid (EGTA) in a buffer (e.g., tris buffer)). It is understood that chelating agents are merely exemplary interaction enhancing compounds. Indeed, other agents that increase the interaction of the nanoemulsions used in some embodiments of the present invention (e.g., with microbial agents, pathogens, vaccines, etc.) are contemplated. In particularly preferred embodiments, the interaction enhancer is at a concentration of about 50 to about 250 μM. One skilled in the art will be able to determine whether a particular agent has the desired function of acting as an interaction enhancer by applying such an agent in combination with the compositions of the present invention to a target and comparing the inactivation of the target when contacted by the admixture with inactivation of like targets by the composition of the present invention without the agent. Any agent that increases the interaction of an emulsion with bacteria and thereby decreases or inhibits the growth of the bacteria, in comparison to that parameter in its absence, is considered an interaction enhancer.

In some embodiments, the addition of an interaction enhancer to nanoemulsion produces a composition that is useful in inactivating enveloped viruses, some Gram positive bacteria and some Gram negative bacteria for use in a vaccine composition.

7. Quaternary Ammonium Compounds

In some embodiments, nanoemulsions of the present invention include a quaternary ammonium containing compound. Exemplary quaternary ammonium compounds include, but are not limited to, Alkyl dimethyl benzyl ammonium chloride, didecyl dimethyl ammonium chloride, Alkyl dimethyl benzyl and dialkyl dimethyl ammonium chloride, N,N-Dimethyl-2-hydroxypropylammonium chloride polymer, Didecyl dimethyl ammonium chloride, n-Alkyl dimethyl benzyl ammonium chloride, n-Alkyl dimethyl ethylbenzyl ammonium chloride, Dialkyl dimethyl ammonium chloride, n-Alkyl dimethyl benzyl ammonium chloride, n-Tetradecyl dimethyl benzyl ammonium chloride monohydrate, n-Alkyl dimethyl benzyl ammonium chloride, Dialkyl dimethyl ammonium chloride, Hexahydro-1,3,5-tris (2-hydroxyethyl)-s-triazine, Myristalkonium chloride (and) Quat RNIUM 14, Alkyl bis(2-hydroxyethyl) benzyl ammonium chloride, Alkyl demethyl benzyl ammonium chloride, Alkyl dimethyl 3,4-dichlorobenzyl ammonium chloride, Alkyl dimethyl benzyl ammonium chloride, Alkyl dimethyl benzyl dimethylbenzyl ammonium, Alkyl dimethyl dimethybenzyl ammonium chloride, Alkyl dimethyl ethyl ammonium bromide, Alkyl dimethyl ethyl ammonium bromide, Alkyl dimethyl ethylbenzyl ammonium chloride, Alkyl dimethyl isopropylbenzyl ammonium chloride, Alkyl trimethyl ammonium chloride, Alkyl 1 or 3 benzyl-1-(2-hydroxethyl)-2-imidazolinium chloride, Dialkyl methyl benzyl ammonium chloride, Dialkyl dimethyl ammonium chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysilyl quats, and Trimethyl dodecylbenzyl ammonium chloride.

8. Other Components

In some embodiments, a nanoemulsion adjuvant composition comprises one or more additional components that provide a desired property or functionality to the nanoemulsions. These components may be incorporated into the aqueous phase or the oil phase of the nanoemulsions and/or may be added prior to or following emulsification. For example, in some embodiments, the nanoemulsions further comprise phenols (e.g., triclosan, phenyl phenol), acidifying agents (e.g., citric acid (e.g., 1.5-6%), acetic acid, lemon juice), alkylating agents (e.g., sodium hydroxide (e.g., 0.3%)), buffers (e.g., citrate buffer, acetate buffer, and other buffers useful to maintain a specific pH), and halogens (e.g., polyvinylpyrrolidone, sodium hypochlorite, hydrogen peroxide).

Exemplary techniques for making a nanoemulsion are described herein. Additionally, a number of specific, although exemplary, formulation recipes are also set forth herein.

In some embodiments, a nanoemulsion adjuvant is administered to a subject before, concurrent with or after administration of a composition comprising an immunogen (e.g., a pathogen and/or pathogen component (e.g., purified, isolated and/or recombinant pathogen peptide and/or protein)). The invention is not limited to the use of any one specific type of composition comprising an immunogen. Indeed, a variety of compositions comprising an immunogen (e.g., utilized for generating an immune response (e.g., for use as a vaccine)) may be utilized with a nanoemulsion adjuvant of the invention. In some embodiments, the composition comprising an immunogen comprises pathogens (e.g., killed pathogens), pathogen components or isolated, purified and/or recombinant parts thereof. Accordingly, in some embodiments, the composition comprising an immunogen comprises a bacterial pathogen or pathogen component including, but not limited to, *Bacillus cereus, Bacillus circulars* and *Bacillus megaterium, Bacillus anthraces*, bacteria of the genus *Brucella, Vibrio cholera, Coxiella burnetii, Francisella tularensis, Chlamydia psittaci, Ricinus communis, Rickettsia prowazekii*, bacterial of the genus *Salmonella* (e.g., *S. typhi*), bacteria of the genus *Shigella, Cryptosporidium parvum, Burkholderia pseudomallei, Clostridium perfringens, Clostridium botulinum, Vibrio cholerae, Streptococcus pyogenes, Streptococcus agalactiae, Streptococcus pneumonia, Staphylococcus aureus, Neisseria gonorrhea, Haemophilus influenzae, Escherichia coli, Salmonella typhimurium, Shigella dysenteriae, Proteus mirabilis, Pseudomonas aeruginosa, Yersinia pestis, Yersinia enterocolitica*, and *Yersinia pseudotuberculosis*). In other embodiments, the composition comprising an immunogen comprises a viral pathogen or pathogen component including, but not limited to, influenza A virus, avian influenza virus, H5N1 influenza virus, West Nile virus, SARS virus, Marburg virus, Arenaviruses, Nipah virus, alphaviruses, filoviruses, herpes simplex virus I, herpes simplex virus II, sendai, sindbis, vaccinia, parvovirus, human immunodeficiency virus, hepatitis B virus, hepatitis C virus, hepatitis A virus, cytomegalovirus, human papilloma virus, picornavirus, hantavirus, junin virus, and ebola virus). In still further embodiments, the composition comprising an immunogen comprises a fungal pathogen or pathogen component, including, but not limited to, *Candida albicnas* and *parapsilosis, Aspergillus fumigatus* and *niger, Fusarium* spp, *Trychophyton* spp.

In some embodiments, a nanoemulsion adjuvant is administered to a subject before, concurrent with or after administration of a vaccine containing peptides (e.g., one generally well known in the art, as exemplified by U.S. Pat. Nos. 4,601,903; 4,599,231; 4,599,230; and 4,596,792; each of which is hereby incorporated by reference).

Formulation Techniques

Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, and U.S. Patent Application Nos. 20070036831, 20060251684, and 20050208083, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen. In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucliamellar lipid vesicles, micelles, and lamellar phases.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years); they are non-irritant and non-toxic compared to their individual components due, at least in part, to their oil contents that markedly reduce the toxicity of the detergents and the solvents; they are effective at concentrations as low as, for example, 0.1%.

The present invention is not limited by the type of subject administered a composition of the present invention. The present invention is not limited by the particular formulation of a composition comprising a nanoemulsion adjuvant of the present invention. Indeed, a composition comprising a nanoemulsion of the present invention may comprise one or more different agents in addition to the nanoemulsion. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a nanoemulsion of the present invention comprises an agent and/or co-factor that enhance the ability of the nanoemulsion to induce an immune response. In some preferred embodiments, the presence of one or more co-factors or agents reduces the amount of nanoemulsion required for inducing an immune response. The present invention is not limited by the type of co-factor or agent used in a therapeutic agent of the present invention.

In some embodiments, a co-factor or agent used in a nanoemulsion composition is a bioactive agent. For example, in some embodiments, the bioactive agent may be a bioactive agent useful in a cell (e.g., a cell expressing a CFTR). Bioactive agents, as used herein, include diagnostic agents such as radioactive labels and fluorescent labels. Bioactive agents also include molecules affecting the metabolism of a cell (e.g., a cell expressing a CFTR), including peptides, nucleic acids, and other natural and synthetic drug molecules. Bioactive agents include, but are not limited to, adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LHRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; amyotrophic lateral sclerosis agent; cerebral ischemia agent; Paget's disease agent; unstable angina agent; uricosuric; vasoconstrictor; vasodilator; vulnerary; wound healing agent; xanthine oxidase inhibitor.

Molecules useful as antimicrobials can be delivered by the methods and compositions of the invention. Antibiotics that may find use in co-administration with a composition comprising a nanoemulsion of the present invention include, but are not limited to, agents or drugs that are bactericidal and/or bacteriostatic (e.g., inhibiting replication of bacteria or inhibiting synthesis of bacterial components required for survival of the infecting organism), including, but not limited to, almecillin, amdinocillin, amikacin, amoxicillin, amphomycin, amphotericin B, ampicillin, azacitidine, azaserine, azithromycin, azlocillin, aztreonam, bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveminomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786,392, MC-02479, PepS, RP 59500, and TD-6424.

In some embodiments, a composition comprising a nanoemulsion of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a nanoemulsion) enhances an immune response in a host subject due to an increase in duration and/or amount of exposure to the nanoemulsion that a subject experiences when a mucoadhesive is used compared to the duration and/or amount of exposure to the nanoemulsion in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, pulmonary, subcutaneous, intramuscular, intraperitoneal, intravenous, or administration via other routes may be found in Remington's Pharmaceutical Sciences, Mack Publishing Company, Easton, Pa.

A composition comprising a nanoemulsion adjuvant of the present invention can be used therapeutically or as a prophylactic. A composition comprising a nanoemulsion of the present invention can be administered to a subject via a number of different delivery routes and methods. Preferred routes of administration, as described herein, is via injection.

Injection (often referred to as a "shot" in US English, or a "jab" in UK English) is an infusion method of putting fluid into the body, usually with a syringe and a hollow needle which is pierced through the skin to a sufficient depth for the material to be administered into the body. An injection follows a parenteral route of administration; that is, administration via a route other than through the digestive tract. The process involves a small puncture wound to the body (with varying degrees of pain depending on injection type and location, medication type, needle gauge and the skill of the individual administering the injection). Preferred methods of injection or infusion include, but are not limited to, intradermal, subcutaneous, intramuscular, intravenous, intraosseous, intraperitoneal, intrathecal, epidural, intracardiac, intraarticular, intracavernous, and intravitreal. Rodents used for research are often administered intracerebral, intracerebroventricular, or intraportal injections as well.

Thus, in some embodiments, a composition comprising an emulsion of the present invention may be used to protect and/or treat a subject susceptible to, or suffering from, a disease by means of administering compositions comprising an emulsion via injection (e.g., via intradermal, subcutaneous, intramuscular, intravenous, intraosseous, intraperitoneal, intrathecal, epidural, intracardiac, intraarticular, intracavernous, and/or intravitreal route). Methods of systemic administration of the emulsion and/or agent co-administered with the emulsion may include conventional syringes and needles, or devices designed for ballistic delivery (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). In some embodiments, the present invention provides a delivery device for systemic administration, pre-filled with the emulsion composition of the present invention.

As described above, the present invention is not limited by the type of subject administered a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism or allergic substance or material. In some embodiments, the human subjects are subjects that are more likely to receive a direct exposure to pathogenic microorganisms or that are more likely to display signs and symptoms of disease after exposure to a pathogen (e.g., subjects with CF or asthma, subjects in the armed forces, government employees, frequent travelers, persons attending or working in a school or daycare, health care workers, an elderly person, an immunocompromised person, and emergency service employees (e.g., police, fire, EMT employees)). In some embodiments, any one or all members of the general public can be administered a composition of the present invention (e.g., to prevent the occurrence or spread of disease). For example, in some embodiments, compositions and methods of the present invention are utilized to treat a group of people (e.g., a population of a region, city, state and/or country) for their own health (e.g., to prevent or treat disease) and/or to prevent or reduce the risk of disease spread from animals (e.g., birds, cattle, sheep, pigs, etc.) to humans. In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

In some embodiments, a composition (e.g., vaccine) of the invention is administered to a subject with cancer. A subject may be one who has (e.g., that is clinically diagnosed (e.g., via biopsy, x-ray, blood test, etc.) as having) or that suspected of having cancer (e.g., of any stage or progression state (e.g., metastatic cancer)). In some embodiments, a subject administered a composition (e.g., vaccine) of the invention is a subject that has undergone surgery to remove cancer. In some embodiments, a subject administered a composition (e.g., vaccine) of the invention is a subject that is in remission. In some embodiments, a subject administered a composition (e.g., vaccine) of the invention is a subject that has one or more lymph nodes that test positive for cancer.

Immunogenic compositions of the invention comprising a emulsion formulated for administration via injection can be administered (e.g., to a subject) as a therapeutic or as a prophylactic to prevent microbial infection.

The compositions of the present invention may additionally contain other adjunct components conventionally found in pharmaceutical compositions. Thus, for example, the compositions may contain additional, compatible, pharmaceutically-active materials such as, for example, antipyruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the nanoemulsion. In some embodiments, nanoemulsion compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition of the invention is co-administered with one or more antibiotics. For example, one or more antibiotics may be administered with, before and/or after administration of a composition of the invention. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

A wide variety of antimicrobial agents are currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, ganciclovir, vidarabine, and acyclovir which act to inhibit viral enzymes essential for DNA synthesis. Various combinations of antimicrobials may be employed.

The present invention also includes methods involving co-administration of a composition comprising a emulsion adjuvant with one or more additional active and/or anti-infective agents. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, a second type of emulsion, etc.) can be any of the well-known agents in the art, including, but not limited to, those that are currently in clinical use.

In some embodiments, a composition comprising a emulsion is administered to a subject via more than one route. For example, a subject may benefit from receiving intradermal administration and, additionally, receiving one or more other routes of administration (e.g., intramuscular or other methods described herein).

In some embodiments, other delivery systems are used that can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

The present invention is not limited by the amount of emulsion used. The amount will vary depending upon which specific emulsion(s) is/are employed, and can vary from subject to subject, depending on a number of factors including, but not limited to, the species, age and general condition (e.g., health) of the subject, and the mode of administration. Procedures for determining the appropriate amount of emulsion administered to a subject to induce an immune response in a subject can be readily determined using known means by one of ordinary skill in the art.

In some embodiments, it is expected that each dose (e.g., of a composition comprising a emulsion comprises 1-95% emulsion, in some embodiments, 20% emulsion, in some embodiments less than 20% (e.g., 15%, 10%, 8%, 5% or less emulsion), and in some embodiments greater than 20% emulsion (e.g., 25%, 30%, 35%, 40% or more emulsion). An optimal amount for a particular administration can be ascertained by one of skill in the art using standard studies involving observation of immune responses described herein.

In some embodiments, it is expected that each dose (e.g., of a composition comprising a emulsion is from 0.001 to 95% or more (e.g., 0.001-10%, 0.5-5%, 1-3%, 2%, 6%, 10%, 15%, 20%, 30%, 40% or more) by weight emulsion.

Similarly, the present invention is not limited by the duration of time an emulsion is administered to a subject (e.g., to induce immune priming). In some embodiments, emulsion is administered one or more times (e.g. twice, three times, four times or more) daily. In some embodiments, a composition comprising emulsion is administered one or more times a day until a suitable level of immune response is generated and/or the immune response is sustained. In some embodiments, a composition comprising emulsion of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the emulsion present in the concentrated composition. Concentrated compositions are contemplated to be useful in a setting in which large numbers of subjects may be administered a composition of the present invention (e.g., a hospital). In some embodiments, a composition comprising emulsion of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In still a further embodiment, a composition comprising emulsion of the present invention remains stable and is usable in a sterilized (e.g., autoclaved at 121 Celsius for 15 minutes) form.

Dosage units may be proportionately increased or decreased based on several factors including, but not limited to, the weight, age, and health status of the subject. In addition, dosage units may be increased or decreased for subsequent administrations.

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing emulsions, immunogens, and other components and for screening for new components. Thus, it is not intended that the present invention be limited to any particular subject and/or application setting.

The formulations can be tested in vivo in a number of animal models developed for the study of pulmonary, mucosal and other routes of delivery. As is readily apparent, the compositions of the present invention are useful for preventing and/or treating a wide variety of diseases and infections caused by viruses, bacteria, parasites, and fungi. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest.

In one embodiment, the adjuvant mixtures of the present invention are useful for the production of immunogenic compositions that can be used to generate antigen-specific antibodies that are useful in the specific identification of that antigen in an immunoassay according to a diagnostic embodiment. Such immunoassays include enzyme-linked immunosorbant assays (ELISA), RIAs and other non-enzyme linked antibody binding assays or procedures known in the art. In ELISA assays, the antigen-specific antibodies are immobilized onto a selected surface; for example, the wells of a polystyrene microtiter plate. After washing to remove incompletely adsorbed antibodies, a nonspecific protein, such as a solution of bovine serum albumin (BSA) or casein, that is known to be antigenically neutral with regard to the test sample may be bound to the selected surface. This allows for blocking of nonspecific adsorption sites on the immobilizing surface and thus reduces the background caused by nonspecific bindings of antigens onto the surface. The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25-37° C. Following incubation, the sample-contacted surface is washed to remove non-immunocomplexed material. The washing procedure may include washing with a solution such as PBS/Tween, or a borate buffer.

Following formation of specific immunocomplexes between the antigen in the test sample and the bound antigen-specific antibodies, and subsequent washing, the occurrence, and even amount, of immunocomplex formation may be determined by subjecting the immunocomplex to a second antibody having specificity for the antigen. To provide detecting means, the second antibody may have an associated activity, such as an enzymatic activity, that will generate, for example, a color development upon incubating with an appropriate chromogenic substrate. Quantification may then achieved by measuring the degree of color generation using, for example, a visible spectra spectrophotometer. In an additional embodiment, the present invention includes a diagnostic kit comprising antigen-specific antibodies generated by immunization of a host with immunogenic compositions produced according to the present invention.

In some embodiments, the present invention provides a kit comprising a composition comprising emulsions adjuvant. In some embodiments, the kit further provides a device for administering the composition. The present invention is not limited by the type of device included in the kit. In some embodiments, a kit comprises a composition comprising emulsions in a concentrated form (e.g., that can be diluted prior to administration to a subject).

In some embodiments, all kit components are present within a single container (e.g., vial or tube). In some embodiments, each kit component is located in a single container (e.g., vial or tube (e.g., emulsions adjuvant is present in one container and an immunogen is present in a second, separate container)). In some embodiments, one or more kit components are located in a single container (e.g., vial or tube) with other components of the same kit being located in a separate container (e.g., vial or tube). In some embodiments, a kit comprises a buffer. In some embodiments, the kit further comprises instructions for use.

Therapeutics and Prophylactics

Furthermore, in preferred embodiments, emulsions adjuvant compositions of the present invention induces (e.g., when administered to a subject) innate and adaptive/acquired immune responses (e.g., both systemic and mucosal immunity). Thus, in some preferred embodiments, administration of a composition of the present invention to a subject results in protection against an exposure to a pathogen. Although an understanding of the mechanism is not necessary to practice the present invention and the present invention is not limited to any particular mechanism of action, in some embodiments, the invention provides use of emulsion adjuvant formulations for administration via injection (e.g., an emulsion formulated for administration via injection comprising a cationic lipid that possesses a small, polar head and hydrophobic region (e.g., dual chain hydrophobic tail (e.g., DODAC)) that provides significant, robust and clinically useful immune responses when injected with an antigen that are not achieved and/or achievable using emulsions that are not formulated for administration via injection (e.g., an emulsion formulated for topical administration comprising a cationic surfactant that possesses a large polar head and only a single chain hydrophobic tail (e.g., CPC)).

In some embodiments, the present invention provides a composition (e.g., a composition comprising emulsion and one or more antigens/immunogens to serve as an injectable vaccine. This material can easily be produced with emulsion and antigen(s).

In some preferred embodiments, the present invention provides a composition for generating an immune response comprising emulsion and an immunogen (e.g., a purified, isolated or synthetic protein or derivative, variant, or analogue thereof; or, one or more serotypes of pathogens inactivated by the emulsion). When administered to a subject, a composition of the present invention stimulates an immune response against the immunogen/pathogen within the subject. Although an understanding of the mechanism is not necessary to practice the present invention and the present invention is not limited to any particular mechanism of action, in some embodiments, generation of an immune response (e.g., resulting from administration of a composition comprising emulsion and an immunogen) stimulates innate and/or adaptive/acquired immune responses that provides total or partial immunity to the subject (e.g., from signs, symptoms or conditions of a disease (e.g., caused by the pathogen)). Without being bound to any specific theory, protection and/or immunity from disease (e.g., the ability of a subject's immune system to prevent or attenuate (e.g., suppress) a sign, symptom or condition of disease) after exposure to an immunogenic composition of the present invention is due to adaptive (e.g., acquired) immune responses (e.g., immune responses mediated by B and T cells following exposure to emulsion comprising an immunogen of the present invention (e.g., immune responses that exhibit increased specificity and reactivity towards the pathogen). Thus, in some embodiments, the compositions and methods of the present invention are used prophylactically or therapeutically to prevent or attenuate a sign, symptom or condition associated with the pathogen.

In some embodiments, emulsion adjuvant is administered alone. In some embodiments, emulsion adjuvant comprises one or more other agents (e.g., a pharmaceutically acceptable carrier, excipient, and the like). In some embodiments, emulsion adjuvant is administered in a manner to induce a humoral immune response. In some embodiments, emulsion adjuvant is administered in a manner to induce a cellular (e.g., cytotoxic T lymphocyte) immune response, rather than a humoral response. In some embodiments, emulsion adjuvant induces both a cellular and humoral immune response.

Thus, in some embodiments, a composition comprising a nanoemulsion adjuvant of the present invention may be used to protect and/or treat a subject susceptible to, or suffering from, a disease by means of administering a compositions comprising a nanoemulsion adjuvant by intramuscular, intraperitoneal, intradermal, transdermal, intravenous, subcutaneous or other route of administration described herein. Methods of systemic administration of the adjuvant preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the adjuvant composition of the present invention.

In some embodiments, it is expected that each dose (e.g., of a composition comprising a nanoemulsion adjuvant and an immunogen (e.g., administered to a subject to induce an immune response (e.g., a protective immune response (e.g., protective immunity)))) comprises 0.05-5000 µg of each immunogen (e.g., recombinant and/or purified protein), in some embodiments, each dose will comprise 1-500 µg, in some embodiments, each dose will comprise 350-750 µg, in some embodiments, each dose will comprise 50-200 µg, in some embodiments, each dose will comprise 25-75 µg of immunogen (e.g., recombinant and/or purified protein). In some embodiments, each dose comprises an amount of the immunogen sufficient to generate an immune response. An effective amount of the immunogen in a dose need not be quantified, as long as the amount of immunogen generates an immune response in a subject when administered to the subject. An optimal amount for a particular administration (e.g., to induce an immune response (e.g., a protective immune response (e.g., protective immunity))) can be ascertained by one of skill in the art using standard studies involving observation of antibody titers and other responses in subjects.

In some embodiments, it is expected that each dose (e.g., of a composition comprising a nanoemulsion adjuvant and an immunogen (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria or virus, or recombinant and/or purified protein). In some embodiments, an initial or prime administration dose contains more immunogen than a subsequent boost dose In some embodiments, a composition comprising a nanoemulsion adjuvant of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising about 0.1-50% of the nanoemulsion adjuvant present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a nanoemulsion adjuvant of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Generally, the emulsion compositions of the invention will comprise at least 0.001% to 100%, preferably 0.01 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention. Some variation in dosage will necessarily occur depending on the condition of the specific pathogen and the subject being immunized.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

EXAMPLES

The following examples serve to illustrate certain preferred embodiments and aspects of the present invention and are not to be construed as limiting the scope thereof.

Example 1

Nanoemulsion In Vitro Studies

A library of different nanoemulsion (NE) formulations with varying cationic and nonionic surfactants and surfactant-blend ratios were manufactured (NanoBio Corp., Ann Arbor, MI) and analyzed and characterized in experiments conducted during development of the invention.

NE formulations were manufactured by high-speed emulsification of ionic and nonionic surfactants, organic solvent (e.g., ethanol (200 proof) glycerol, etc.), soybean oil and purified water using a high speed homogenizer. Emulsion formulations tested including combinations of various ionic and nonionic surfactants at different ratios were produced (See Tables 1-4, below). Ionic surfactants were selected based on the differences in the structures of the polar head groups and hydrophobic tails in order to produce NEs with diverse physicochemical properties. Surfactant structures and abbreviations as well as their hydrophilic-lipophilic balance values (HLB) are shown in Table 4 and FIG. 1. Surfactant blend ratios of the NEs are annotated according to the ratio of ionic to nonionic surfactants. For example, a CPC/Tween80 NE annotated as 1:6 contains one part CPC to six parts Tween 80 (by weight), and a NE of Tween 80 with no cationic surfactant is annotated as 0:6.

Nanoemulsion formulations were screened in vitro for biological activity including cell cytotoxicity, ability to facilitate antigen uptake into dendritic or epithelial cells, and interaction with mucin as a measure of mucoadhesion.

Cell lines used for characterization of emulsion properties. Murine epithelial, dendritic and macrophage cell lines were purchased from American Type Culture Collection, Manassas, VA and demonstrated to be free of *mycoplasma* contamination by RT-PCR (PCR *Mycoplasma* Detection Set, Takara Bio Inc.). Cell lines used included TC-1 (epithelial), Jaws II (dendritic), and Raw 264.7 (macrophage). TC-1 (ATCC, CRL-2785) is a murine epithelial cell line derived from lung epithelial cells from a C57BL/6 mouse. JAWS II (ATCC, CRL-11904) is an immortalized immature myeloid-type dendritic cell line derived from a p53-deficient C57BL/6 (H-2b) mouse. Raw 264.7 (ATCC, TIB-71) is a macrophage cell line established from the ascites of an Abelson murine leukemia virus (A-MuLV)-induced tumor from a BAB/14 mouse, and Raw-blue is a macrophage reporter cell line derived from Raw 264.7 and expresses secreted embryonic alkaline phosphatase (SEAP) gene under the control of inducible NF-κB and AP-1 transcription factors.

TC-1 cells were grown in RPMI 1640 media with L-glutamine (Corning), containing 10% heat-inactivated FBS (HI-FBS) (Gemini), 1× nonessential amino acids, 10 mM HEPES, 100 IU penicillin, and 100 µg/mL streptomycin (Gibco). Jaws II cells were maintained in MEM-α media containing 10% HI-FBS, 2 mM L-glutamine, 1 mM sodium pyruvate, 5 ng/mL mouse granulocyte macrophage colony-stimulating factor (mGM-CSF), 100 IU penicillin, and 100 µg/mL streptomycin. Raw 264.7 cells were maintained in DMEM 10% FBS supplemented with penicillin/streptomycin (100 IU/ml) (Mediatech). Raw Blue cells were grown in DMEM with 10% HI-FBS, 100 µg/mL Normocin (Invivogen), 200 µg/mL Zeocin and 2 mML-glutamine.

Cellular Toxicity Screening. Cellular toxicity was evaluated using an automated format of the Cell Titer-Glo Luminescent Cell Viability Assay (Promega) at the High-Throughput Screening Laboratory (Life Sciences Institute, University of Michigan). Cells were seeded overnight on 384-well plates at 37° C. Cell suspension was dispensed using a Multidrop 384 (Thermo Scientific) system. Seeding densities for different cell types were as follows: TC-1: 1×104 cells/well; Jaws II: 1.5×104 cells/well; Raw-Blue: 2.0×104 cells/well in 40 μL of media/well. 3-fold serial dilutions of NE were prepared in the respective cell culture medium, spanning a 100,000-fold concentration range (1-0.000017% NE (w/v)). Media was removed from the plates, and 40 μL of the NE dilutions were added to each well. Each condition was run in duplicate. Cells were incubated for 24 h at 37° C. Supernatant was aspirated with an ELx405 microplate washer (Biotek), and cells were washed with PBS (3×). 10 μL of CellTiter-Glo reagent was added to each well and incubated at RT for 15 min. Luminescence was measured on a PHERAstar plate reader (BMG LabTech). The IC50 was defined as the NE concentration (% w/v) at which there is 50% cell viability after 24 h of treatment.

Antigen uptake. To measure antigen uptake, TC-1 cells were seeded overnight in 24-well plates at a density of 1×105 cells per well in TC-1 culture media. A 10 times concentrated mixture of NE (0.25%, 0.5%, 1%) and DQ-Ovalbumin (50 μg/mL) (DQ-OVA) (Life Technologies) was prepared in PBS, pH 7.4, and incubated for 15 min at room temperature (RT). DQ-OVA is ovalbumin conjugated to a self-quenching fluorophore. DQ-OVA is minimally fluorescent while OVA is intact, but upon proteolytic processing of OVA, the fluorophore is unquenched, resulting in a large increase in fluorescence. Cell culture media on the cells was replaced with fresh TC-1 media, and the NE-OVA solution was then added to the media to obtain final concentrations of 0.025%, 0.05%, and 0.1% NE with 5 μg/mL DQ-OVA. Cells were treated for 2 h at 37° C. Media was collected from each well and placed in separate flow cytometry tubes. The wells were rinsed with 1 mL of PBS, and this wash was collected and added to the corresponding tubes. The remaining adherent cells in each well were then removed by trypsinization, and added to the corresponding flow cytometry tubes containing the media collected from the wells and the PBS wash. Wells were rinsed with an additional 1 mL of PBS to ensure collection of all remaining cells, and this wash was collected and added to the corresponding tubes. Samples were spun at 2000 rpm for 5 min at 4° C. The supernatant was discarded, and the cells were washed with 4 mL of FACS buffer (PBS containing 0.1% bovine serum albumin and 0.1% sodium azide). Cells were spun again, and the pellet was resuspended in 500 μL of FACS buffer. Flow cytometry was performed on a Beckman Epics XL flow cytometer. The mean fluorescence intensity (MFI) for cells with DQ-OVA uptake (and proteolytic processing) was measured on FL-1 (excitation 488 nm, emission 530/30 nm). Uptake for Jaws II and Raw cells were performed similarly.

Change in zeta potential in presence of mucin. Dynamic light scattering (DLS) and zeta potential (ZP) measurements were performed consecutively for the same sample on a Zetasizer Nano-ZS (Malvern Instruments Ltd). Porcine gastric mucin type III (mixture of different mucin isoforms) (Sigma-Aldrich), was rehydrated at 1 mg/mL in 1 mMHEPES pH 7 at RT for 30 min prior to performing the assay. 0.1% NE (w/v) was mixed with 0.05 mg/mL mucin in 1 mMHEPES pH 7, and incubated for 2 m before measurements. Particle size (PS) is expressed as average diameter (Zaved). ΔZave represents the difference between the PS with mucin (Zave final) and the PS without (Zave init). ΔZP represents the difference between the ZP without mucin and the ZP with mucin (ZPinit−ZPfinal).

TABLE 1

Type of surfactants, oils and solvents used to prepare nanoemulsions.

| Cationic Surfactants (Positive) | Nonionic Surfactants (Neutral) | Oil | Solvents |
|---|---|---|---|
| Cetylpyridinium Chloride (CPC) | Tween Series (T 20, T21, T60, T80, T85) | Soybean | Ethanol Glycerol |
| Benzalkonium Chloride (BAC) | Span Series (S20, S40, S60, S 65, S80, S85) | | |
| Stearalkonium chloride (SAC) | Poloxamers (P124, P188, P237, P 338, P407) | | |
| Cetrimonium chloride (CTAC) | Tyloxapol | | |
| Cetrimonium chloride (CTAB) | | | |
| Cocamidopropyl betaine (CAB) | | | |
| Benzethonium chloride (BEC) | | | |
| Dioctadecyl dimethyl ammonium chloride or bromide (DODAC or DODAB) | | | |
| Totals: 9 | 17 | 1 | 2 |

Emulsion formulations that passed or failed stability assessment are provided in Table 2. Briefly, formulations were placed on short term stability for 2 weeks at 25° C./60RH and 40° C./75% RH. Parameters assessed for stability were: appearance, particle size (Z-average and polydispersity index), zeta potential, and pH.

TABLE 2

Summary of nanoemulsion formulations placed on short term stability

| Stability Table Numbers | Type of Nanoemulsion | Pass | Fail |
|---|---|---|---|
| 1 | Cetypyridinum Chloride (CPC) Nanoemulsions | 87 | 1 |
| 2 | Benzalkonium Chloride (BAC) Nanoemulsions | 22 | 32 |
| 3 | Nonionic (No Charge) Nanoemulsion | 4 | 0 |
| 4 | CPC + Surfactant Combinations | 24 | 0 |
| 5 | Benzethonium Chloride (BEC) Nanoemulsions | 7 | 0 |
| 6 | Cetyltrimethylammonium Bromide (CTAB) Nanoemulsions | 7 | 0 |
| 7 | Cetyltrimethylammonium Chloride (CTAC) Nanoemulsions | 7 | 0 |
| 8 | Dioctadecyldimethylammonium Chloride (DODAC) Nanoemulsions | 16 | 6 |
| 9 | Dioctadecyldimethylammonium Bromide (DODAB) Nanoemulsions | 5 | 3 |
| 10 | Cocamidopropyl Betaine (CAB) Nanoemulsions | 2 | 2 |
| 11 | Stearalkonium Chloride (SAC) Nanoemulsions | 4 | 0 |
| 12 | CPC/DODAC Nanoemulsions | 12 | 0 |
| | Total | 197 | 44 |

Criteria used for assessment of stability are provided in Table 3.

TABLE 3

| Stability specifications for Nanoemulsion Formulations | | |
|---|---|---|
| TEST | METHOD | ACCEPTANCE CRITERIA |
| Appearance | Visual | White to off white liquid; no phase separation; moderate creaming and settling is acceptable |
| pH | pH meter | 4.0-6.0 |
| Particle Size | Dynamic light scattering | Less than 1000 nm |
| Zeta Potential | Electrophoretic light scattering | Report results |

The structure, critical micelle concentration, HLB, molecular weight, and chain length of the cationic surfactants tested are listed in Table 4, below.

Figure 1A:
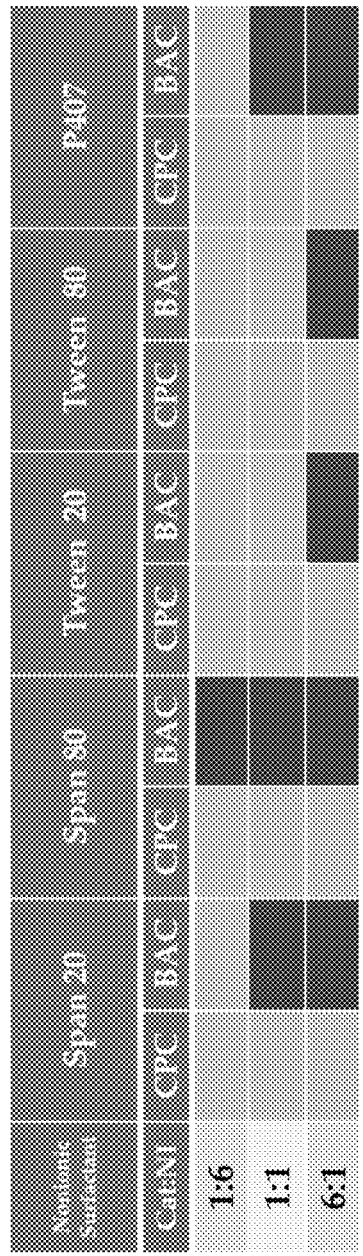

As shown in FIG. 1A, a significant amount of instability was observed for emulsions formulated with Benzalkonium Chloride (BAC).

Figure 1B:
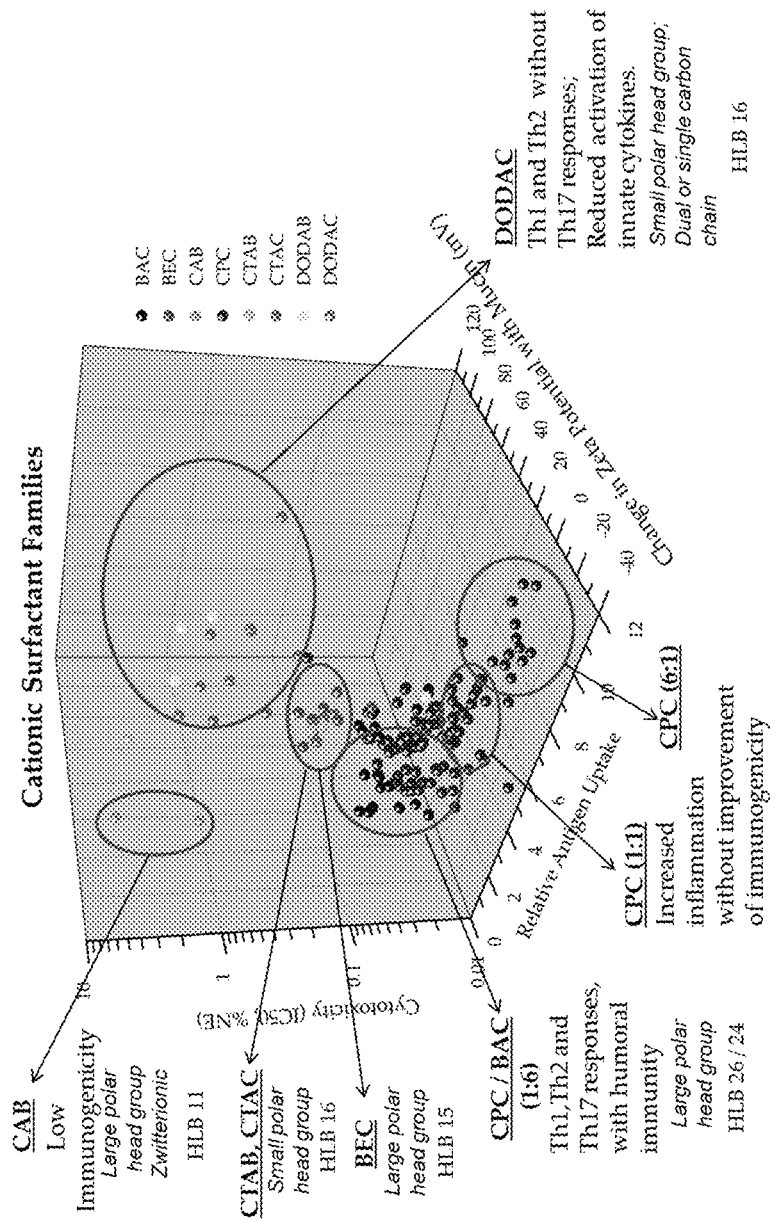

A surprising, dominant role was identified for the cationic surfactant in the biological activity of the manufactured nanoemulsions as assessed by high-throughput screening using the above described assays (See FIG. 1B). In particular, nanoemulsions formulated using dioctadecyl dimethyl ammonium chloride (DODAC) or dioctadecyl dimethyl ammonium bromide (DODAB) cationic surfactant demonstrated a uniquely high antigen uptake into cells concomitant with very low cellular toxicity (50% inhibitory concentration, IC50, >0.5%) when compared to other nanoemulsion formulations in the library including nanoemulsions containing the cationic surfactant cetylpyridinium chloride (CPC) (See FIG. 1B).

TABLE 4

| Name of Cationic Surfactant | MW | HLB | CMC (mM) | Chain Length | Structure |
|---|---|---|---|---|---|
| Previously Investgated Surfactants | | | | | |
| Cetylpyridinium Chloride (CPC) | 339 | 26 | 0.1 | 16 | 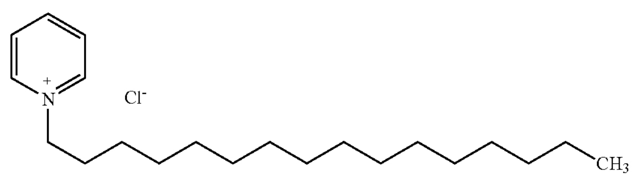  |
| Benzalkonium Chloride (BAC) | 354 | 24 | 0.47 | 6-10 | 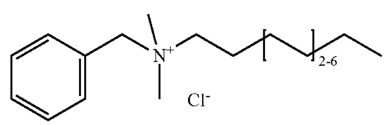  |
| Benzethonium chloride (BEC) | 448 | 15 | 0.84 | 4 | 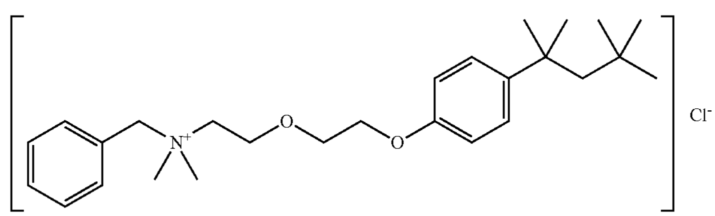  |
| New Surfactans | | | | | |
| Stearalkonium chloride (SAC) | 424 | 11 | — | 18 | 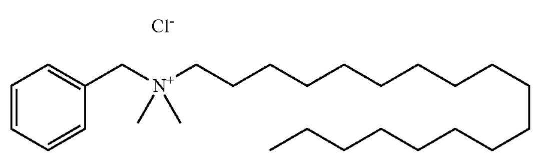 [SMILES: [Cl-] ; CCCCCCCCCCCCCCCCCC[N+](C)(C)Cc1ccccc1]  |
| Cocamidopropyl betaine (CAB) | 342 | 11 | 0.105 | 11 | 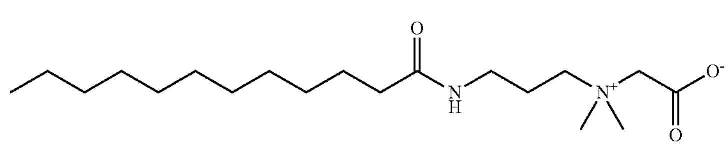 [SMILES: CCCCCCCCCCCC(=O)NCCC[N+](C)(C)CC(=O)[O-]]  |
| Dioctadecyl dimethyl ammonium chloride (DODAC) | 586 | NA | 10* | 18 (dual chain) | 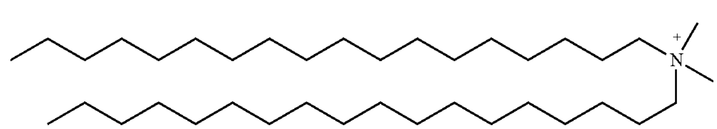  |

As shown in FIG. 1B, nanoemulsions formulated with a cationic surfactant containing a large polar head group (e.g., $W_{80}5EC$ formulated using cetylpyridinium chloride (CPC) as the cationic surfactant) are characterized by comparatively higher cell cytotoxicity (IC50<0.01) than nanoemulsions formulated with cationic surfactant containing a small polar head group and a dual chain hydrophobic component (e.g., DODAC formulations), low or intermediate uptake of antigen into epithelial or dendritic cells in screening assays in vitro, and strong induction in vivo of humoral and cellular immune responses (Th1, Th2 and Th17) when evaluated via the intranasal route of vaccine administration. In sharp contrast, nanoemulsions formulated with a cationic surfactant possessing a small polar head group and a dual hydrophobic chain tail group (e.g., the cationic surfactant dioctadecyl dimethyl ammonium chloride (DODAC) and dioctadecyl dimethyl ammonium bromine (DODAB)) display comparatively low cell cytotoxicity, activate low Th1 and Th2 cell-mediated immune responses without induction of Th17-type immunity, and generally provide poor adjuvant activity when administered by the intranasal route.

Although nanoemulsions formulated with a cationic surfactant possessing a small polar head group and a dual hydrophobic chain tail group (e.g., the cationic surfactant dioctadecyl dimethyl ammonium chloride (DODAC) and dioctadecyl dimethyl ammonium bromine (DODAB)) were characterized as being poor/suboptimal as intranasal adjuvants (See FIG. 1B), additional experiments were conducted during development of embodiments of the invention in order to evaluate and identify whether nanoemulsion formulations might exist that are useful as intramuscular adjuvants (See Examples 2-4, below).

Example 2

Comparison of Intramuscular Administration of Immunogenic Compositions Containing RSV F Protein and a Nanoemulsion Formulation Containing a Cationic Surfactant with Polar Head Group and Dual Chain Hydrophobic Component (e.g. DODAC) Versus an Immunogenic Compositions Containing RSV F Protein and Nanoemulsion Formulation Containing Large Polar Head Group and Absence of Dual Chain Hydrophobic Component Experiments were conducted to determine what effect, if any, administration of an immunogenic composition containing a nanoemulsion formulated with a cationic surfactant with a large polar head group and absence of a dual chain hydrophobic component (e.g., CPC) versus administration of an immunogenic composition containing a nanoemulsion formulated with cationic surfactant with a small polar head group and a dual hydrophobic chain tail group (e.g., the cationic surfactant dioctadecyl dimethyl ammonium chloride (DODAC) and dioctadecyl dimethyl ammonium bromine (DODAB)) would have on immunogenicity when used for administration via injection (e.g., intramuscular, intradermal and/or subcutaneous administration).

Vaccine preparation. Vaccines were prepared by mixing recombinant respiratory syncytial virus (RSV) F protein with specific nanoemulsion to the final protein concentration of 2 µg/dose. The nanoemulsions used for vaccine preparation were used at 5, 10, or 20% final concentration. Alum-adjuvanted RSV F protein vaccine (positive control) was prepared by mixing F protein at 2 µg/dose with 250 µg/dose of Alhydrogel in PBS, pH 7.2.

Animals and dosing. CD-1 mice received 2 doses of (50 µl each) of either NE-adjuvanted, or Alum-adjuvanted RSV F protein vaccines intramuscularly at weeks 0 and 2. Mice were bled prior to each dose and were sacrificed at week 4. Sera was tested for anti-F antibodies and neutralizing activities. Spleens were harvested and mechanically disrupted in RPMI/5% FBS media to obtain single-cell suspensions for cytokine response measurements.

Splenocytes isolation. Splenocytes were isolated by centrifugation at 2000 rpm for 5 min, and re-suspended in 150 mM $NH_4Cl$ for 10 min to remove red blood cells. Then cells were spun and washed again in T-Cell media. The cell pellet was then re-suspended in T-Cell media (RPMI medium supplemented with 5% FBS, 2 mM L-glutamine, 1× non-essential amino acids, 55 µM β-mercaptoethanol, 1 mM sodium pyruvate, 10 mM MOPS, 100 IU penicillin, and 100 µg/mL streptomycin) and filtered through a cell strainer. Splenocytes were then plated at a density of $5\times10^5$ cells/well in 96-well tissue culture plates and stimulated as below.

Cellular Recall Response. Cellular response was evaluated at sacrifice in splenocytes isolated as described above. Isolated splenocytes on 96-well plates were stimulated with 5 µg/ml of F protein 150 µl of media for 96 hrs at 37° C. Cell supernatant was collected, and cytokine levels were assessed using a Milliplex MAP mouse cytokine/chemokine magnetic multiplex kit (Millipore) customized for IFN-γ, IL-2, -4, -5, -10, -13, -17a and TNF-α following the manufacturer's protocol.

ELISA. Specific antibodies against RSV F protein were assayed using ELISA. Plates were coated with F protein. Animal sera were diluted and placed in the wells. Secondary antibodies were HRP-conjugated anti-IgG. Enhanced K-blue TMB Substrate was used for color development. The amount of the specific antibodies in the test samples was calculated using an Excel template. This was done using a reference serum prepared from a pool of sera from vaccinated animals. The optical density (OD) values were plotted against dilutions and linear regression curves were generated. Any OD value greater than 2.599 was omitted. The area under the curve was measured and IgG was calculated by comparison to the reference control. The reference control is assigned a unit value and the results were compared to that value and expressed as ELISA units (EU).

Neutralization assays. Serum dilutions were mixed with 800 PFU of RSV. The serum/virus mixture was incubated at 37° C. for one hour then placed on Vero cells in 24 well plates. Plaques were allowed to grow, stained and counted as described above. The neutralization units at 50% were determined as a reciprocal of the sera dilution that reduces number of the plaques by 50%.

Statistical analysis. Statistical analysis was performed using GraphPad Prism software was performed using Mann-Whitney non-parametric test.

Figure 3:
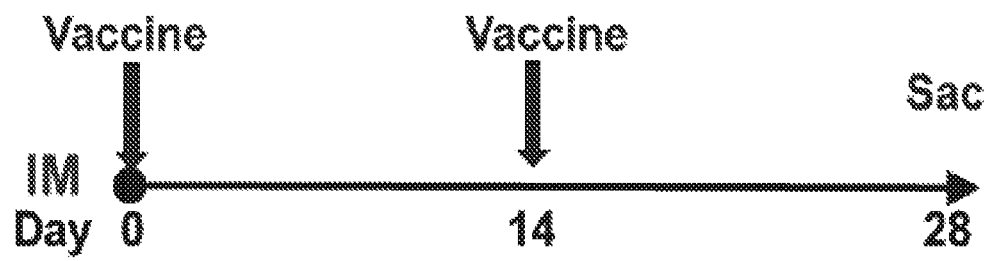
Figure 4:
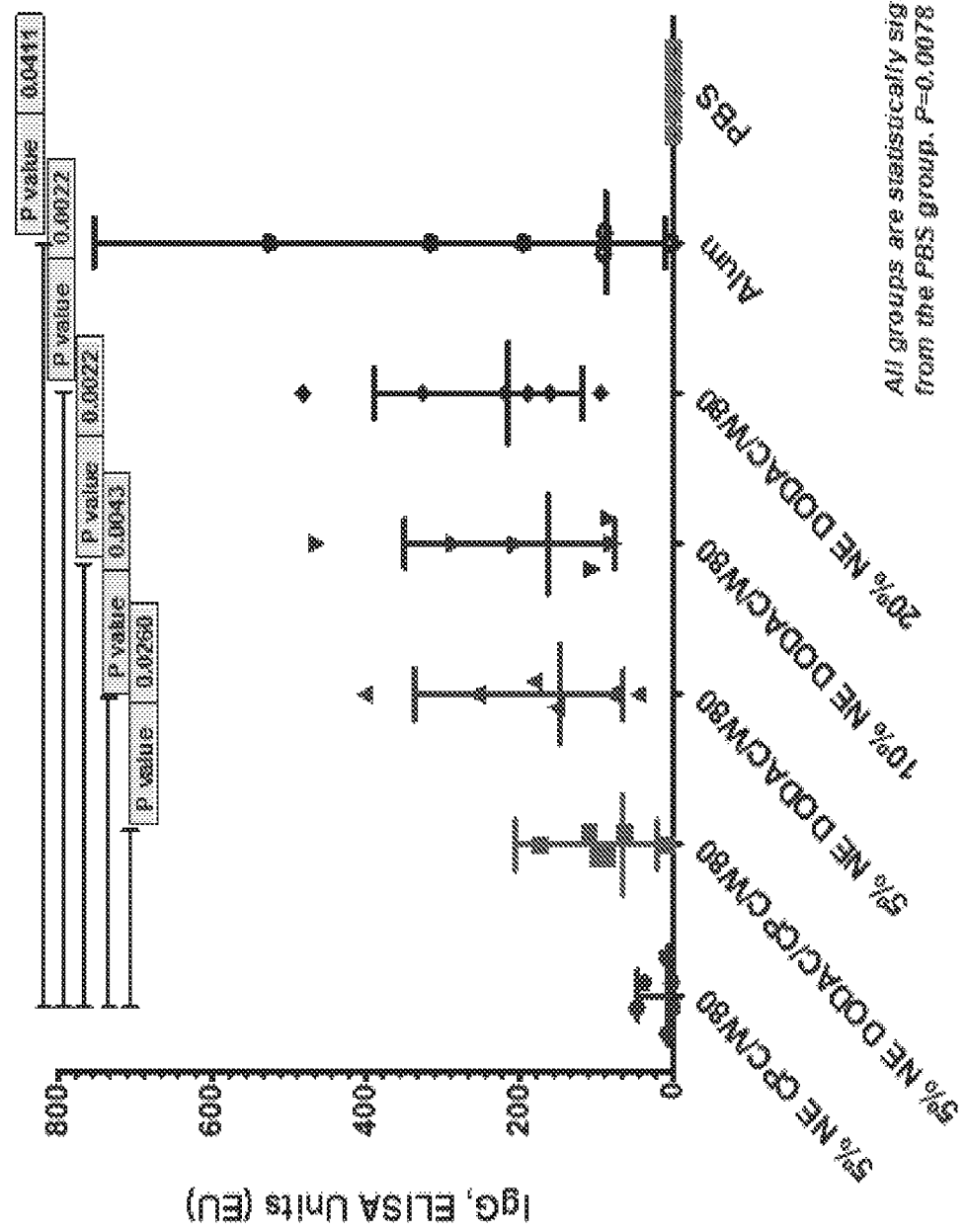

Mice received 2 µg/dose RSV F protein adjuvanted with either 5% W805EC, or 5, 10, or 20% DODAC, or 250 µg/dose Alum (See FIGS. 2 and 3). Serum antibodies against all vaccines showed increase after the first dose with a significant boost in the levels of antibodies after the second dose (FIGS. 4 and 5A-5B) as a result of vaccination. Intramuscular vaccination with either 5, 10, or 20% DODAC-adjuvanted vaccine provided a significantly higher level of F protein-specific antibodies in the sera of vaccinated animals compared to the positive control and compared to 5% W805EC-adjuvanted vaccine.

Figure 5B:
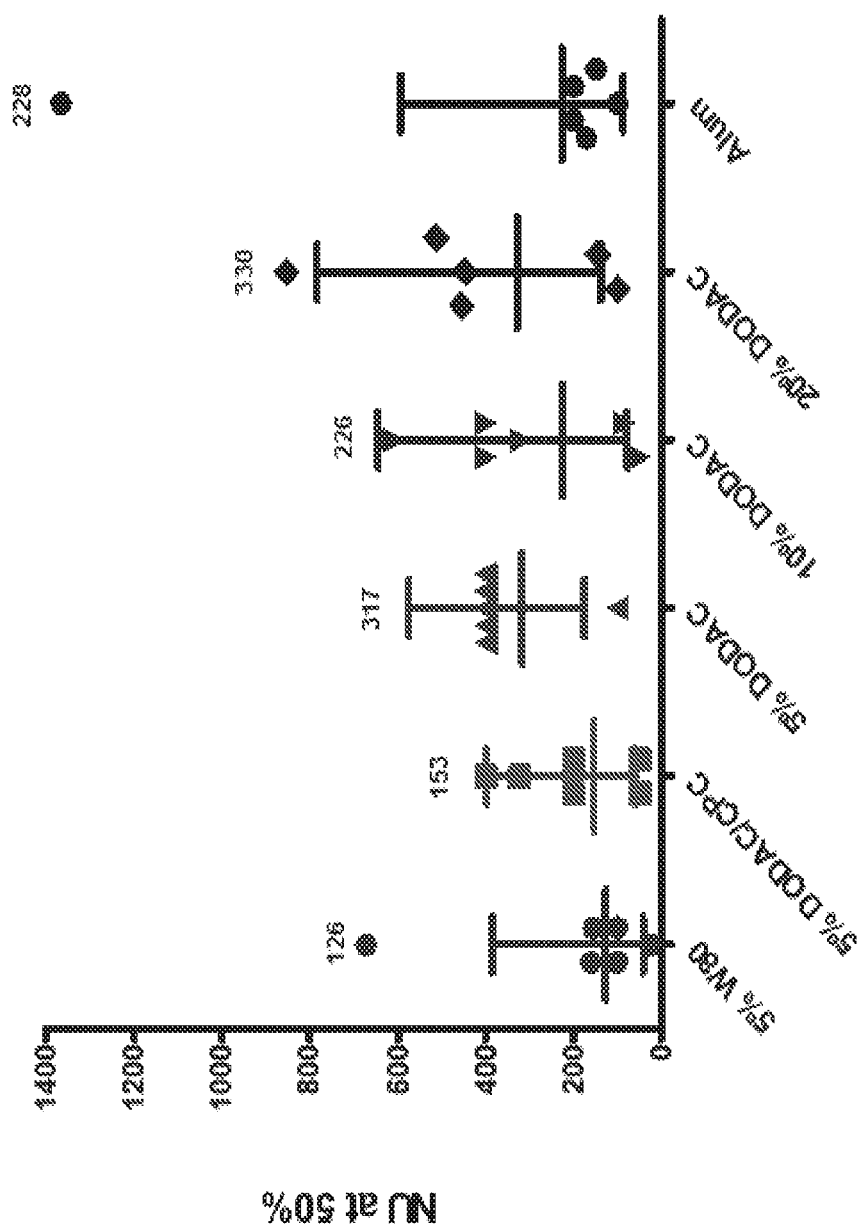

A similar trend was observed for neutralizing activity. DODAC-adjuvanted vaccines showed highest level of neutralization against RSV A2 with a greater number of high-responders in these groups (67% of animals having neutralization titers greater than 320) compared to animals immunized either with W805EC (80% with neutralization titers below 170), or Alum-adjuvanted vaccines (80% with neutralization titers below 200) (FIG. 5B).

Figure 6B:
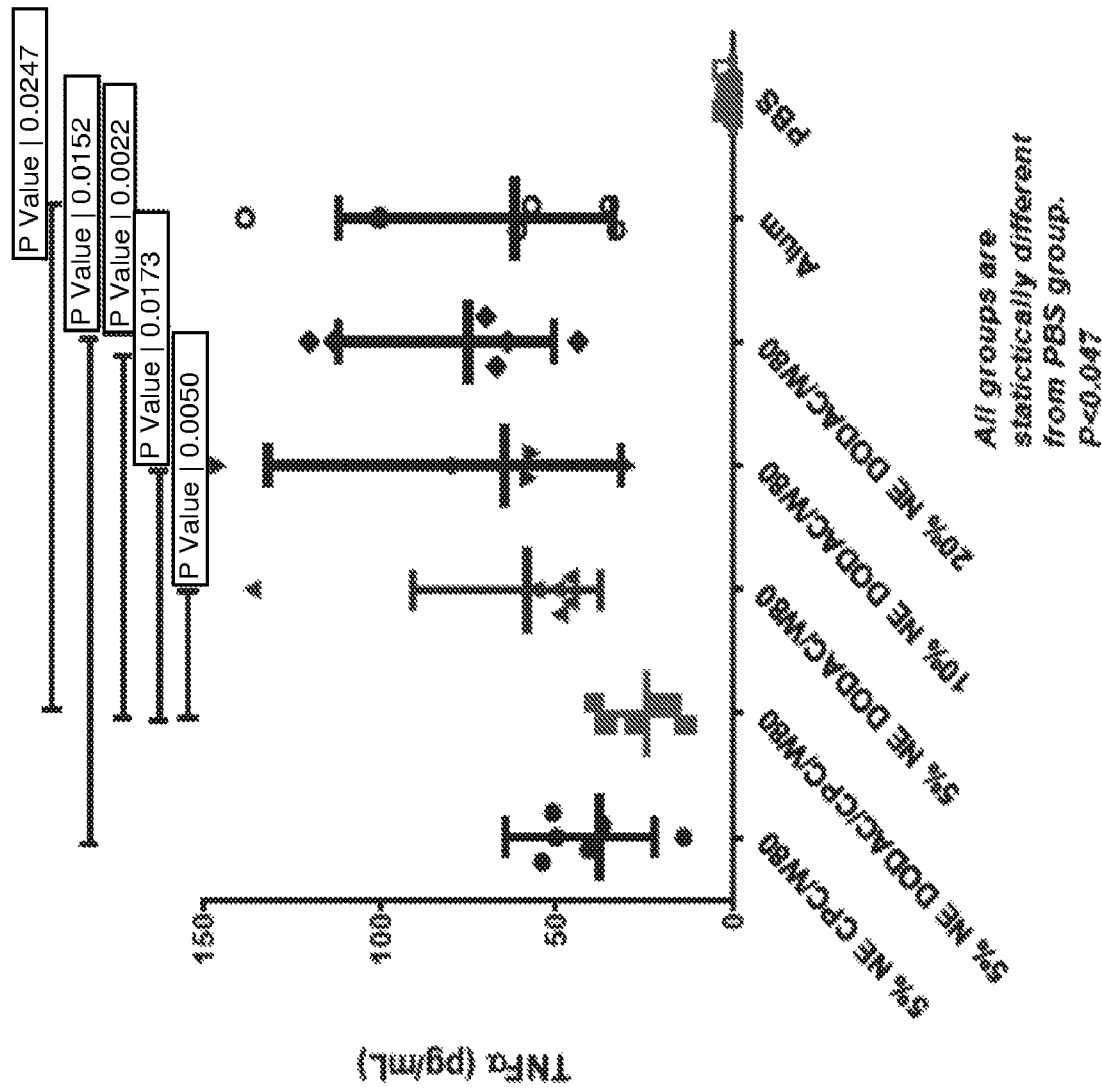
Figure 6C:
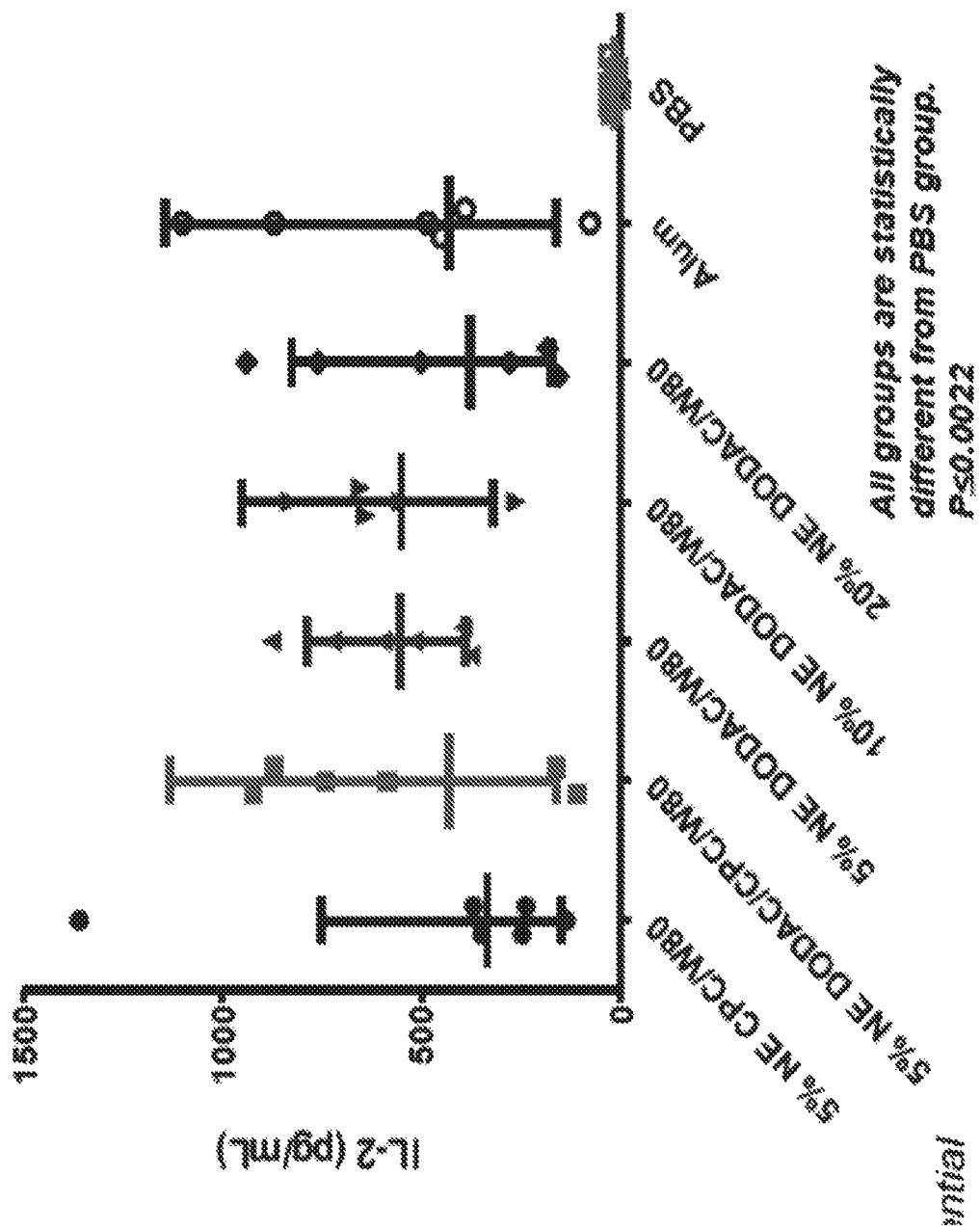
Figure 6D:
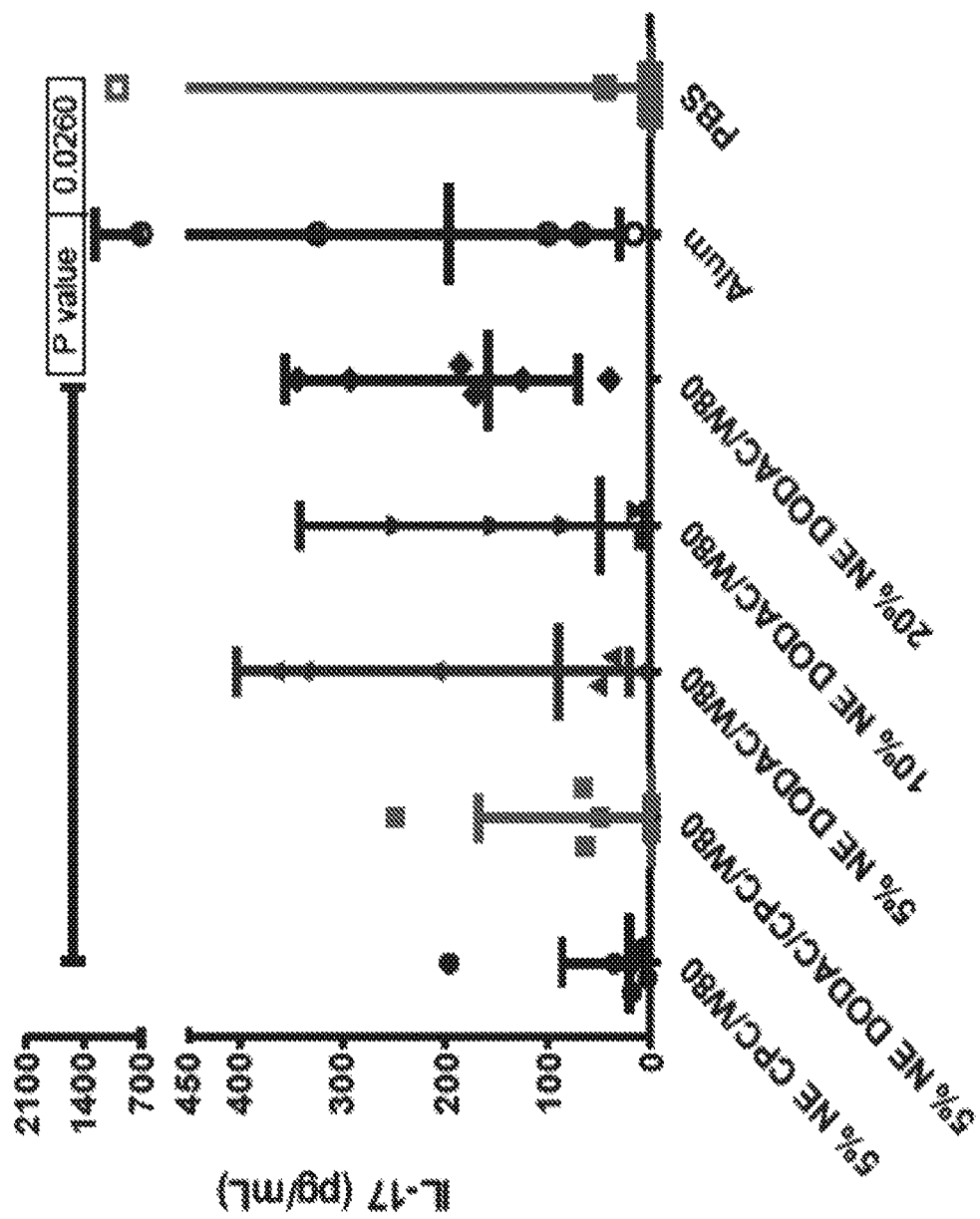
Figure 7A:
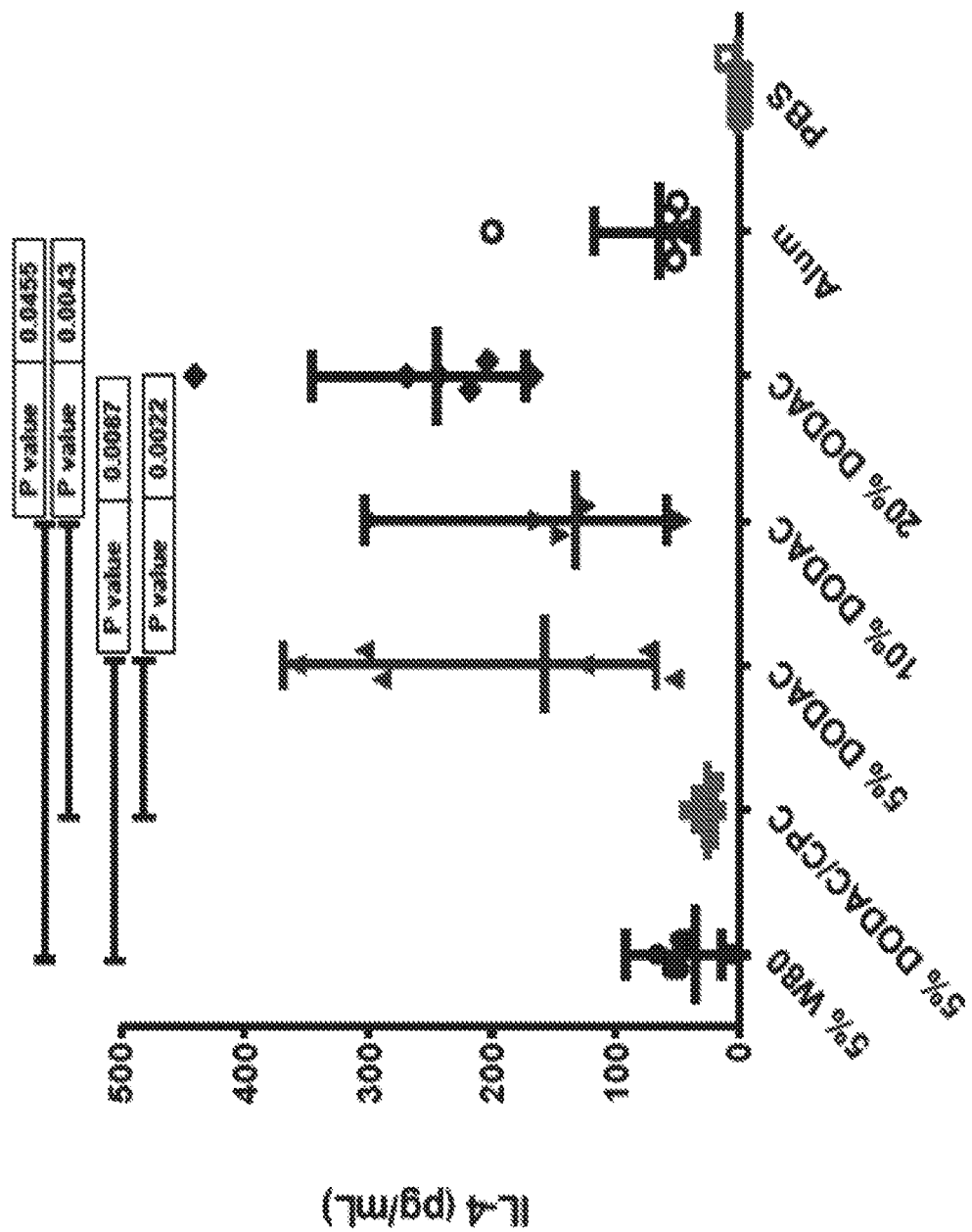
Figure 7B:
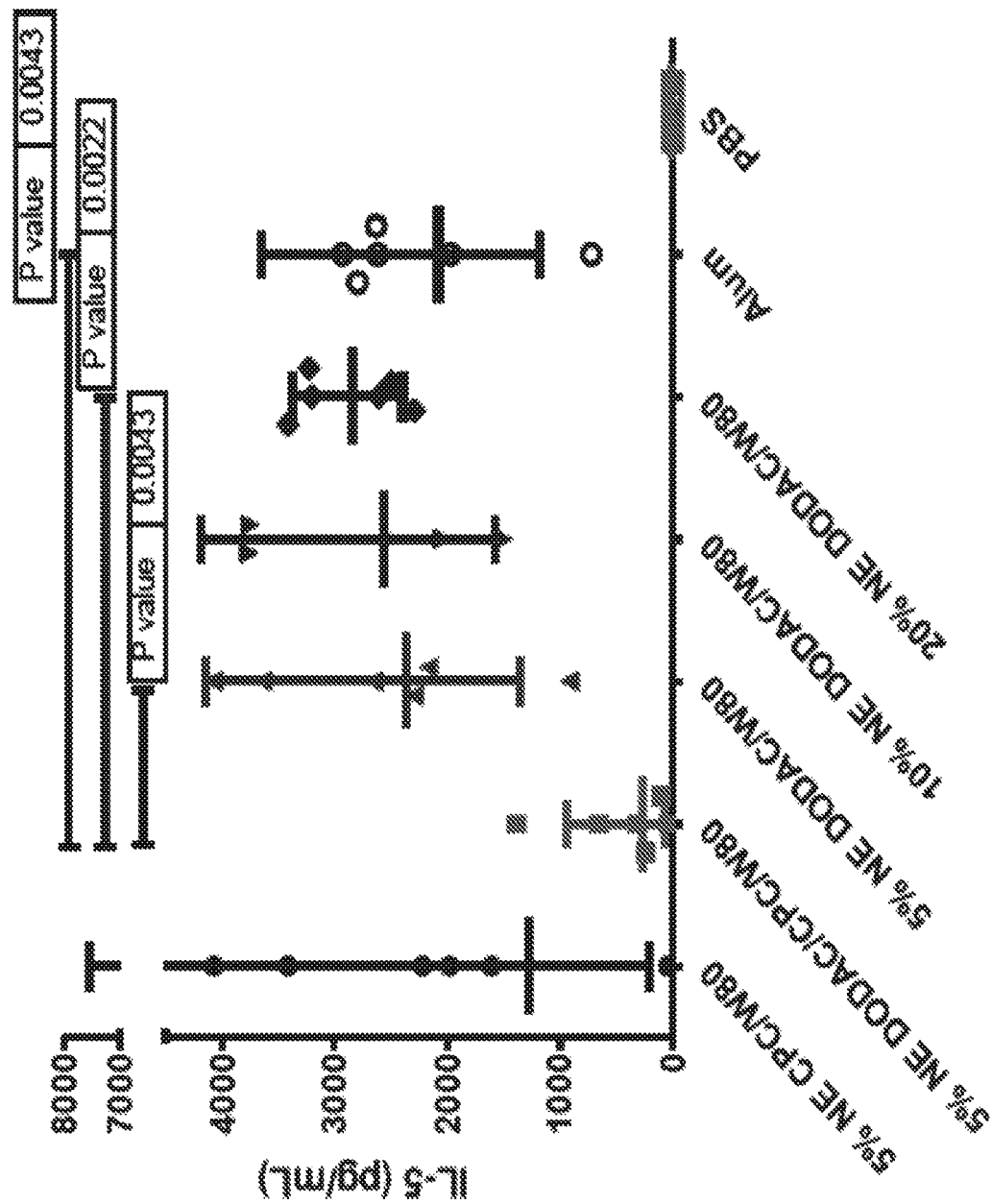
Figure 7C:
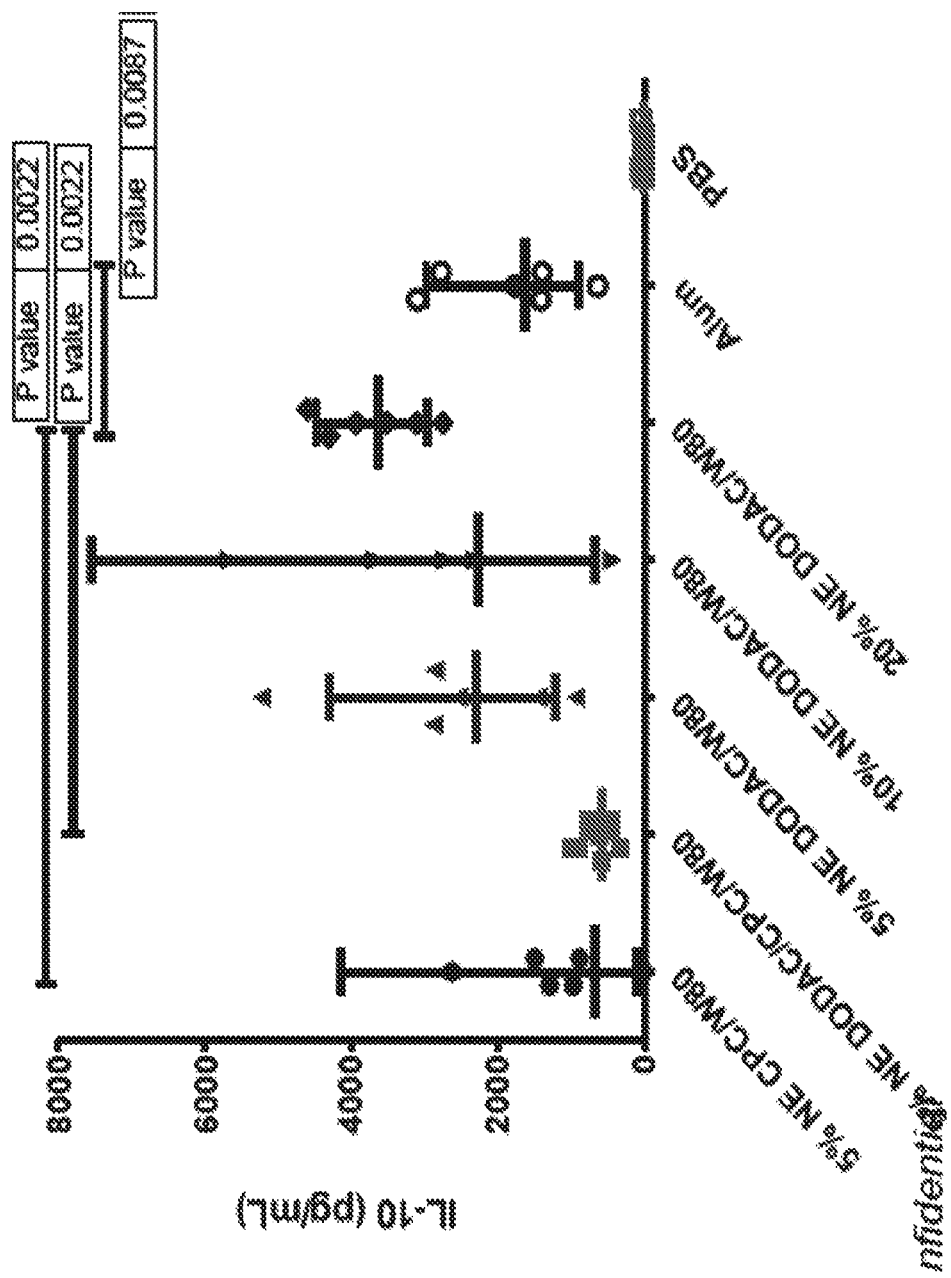
Figure 7D:
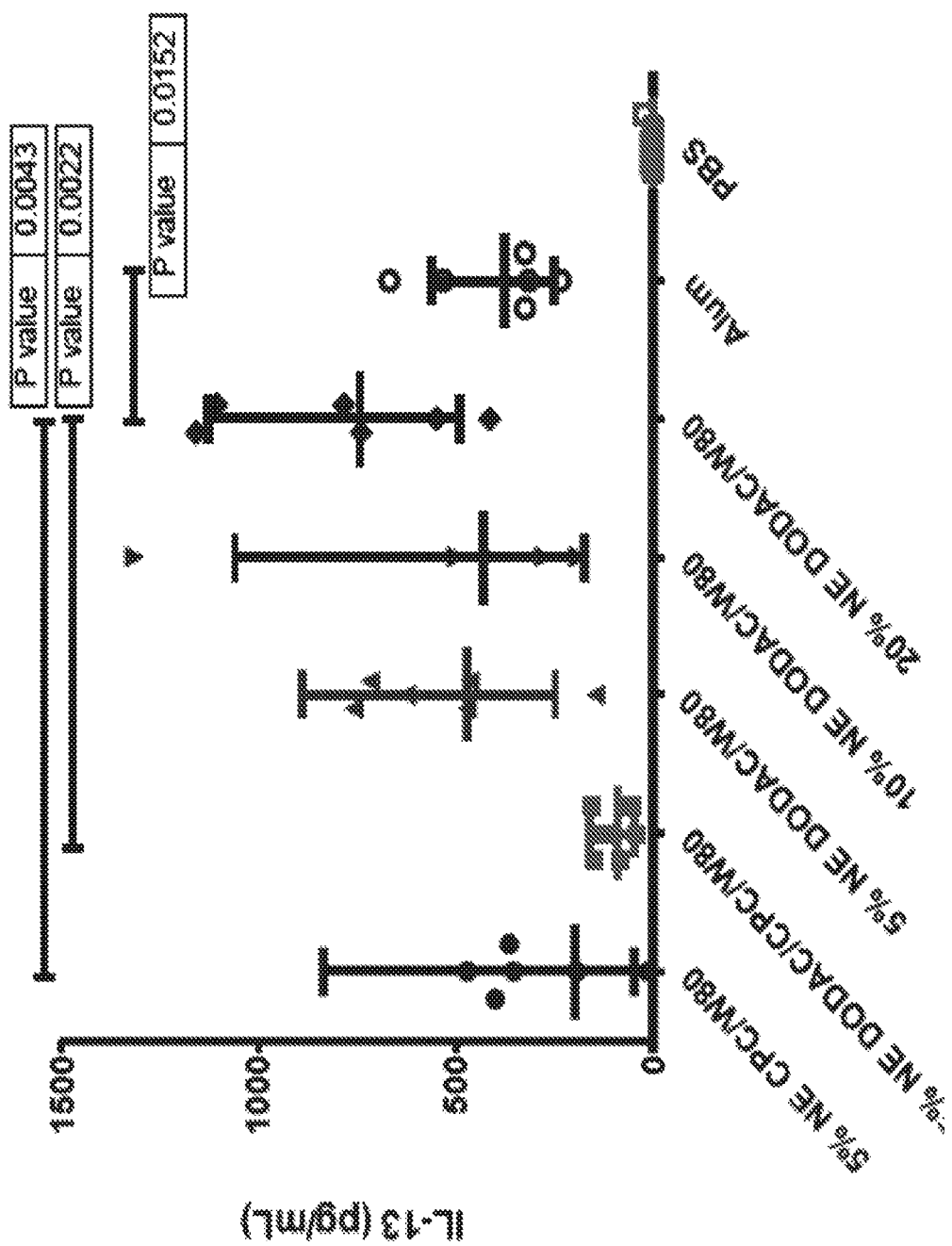

Thus, in one embodiment, the invention provides that immunogenic compositions containing and RSV antigen (e.g., recombinant F protein) and emulsion formulated with a cationic lipid containing a polar head group and a dual chain hydrophobic component (e.g., DODAC) display significantly higher efficacy for induction of functional and protective RSV-specific antibody responses when administered via injection (e.g., via intramuscular injection) compared both to an alum based positive control as well as to an immunogenic compositions containing emulsion formulated with CPC (large polar head group and absence of dual chain hydrophobic component). Thus, the invention identifies and provides novel immunogenic compositions containing emulsion formulated with cationic lipid containing a polar head group and a dual chain hydrophobic component as a significantly efficacious emulsion-based vaccine (e.g., formulated for injectable administration) against RSV. In addition, due to the absence of toxicity associated with emulsions formulated with DODAC or other cationic surfactant containing a polar head and dual chain hydrophobic component (e.g., versus emulsion containing CPC that is toxic), higher concentrations of the emulsion are able to be utilized in vaccines (e.g., in order to elicit higher antibody titers and Th1 responses compared to lower concentrations of the emulsion (e.g., See FIGS. 6 and 7).

Cell-mediated immune responses (FIGS. 6A-6D and 7A-7D) were analyzed in splenocytes stimulated with F protein to evaluate the antigen-specific cytokine response by T-cells. DODAC-adjuvanted vaccination resulted in activation of high levels of IFNγ, TNFα, IL-2 and IL-17 as well as Th2 cytokines with most balanced Th1/Th2/Th17 immune response after vaccination with 20% DODAC formulation. In addition, 20% DODAC-adjuvanted vaccine stimulated highest levels of IFNγ, cytokine that is particularly important for the protection from viral infections.

Example 3

Comparison of Intramuscular Administration of Immunogenic Compositions Containing Recombinant H5 Hemagglutinin Protein (rH5) Influenza Vaccine and a Nanoemulsion Formulation Containing a Cationic Surfactant with Polar Head Group and Dual Chain Hydrophobic Component (e.g. DODAC) Versus an Immunogenic Compositions Containing rH5 Influenza Vaccine and Nanoemulsion Formulation Containing Large Polar Head Group and Absence of Dual Chain Hydrophobic Component Based upon data described in Example 1 as well as other data generated during development of embodiments of the invention, the surprising finding that nanoemulsion adjuvant formulations containing a cationic surfactant with small polar head group and dual chain hydrophobic component (e.g., DODAC) performed remarkably well as an intramuscular adjuvant, but not as an intranasal adjuvant, was further studied and evaluated. Experiments were performed to directly compare and evaluate nanoemulsions formulated using the DODAC cationic lipid (with small polar head group and dual chain hydrophobic component) to W805EC, a CPC-containing formulation (CPC having a large polar head group and lacking a dual chain hydrophobic component), as an intramuscular vaccine adjuvant against pandemic influenza (H5N1). W805EC has previously been shown to be a robust mucosal adjuvant. Studies characterized the immunogenicity performance of intramuscular administration of immunogenic compositions containing recombinant multimeric H5 hemagglutinin protein (rH5) influenza vaccine and a nanoemulsion formulation containing CPC versus an immunogenic composition containing rH5 influenza vaccine and nanoemulsion formulation containing DODAC.

rH5 is the most advanced egg-free flu vaccine containing recombinant H5 hemagglutinin protein (rH5) produced by using a baculovirus expression vector system in SF+ insect cells (Cox and Hashimoto, J Invertebr Pathol. 2011; 107 (Suppl):S31-S41); Treanor J J, et al., Vaccine. 2011; 29:7733-7739). Experiments described below utilized a tobacco plant-derived and purified rH5 (See, e.g., Shoji et al., Human Vaccines 7: Supplement, 41-50; January/February 2011; 2011).

Materials and Methods

High-Throughput Screening of Novel Nanoemulsion Formulations.

A. Cellular toxicity. Cellular toxicity was evaluated using an automated format of the CellTiter-Glo Luminescent Cell Viability Assay (Promega) at the High-Throughput Screening Laboratory (Life Sciences Institute, University of Michigan). Cells were seeded overnight on 384-well plates at 37° C. The cell suspension was dispensed using a Multidrop 384 (Thermo Scientific) system. Seeding densities for different cell types were: TC-1 (epithelial cell line): $1 \times 10^4$ cells/well; Jaws II (dendritic cell line): $1.5 \times 10^4$ cells/well; Raw-Blue: $2.0 \times 10^4$ cells/well in 40 µL of media/well. Three-fold serial dilutions of emulsions were prepared in the respective cell culture medium, spanning a 100,000-fold concentration range (1-0.000017% emulsion (w/v)). Media was removed from the plates, and 40 µL of the emulsion dilutions were added to each well. Each condition was run in duplicate. Cells were incubated for 24 h at 37° C. Supernatant was aspirated using an ELx405 microplate washer (Biotek), and cells were washed with PBS (3×). 10 µL of CellTiter-Glo reagent was added to each well and incubated at room temperature for 15 min. Luminescence was measured on a PHERAstar plate reader (BMG LabTech). The IC50 is defined as the emulsion concentration (% w/v) at which there is 50% cell viability after 24 h of treatment.

B. Antigen uptake. TC-1 cells were seeded overnight in 24-well plates at a density of $1 \times 10^5$ cells per well. A 10 times concentrated mixture of emulsion (0.25%, 0.5%, 1%) and DQ-Ovalbumin (50 µg/mL) (DQ-OVA) (Life Technologies) was prepared in PBS, pH 7.4, and incubated for 15 minutes at room temperature (RT). DQ-OVA is ovalbumin conjugated to a self-quenching fluorophore. DQ-OVA is minimally fluorescent while OVA is intact, but upon intracellular proteolytic processing of OVA, the fluorophore is unquenched, resulting in a large increase in fluorescence. Cell culture media on the cells was replaced with fresh media, and the emulsion-OVA solution was then added to the media to obtain final concentrations of 0.025%, 0.05%, and 0.1% NE with 5 µg/mL DQ-OVA. Cells were treated for 2 h at 37° C. Media was collected from each well and placed in separate flow cytometry tubes. The wells were rinsed with 1 mL of PBS, and this wash was collected and added to the corresponding tubes. The remaining adherent cells in each well were then removed by trypsinization, and added to the corresponding flow cytometry tubes containing the media collected from the wells and the PBS wash. Wells were rinsed with an additional 1 mL of PBS to ensure collection of all remaining cells, and this wash was collected and added to the corresponding tubes. Samples were spun at 2000 rpm for 5 min at 4° C. The supernatant was discarded, and the cells were washed with 4 mL of FACS buffer (PBS containing 0.1% bovine serum albumin and 0.1% sodium azide). Cells were spun again, and the pellet was resuspended in 500 µL of FACS buffer. Flow cytometry was performed on a Beckman Epics XL flow cytometer. The mean fluorescence intensity (MFI) for cells with DQ-OVA uptake (and proteolytic processing) was measured on FL-1 (excitation 488 nm, emission 530 nm). Uptake for Jaws II and Raw cells was performed similarly.

C. Mucoadhesion. Dynamic light scattering (DLS) and zeta potential (ZP) measurements were performed consecutively for the same sample on a Zetasizer Nano-ZS (Malvern Instruments Ltd). Porcine gastric mucin type III (mixture of different mucin isoforms) (Sigma-Aldrich), was rehydrated at 1 mg/mL in 1 mM HEPES pH 7 at RT for 30 min prior to performing the assay. 0.1% emulsion (w/v) was mixed with 0.05 mg/mL mucin in 1 mM HEPES pH 7, and incubated for 2 m before measurements. Particle size (PS) is expressed as average diameter (Zaved). Δzave represents the difference between the PS with mucin (Zave final) and the PS without (Zave init). ΔZP represents the difference between the ZP without mucin and the ZP with mucin (ZPinit−ZPfinal).

CD-1 mouse studies. CD-1 mice (n=6-10 per treatment group) were immunized intramuscularly with three administrations, 2 weeks apart using 50 µL of the emulsion+rH5 mixture (5% emulsion and 10 µg rH5 antigen per mouse). Serum was obtained from the saphenous vein every 2-weeks post-initial immunization. Animals were sacrificed 6 weeks post-initial immunization. Spleens were harvested and mechanically disrupted in PBS to obtain single-cell suspensions for cytokine secretion analysis. Splenocytes were spun at 2000 rpm for 5 min and resuspended in ACK lysis buffer for <3 minutes to remove red blood cells (150 mM NH4Cl, 10 mM KHCO3, 0.1 mM EDTA). PBS was added to stop lysis, and cells were spun and washed again in PBS. The cell pellet was then resuspended in T-Cell media (DMEM medium supplemented with 5% FBS, 2 mM L-glutamine, 1× nonessential amino acids, 1 mM sodium pyruvate, 10 mM MOPS, 50 µM 2-mercaptoethanol, 100 IU penicillin, and 100 µg/mL streptomycin and filtered through a cell strainer. Splenocytes were then plated at a density of $4\times10^5$ cells/well in 96-well tissue culture plates and stimulated using 5 µg/ml rH5 antigen or medium alone. Cell-free supernatants were harvested after 72 hours culture at 37° C. Supernatants were stored at −80° C. prior to Luminex multiplex analysis (Millipore) to determine cytokine profiles.

rH5-specific IgG ELISA. Serum was obtained from the saphenous vein every 2-weeks post-initial immunization, and anti-rH5 specific IgG end-titers were measured by ELISA. Briefly, serum samples were serially diluted in PBS with 0.1% BSA, and incubated on microtiter plates coated with 1 µg/mL rH5. ELISAs were developed with an alkaline phosphatase detection system, and quantified by measuring the optical density (OD) at 405 nm (OD405). Endpoint titers are reported as the reciprocal of the highest serum dilution giving an OD above a cutoff value (sum of OD of the same dilution of a control serum from an untreated mouse and two times the standard deviation).

Hemagglutination inhibition assay. Serum samples from week 6 were analyzed using the HAI assay. Prior to analysis, serum samples were treated with receptor-destroying enzyme (RDE, Denka-Seiken) at 37° C. followed by heat inactivation of RDE at 56° C. and storage at 4° C. during analysis. The assays used A/Indonesia/05/05 (xPR8 IBCDC RG-2 from CDC) virus and 1% horse red blood cells. Serum dilutions started at 1:20 and samples without detectable HAI activity were assigned a value of 10.

Groups of CD-1 mice (8 animals per group) were immunized intramuscularly in a series of three vaccinations at 2 week intervals. Serum was obtained prior to each vaccination. Mice were sacrificed 2 weeks after the final immunization (Week 6) for evaluation of serum antibodies to assess humoral immunity, and rH5-specific cytokine release by spleen cells as a measure of the cell-mediated immune response (CMI).

Figure 8:
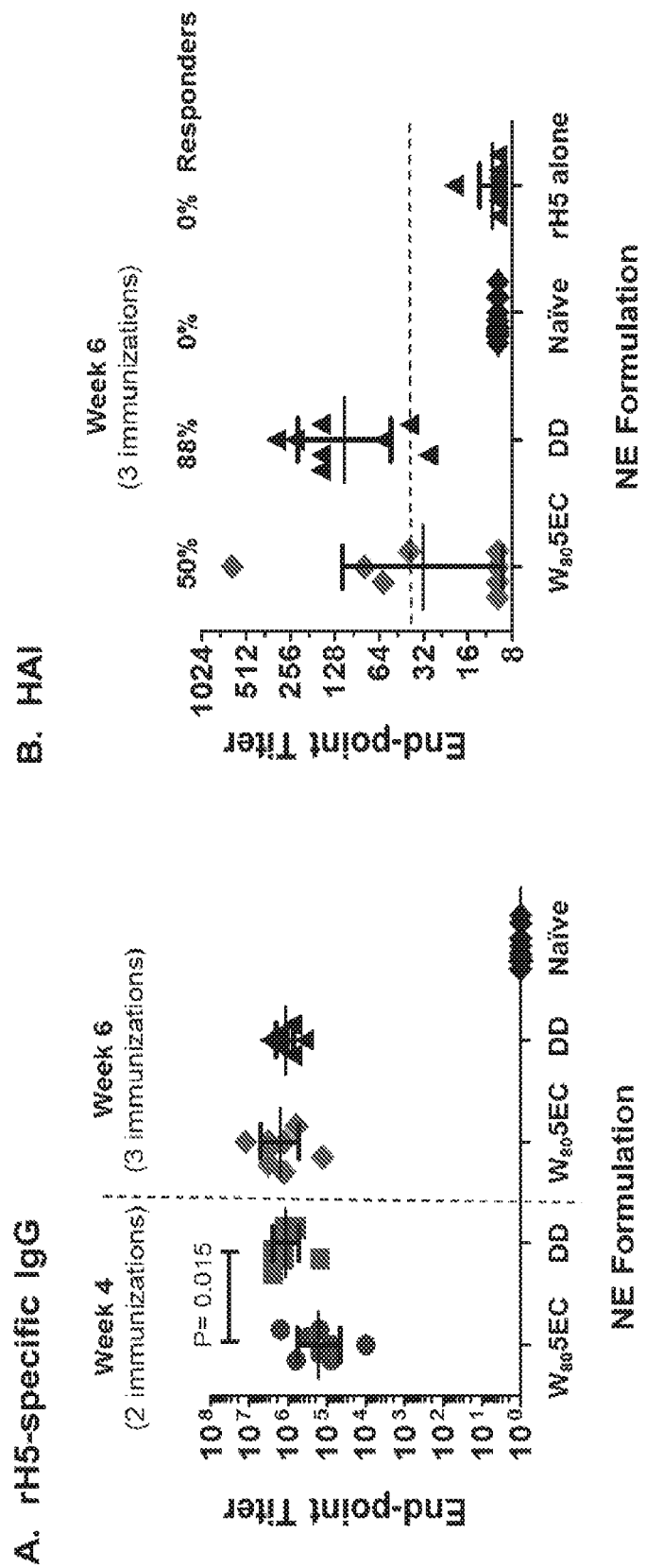

As shown in FIG. 8, the DODAC formulation (DD) stimulated a more rapid rH5-specific IgG antibody response (Week 4) (FIG. 8 Panel A) and higher "functional" HAI antibody responses at Week 6 (FIG. 8 Panel B) when compared to W805EC. In particular, the DODAC formulation stimulated a geometric mean HAI titer of 1:111 (7/8 animals ≥1:40) when compared to only 1:32 for $W_{80}5EC$ (4/8 animals ≥1:40). A cut-off for geometric mean titer (GMT) of ≥1:40 for HAI is accepted in the art as a correlate of protection against influenza. Thus, in one embodiment, the invention provides that immunogenic compositions containing emulsion formulated with a small polar head group and a dual chain hydrophobic component (e.g., DODAC) display significant efficacy for induction of functional and protective antibody responses when administered via injection (e.g., via intramuscular injection) whereas immunogenic compositions containing emulsion formulated with CPC (large polar head group and absence of dual chain hydrophobic component) fail to display significant efficacy when administered via injection (e.g., intramuscular route).

Figure 9A:
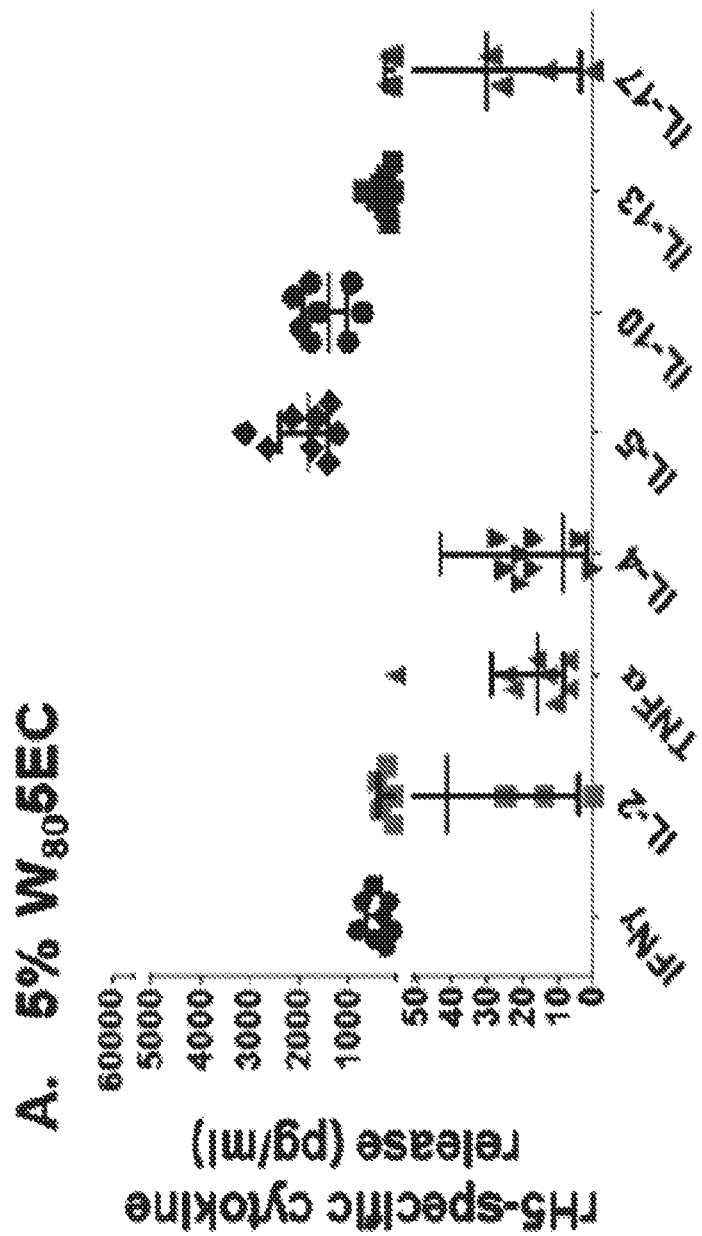
Figure 9B:
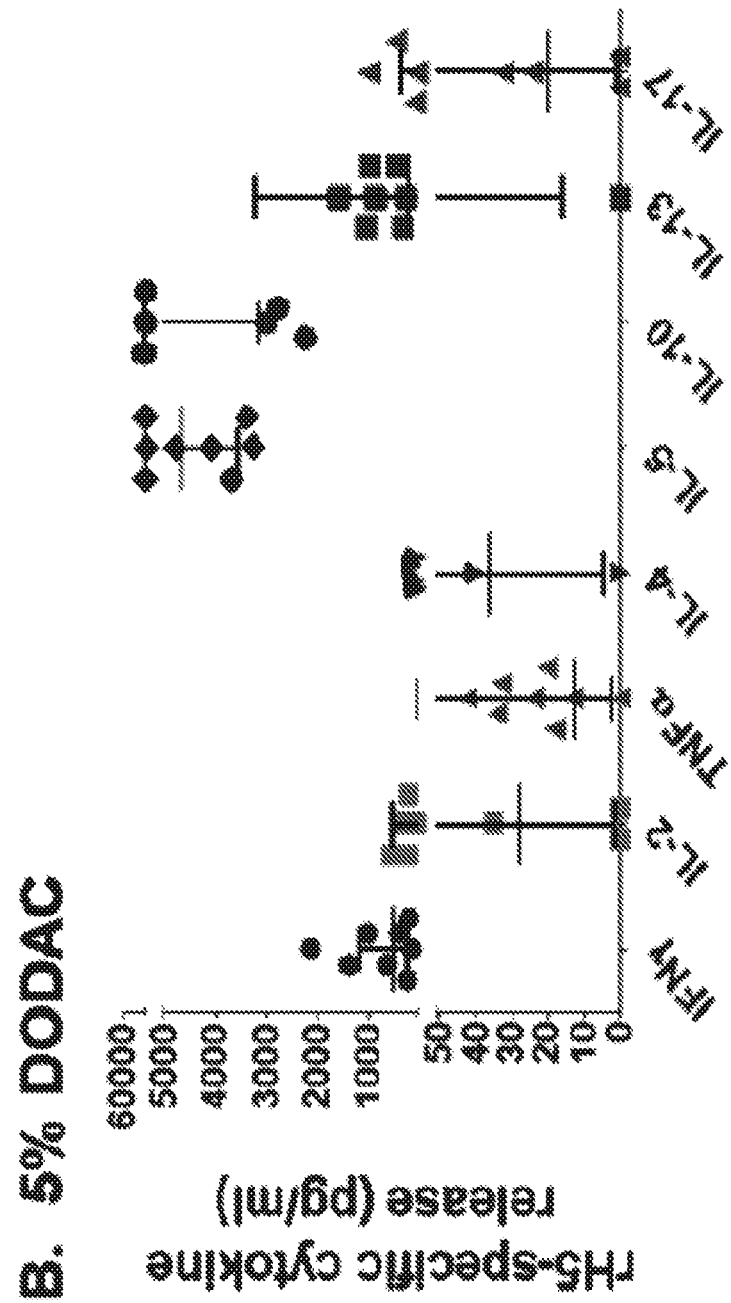
Figure 9C:
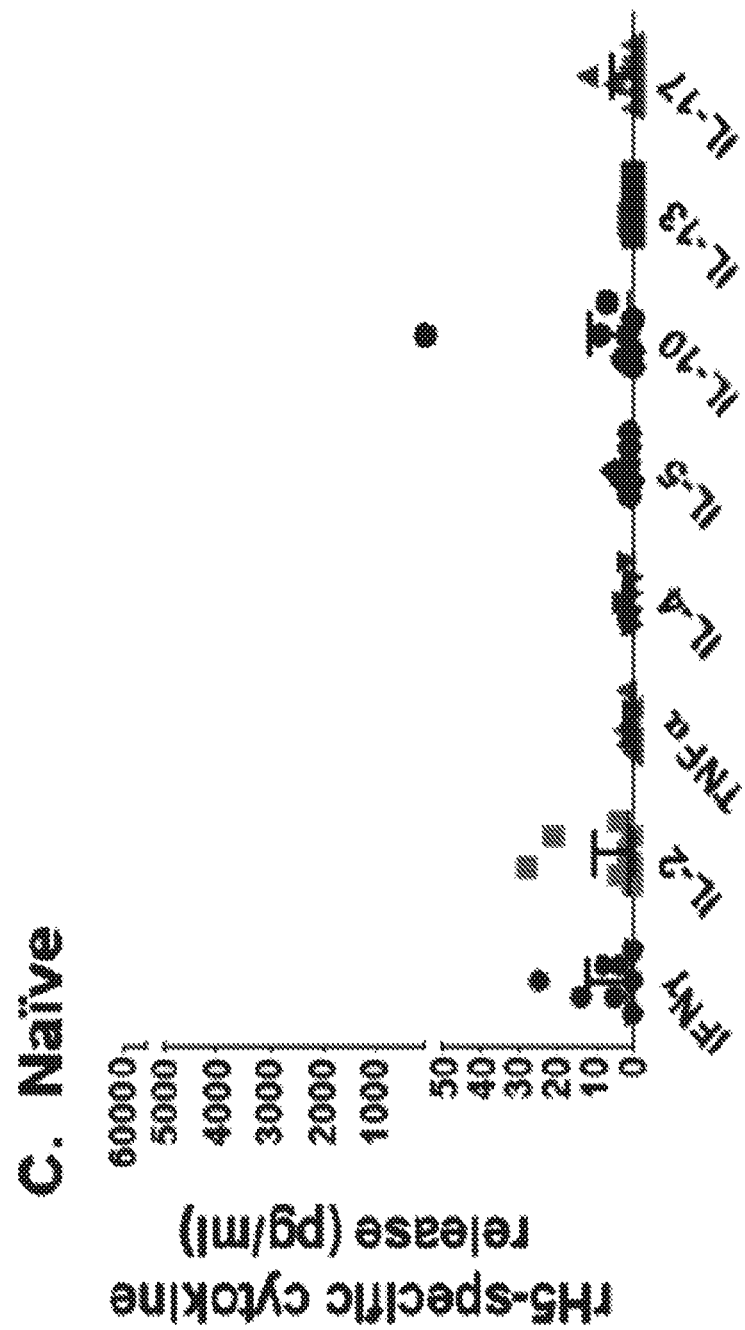

The profile of cell-mediated immunity (Th1, Th2, and Th17) as determined by cytokines secreted upon rH5 antigen re-stimulation of spleen cells obtained at the time of sacrifice on week 6 from mice immunized intramuscularly using these nanoemulsion-based pandemic influenza vaccines is shown in FIG. 9. Both DODAC and W805EC NE adjuvants stimulated balanced Th1 (IFNγ, IL-2) and Th2 (IL-4, IL-5, IL-13) responses with lower induction of Th17 (IL-17a) type responses. Surprisingly, DODAC formulation activated release of higher concentrations of IFNγ, IL-5 and IL-10 compared to W805EC. Thus, in one embodiment, the invention provides that immunogenic compositions containing emulsion formulated with a cationic lipid containing a polar head group and a dual chain hydrophobic component (e.g., DODAC) activate robust cell-mediated immunity together with enhanced production of functional antibody responses (e.g., compared to W805EC or other immunogenic compositions containing emulsion formulated with a large polar head groups and the absence of dual chain hydrophobic component that fail to activate same). Thus, the invention identifies and provides immunogenic compositions containing emulsion formulated with a cationic lipid containing a polar head group and a dual chain hydrophobic group as a significantly efficacious emulsion-based vaccine (e.g., formulated for injectable administration) against H5 pandemic influenza.

Example 4

Comparison of Intramuscular Administration of Immunogenic Compositions Containing Ovalbumin (OVA) and a Nanoemulsion Formulation Containing a Cationic Surfactant with Polar Head Group and Dual Chain Hydrophobic Component (e.g. DODAC) Versus an Immunogenic Compositions Containing OVA and Nanoemulsion Formulation Containing Large Polar Head Group and Absence of Dual Chain Hydrophobic Component Additional experiments were conducted during development of embodiments of the invention in order to further analyze and compare nanoemulsion adjuvant formulations containing a cationic lipid with a polar head group and dual chain hydrophobic component (e.g., DODAC) to other nanoemulsion adjuvant formulations (e.g., CPC) containing a large polar head group and/or lacking the dual chain hydrophobic component. Surprisingly, and as detailed below, intramuscular administration of immunogenic compositions containing a nanoemulsion formulated with DODAC with a polar head group and dual chain hydrophobic component (versus CPC containing a large polar head group and absence of the dual chain hydrophobic component) provided significantly improved adjuvant activity while at the same time displaying reduced tissue toxicity.

Materials and Methods

Preparation of Nanoemulsions. NE formulations were provided by NanoBio Corporation, Ann Arbor, MI Briefly, NEs were manufactured by high-speed emulsification of ionic and nonionic surfactants, ethanol (200 proof), soybean oil and purified water using a high speed homogenizer.

Animals. Pathogen-free, 8-week-old female C57BL/6 mice (Charles River Laboratories) were housed in specific pathogen-free conditions. All procedures were approved by the University Committee on the Use and Care of Animals (UCUCA) at the University of Michigan and were performed in accordance with these guidelines.

Figure 10:
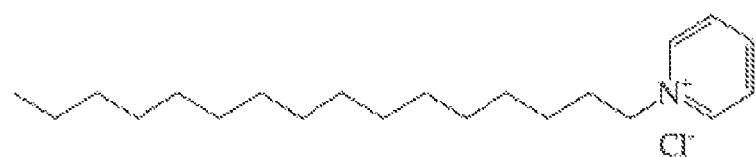
FIG. 10 shows the structure of cetyl pyridinium chloride (CPC) and the structure of dioctadecyl dimethyl ammonium chloride (DODAC).
Figure 10:
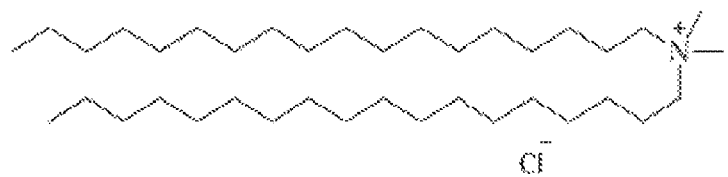

Vaccine Preparations for Immunization. For the intranasal (IN) immunization studies, mixtures of NE and ovalbumin (NE-OVA) at final concentrations of 20% NE (w/v) and 1.33 mg/mL OVA (endograde ovalbumin, Hyglos GmbH) in PBS, pH 7.4 were prepared. NE-OVA formulations were vortexed, and incubated for at least 15 min at RT prior to immunization. C57BL/6 mice were immunized via IN administration with 15 µl (7.5 µl/nare) of the NE-OVA mixture (20% NE and 20 µg OVA/mouse) or with OVA alone in PBS. NE formulations evaluated were W805EC and DODAC (See FIG. 10 for structural comparison).

For the intramuscular (IM) immunization studies, mixtures of NE and ovalbumin (NE-OVA) at final concentrations of 5% NE (w/v) and 0.4 mg/mL OVA (endograde ovalbumin, Hyglos GmbH) in PBS, pH 7.4 were prepared. NE-OVA formulations were vortexed, and incubated for at least 15 min at RT prior to immunization. C57BL/6 mice were immunized via IM administration with 50 µL of the NE-OVA mixture (5% NE and 20 µg OVA/mouse) or with OVA alone in PBS. NE formulations evaluated were W805EC and DODAC.

Immunization and Humoral Response. For humoral response immunization studies via IN administration, C57BL/6 mice were immunized with two IN administrations, 4 weeks apart, of 15 µL (7.5 µL per nare) of the NE-OVA mixture (20% NE and 20 µg OVA/mouse).

The IM administration, C57BL/6 mice were immunized with two IM administrations, 4 weeks apart, of 50 µL of the NE-OVA mixture (5% NE and 20 µg OVA/mouse).

Serum was obtained from the saphenous vein 2-weeks post immunization, and anti-OVA specific IgG end-titers were measured by ELISA. Briefly, serum samples were serially diluted in PBS with 0.1% BSA, and incubated on microtiter plates coated with 20 µg/mL OVA. ELISAs were developed with an alkaline phosphatase detection system, and quantified by measuring the optical density (OD) at 405 nm (OD405). Endpoint titers are reported as the reciprocal of the highest serum dilution giving an OD above a cutoff value (sum of OD of the same dilution of a control serum from an untreated mouse and two times the standard deviation).

Cellular Immune Response. Cellular response was evaluated at sacrifice (2 weeks post final boost) in splenocytes isolated as described above. Isolated splenocytes on 96-well plates were stimulated with 20 µg/mL ovalbumin (Hyglos, GmbH) in 100 µL of media for 48 h at 37° C. Cell supernatant was collected, and cytokine levels were assessed using a Milliplex MAP mouse cytokine/chemokine magnetic multiplex kit (Millipore) customized for IFN-γ, IL-5, IL-17 and IL-13 following the manufacturer's protocol.

Figure 11:
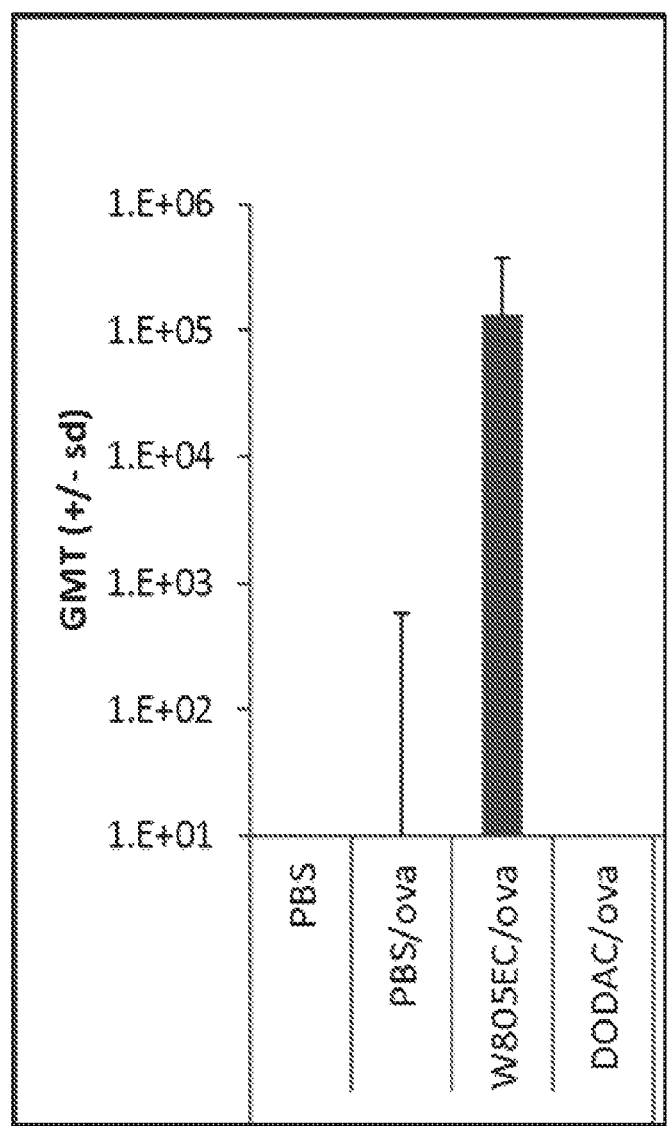
FIG. 11 shows OVA-specific IgG titers four weeks after second administration via (A) intranasal (IN) administration or (B) intramuscular (IM) administration of immunogenic compositions containing 5% W805EC or 5% DODAC compared to PBS and OVA controls.
Figure 12:
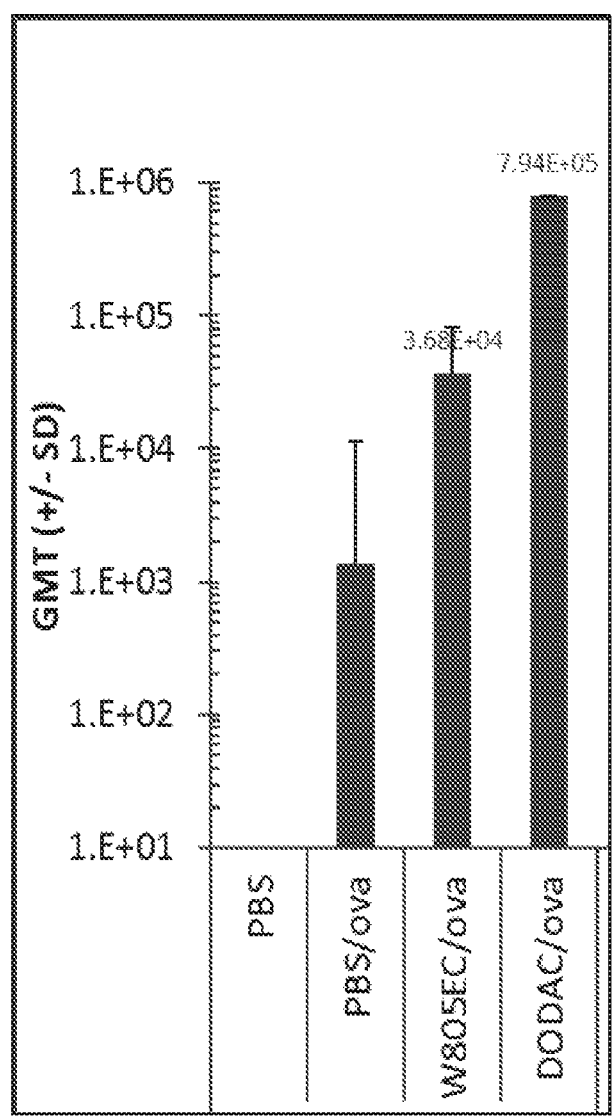
FIG. 12 shows IFN-γ production induced by (A) intranasal (IN) administration versus (B) intramuscular (IM) administration of immunogenic compositions containing 5% W805EC or 5% DODAC compared to controls.
Figure 12A:
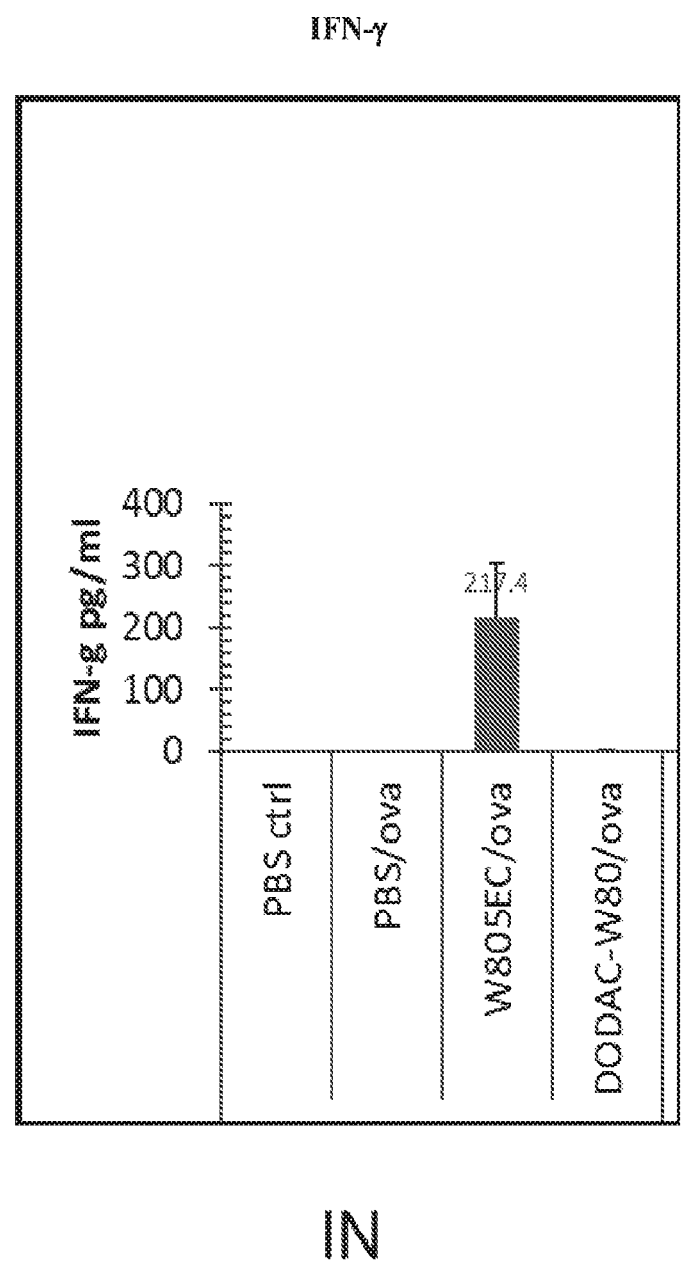
Figure 12B:
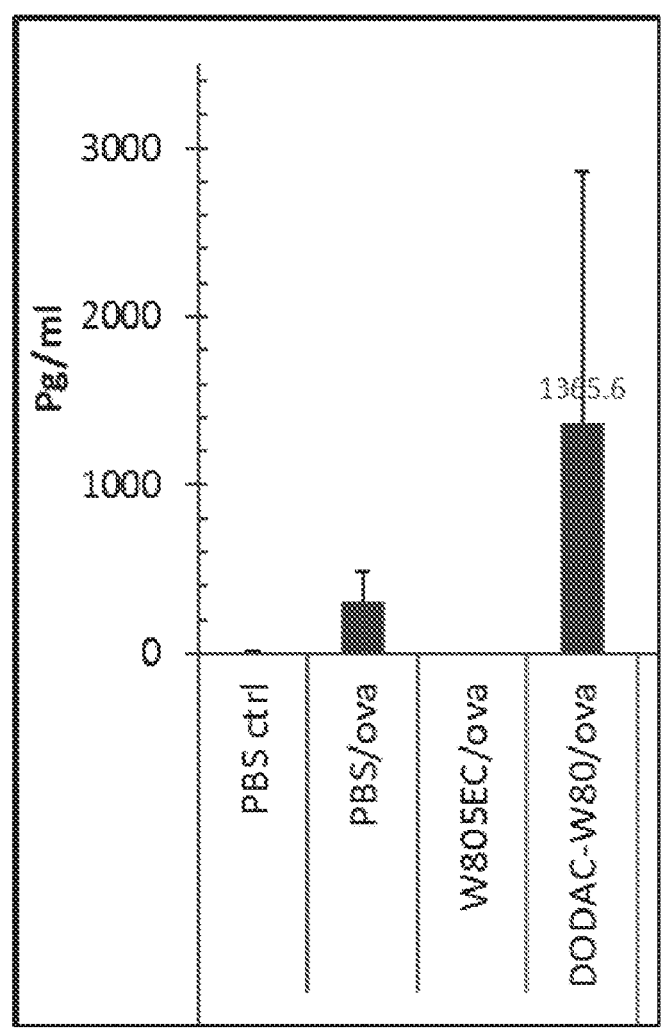
Figure 13A:
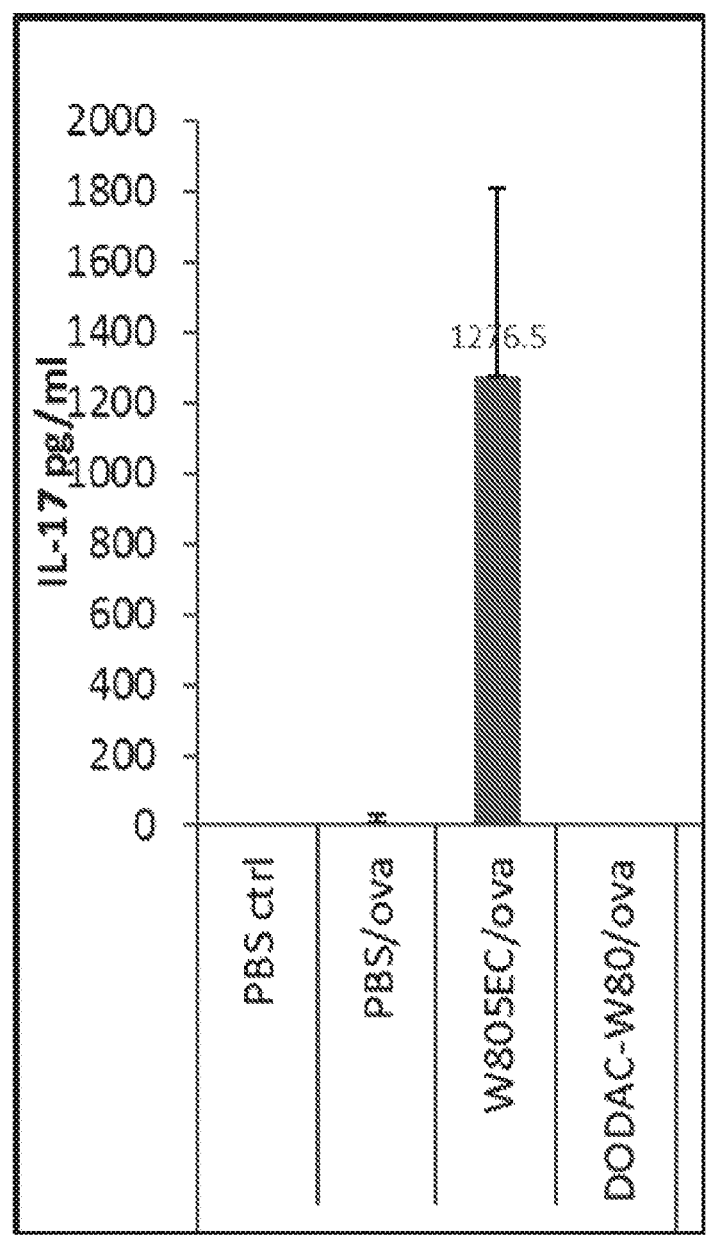
FIG. 13 shows IL-17 production induced by (A) intranasal (IN) administration versus (B) intramuscular (IM) administration of immunogenic compositions containing 5% W805EC or 5% DODAC compared to controls.
Figure 13B:
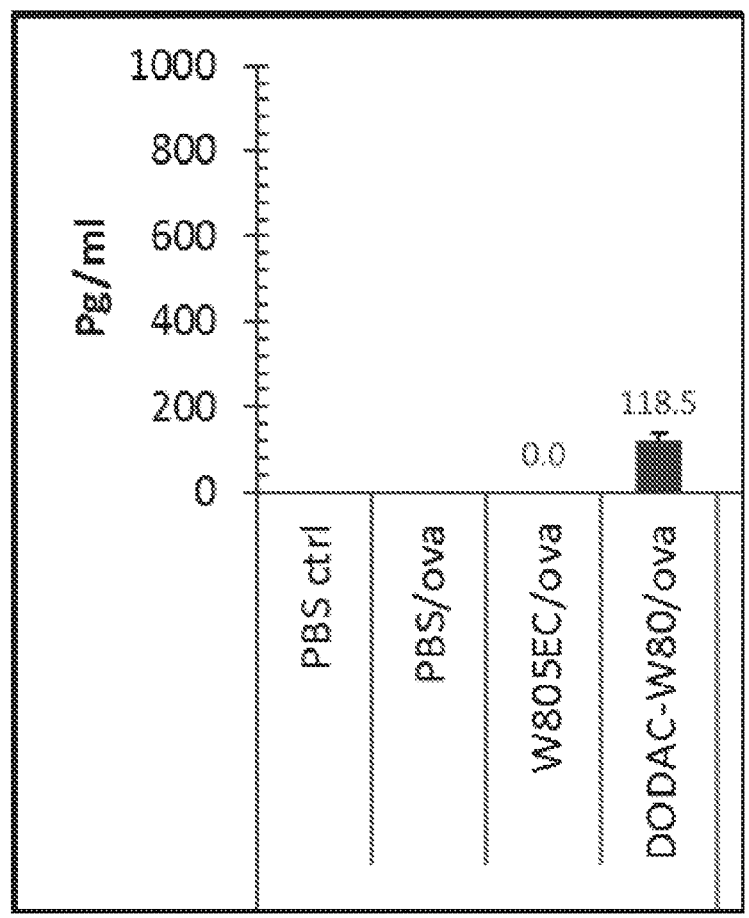
Figure 14A:
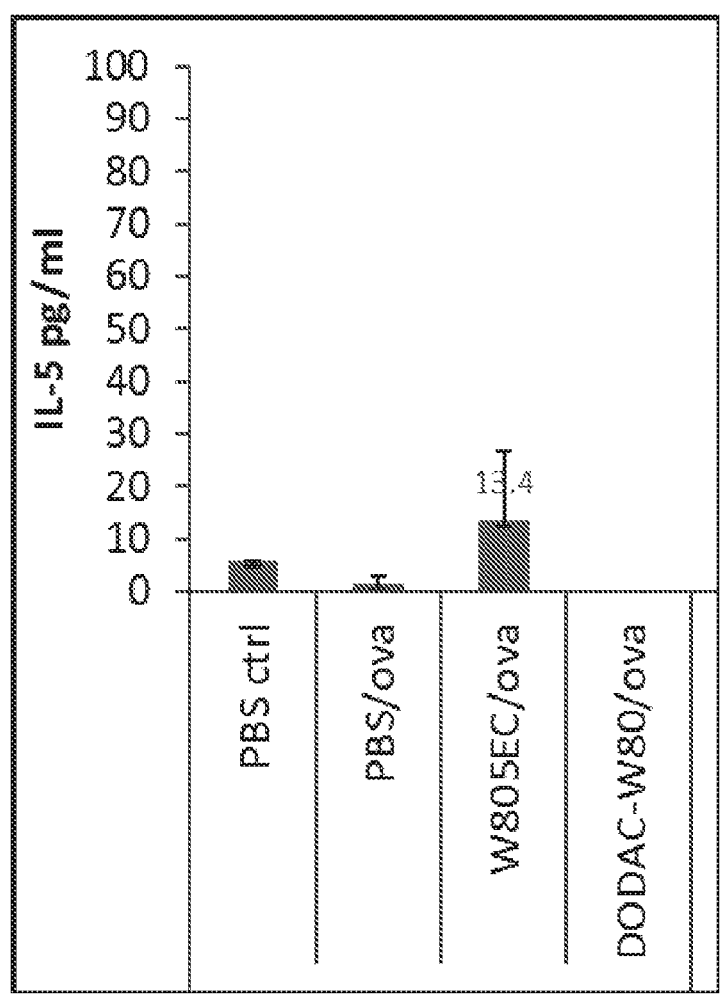
FIG. 14 shows IL-5 production induced by (A) intranasal (IN) administration versus (B) intramuscular (IM) administration of immunogenic compositions containing 5% W805EC or 5% DODAC compared to controls.
Figure 14B:
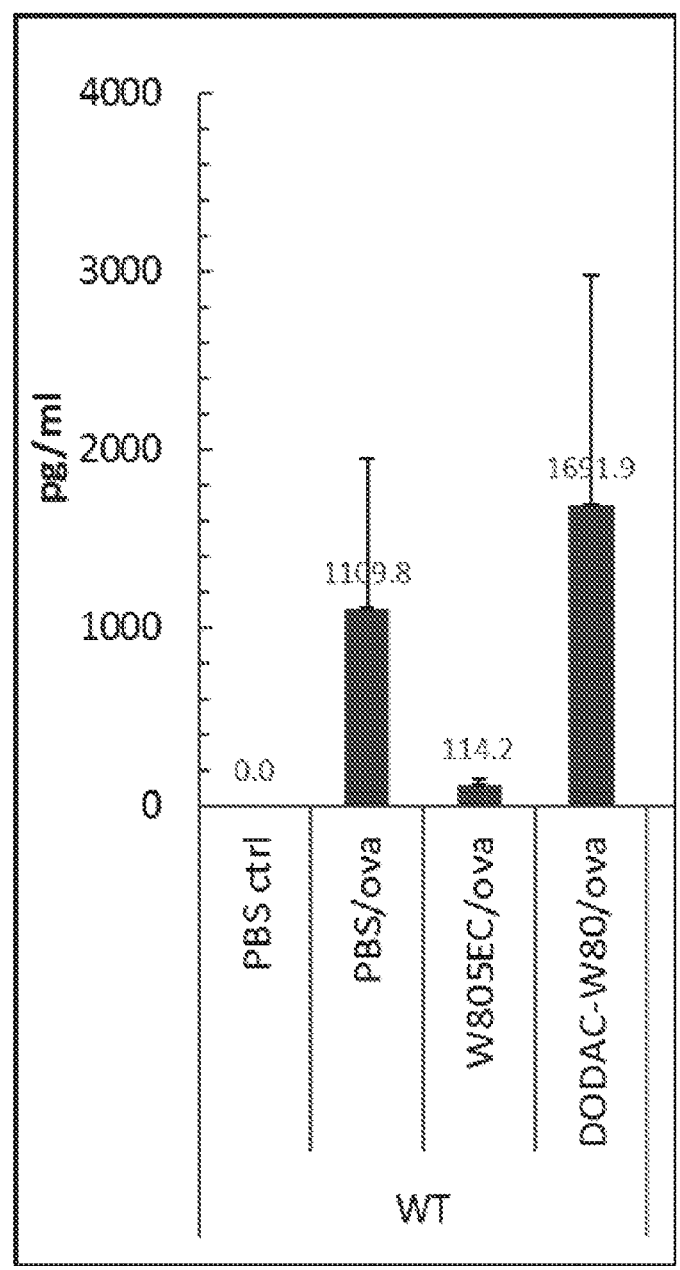
Figure 15A:
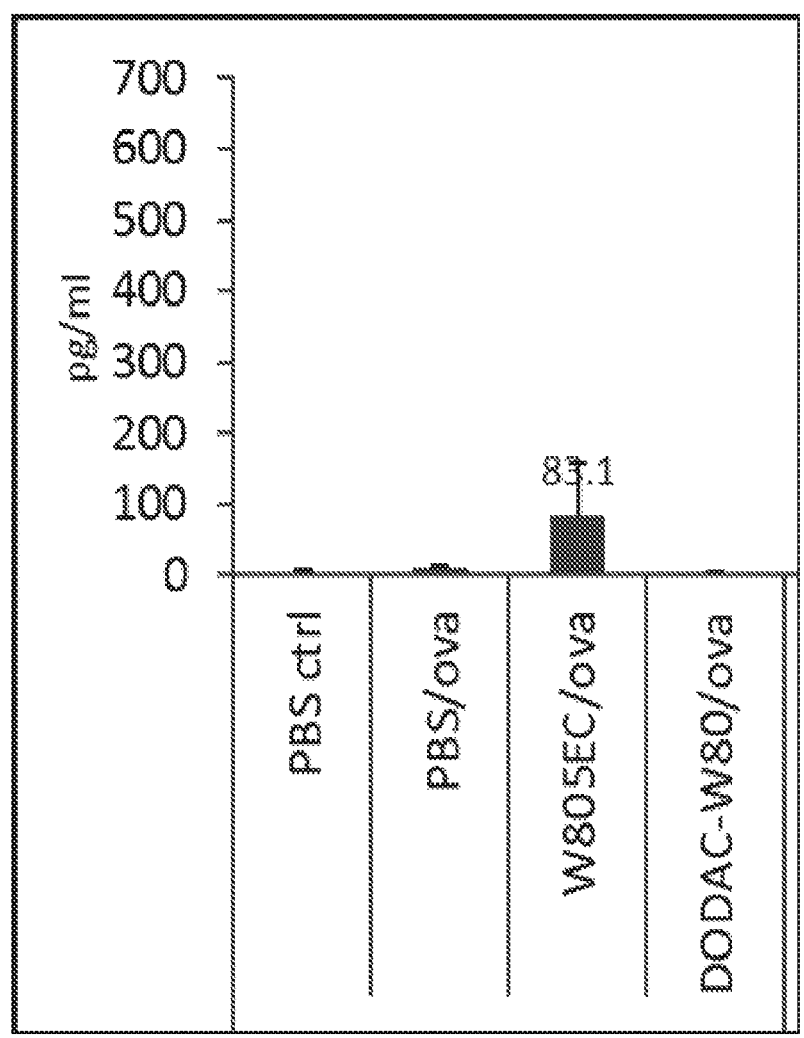
FIG. 15 shows IL-13 production induced by (A) intranasal (IN) administration versus (B) intramuscular (IM) administration of immunogenic compositions containing 5% W805EC or 5% DODAC compared to controls.
Figure 15B:
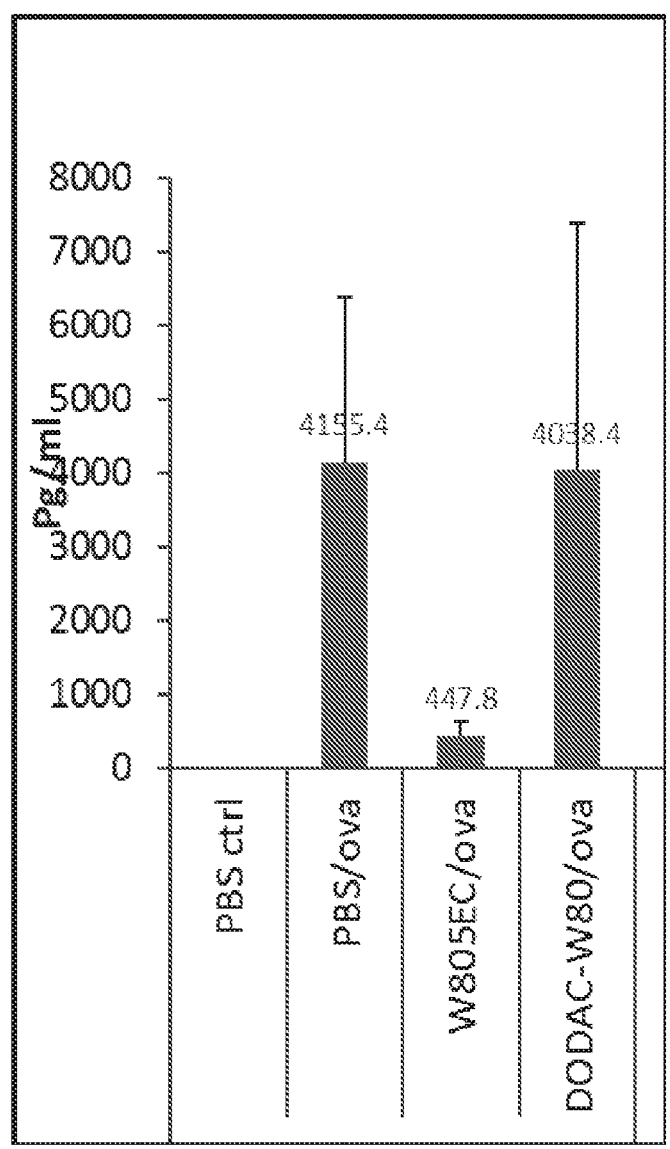

Sera from mice 4 weeks after 2nd immunization with NE adjuvanted OVA vaccine. Following intranasal vaccination, mice vaccinated with W805EC vaccine showed a high serum IgG, while mice vaccinated intranasally with DODAC adjuvant did not produce antibodies (See FIG. 11A). In sharp contrast, IM immunization with DODAC adjuvant resulted in a significantly higher IgG antibody titer compared with IM immunization with W805EC adjuvant (See FIG. 11B).

Mice were vaccinated IM or IN with NE/Ova vaccine as described above. Splenocytes were collected 2 weeks post $2^{nd}$ dose and tested for different cytokine production. As shown in FIGS. 12-15, IN immunization with W805EC resulted in balanced Th1 (INF-γ)/Th2 (IL-5 and IL-13)/Th17 (IL17) type responses. IM immunization with DODAC formulation also resulted in a balanced Th1 (INF-γ)/Th2 (IL-5 and IL-13)/Th17 (IL17) type responses. However, the IL-17 production in the case of IM DODAC immunization was at lower levels compared to the IL-17 production resulting from IN $W_{80}5EC$ immunization and the IL-5, 13 and INF-T was at significantly higher levels compared to the IN $W_{80}5EC$ immunization.

Thus, in one embodiment, the invention provides immunogenic compositions containing emulsion formulated with a cationic lipid containing a polar head group and a dual chain hydrophobic component (e.g., DODAC) display significant efficacy for induction of functional and protective antibody responses when administered via injection (e.g., intramuscular injection of DODAC containing immunogenic composition results in production of significantly higher levels of Th1 and Th2 cytokines and lower levels of IL17 compared to immunogenic compositions containing a surfactant lacking dual chain hydrophobic component (e.g., CPC)).

Example 5

Nanoemulsion Stability Testing

Experiments were conducted to test and assess various emulsion compositions of the invention. In particular, biophysical parameters including appearance, pH, particle size and zeta potential of emulsions were characterized after exposing the emulsion to various conditions.

Experimental design and autoclaving parameters. Nanoemulsions were autoclaved at 121° C. for 15 minutes. Table 5 compares the compositions of the nanoemulsions that were used analyzed.

TABLE 5

Comparison of the 60% Nanoemulsion Compositions

| Ingredients | 60% W805EC (% w/w) | 60% DODAC (% w/w) |
|---|---|---|
| Purified Water | 54.10 | 54.10 |
| Dehydrated Alcohol | 4.04 | 4.04 |
| Cetylpyridinium Chloride (CPC) | 0.64 | — |
| Dioctadecyldimethylammonium chloride (DODAC) | — | 0.64 |
| Polysorbate 80 (Tween 80) | 3.55 | 3.55 |
| Soybean Oil | 37.67 | 37.67 |
| Total | 100.00% | 100.00% |

Autoclaving of nanoemulsion adjuvants was performed a using cGMP-compliant steam sterilizer. Nanoemulsion adjuvant was filled into Schott vials (Type 1 glass, 50 mL, stopper+crimp seal) with a fill amount of 50 g of nanoemulsion. Determining the characteristics of nanoemulsion after autoclave process may enable terminal sterilization of the nanoemulsion adjuvant in a cGMP environment and validation of the process.

Test Methods and Passing Criteria for Stability Studies. Stability was assessed by monitoring changes in physical appearance (settling, creaming, color change, and phase separation) at various storage conditions (5° C., 25° C./60% RH, and 40° C./75% RH). In addition, cetylpyridinium chloride (CPC) potency, particle size, zeta potential and pH of the adjuvant were also measured. Reverse Phase High-Performance Liquid Chromatography (RP-HPLC) was used to measure the potency of cetylpyridinium chloride (% CPC label claim). Dynamic light scattering using the Malvern Zetasizer was used to determine particle size, particle size distribution and zeta potential.

The tests and criteria for assessment of long-term stability are listed in Table 6.

TABLE 6

Test Methods and Passing Criteria for Long Term Stability Studies

| TEST | METHOD | CRITERIA/Expected Target |
|---|---|---|
| Physical Appearance | Visual | White to off-white liquid; no phase separation; moderate creaming and settling is acceptable |
| CPC Potency | RP-HPLC | 90.0-110.0% of label claim (Target: 100%) |
| pH | pH meter | 4.0-6.0 (Target: 5.2) |
| Particle Size | Dynamic light scattering (Malvern Zetasizer) | Z-average is in range of 300-600 nm Polydispersity Index (PdI) (Target: Less than 0.22) PdI less than 0.22 indicate a unimodal distribution, PdI above 0.22 indicate a multimodal distribution. |
| Zeta Potential | Electrophoretic Light Scattering (Malvern Zeta Sizer) | Report results (Target: Greater than 30 mV) |

Physical Appearance Test Method. Observations of physical appearance were recorded according to the Universal Emulsion Stability Assessment (NBP-021 Rev: 4). Physical appearance was determined at the initial time point and at different time points under various storage conditions. The physical appearance observation was then recorded and evaluated using the acceptance criteria in Table 7.

TABLE 7

Stability Parameters, Description, and Acceptance Criteria

| Stability Parameter | Description | Acceptance Criteria |
|---|---|---|
| Color | A white to off-white liquid | A white to off-white liquid acceptable. Yellow (light to dark), tan, and shades of brown not acceptable. |
| Creaming | A white, creamy layer on top of the emulsion that is more opaque than the rest of the emulsion. Remixing will restore homogeneity. | Presence (+) or absence (−) All stages of creaming are acceptable |
| Settling | A gradual decrease in opacity of the emulsion from top to bottom. Remixing will restore homogeneity. | Mild - cloudiness gradient from top to bottom (no defining layers) Moderate - clear at bottom of vial with increasing opacity toward the cap Severe - 3-4 distinct layers Extreme - only 2 layers All stages of settling are acceptable |
| Phase Separation | Separation of the oil and water phases of the emulsion. Remixing will not restore homogeneity. | Pass: None Insignificant - a few droplets are visible at surface Mild - few visible oil droplets / Fail: Moderate - a film of oil Severe - 3 distinct layers Extreme - total separation into 2 phases (oil and water) | pH assessment. The pH was determined using a standard pH meter using with the appropriate probe and pH standards.

Cetylpyridinium Chloride % Label Claim by Reverse Phase High Pressure Liquid Chromatography (RP-HPLC) Test Method. The HPLC method was developed for the 60% nanoemulsion adjuvant. Samples were analyzed using the RP-HPLC method described below in Table 8.

TABLE 8

| Chromatographic Conditions | |
|---|---|
| HPLC System | Shimadzu HPLC System: Liquid Chromatograph Model# LC-20AT System Controlled Model# CBM-20A Degasser Model# DGU-20A, Autosampler Model# SIL-20ACHT, UV-VIS Detector Model# SPD-20AV Column Oven Model# CTO-20AC |
| HPLC Column | Waters Symmetry, C-18, 5 μm particle size, 3.9 mm diameter × 150 mm length |
| Mobile Phase | 35% Buffer (CTAB-$KH_2PO_4$) Solution: 65% Methanol (v/v) (pH 2.5) |
| Chromatograph | Isocratic method |
| Detection Wavelength | 260 nm |
| Flow Rate | 1 mL/min |
| Column Temperature | 30° C. |
| Injection Volume | 100 μL |
| Run Time | 30 minutes |
| CPC Standard: | 50 μg/mL (Source: USP) One-point standard calibration curve |
| Data Acquisition | Acquisition Channel I |
| Bracketing Standard | 50 μg/mL |

Particle Size Analysis Polydispersity Index (PdI) and Zeta Potential. The mean particle size (Z-AVE), polydispersity index (PdI) and zeta potential were determined for all the stability samples by dynamic light scattering using photon correlation spectroscopy in a Malvern Zetasizer Nano ZS90 (Malvern Instruments, Worcestershire, UK). All measurements were carried out at 25° C. after appropriate dilution with double distilled 0.22 μm filtered water.

Viscosity Method. The method uses a Brookfield Viscometer Models LV, DVII Pro or LVDV-IIIU (Brookfield Engineering Laboratories, Inc., USA). Prior to taking the viscosity reading, allow both viscometer and test sample to come to 22.0-25.0° C. The sample was placed in a BD Falcon™ 50 mL Conical Centrifuge Tube or a suitable tall glass container wide enough to properly cover the spindle. The container containing the test sample was placed under the spindle and centered. Spindle coded LV2 (62) was than lowered into the sample container to the immersion line that is etched on the spindle. The viscosity of the sample was measured at a speed of 60 RPM. The viscosity (cP) reading and the torque (%) were recorded. For an acceptable viscosity measurement, the torque % should be greater than 10% and less than 80%.

Results: Stability of $W_{80}5EC$ Adjuvant after autoclaving at 121° C. for 15 minutes After filling, the 60% $W_{80}5EC$ nanoemulsion adjuvant vials but before autoclaving the vials were tested for homogeneity. The filling process resulted in homogeneous filled vials as shown in Table 9.

TABLE 9

| Filling Product Homogeneity of 60% $W_{80}5EC$. | | | |
|---|---|---|---|
| Sample ID or Sampling Area | pH (4-6) | Mean Particle Size (Z-AVE) (300-600 nm) | PdI (≤0.22) |
| Final Product | 5.09 | 463.8 ± 10.7 | 0.129 ± 0.013 |
| Filling of Product | | | |
| BEGINNING OF FILL | 5.07 | 464.7 ± 1.3 | 0.123 ± 0.012 |
| MIDDLE OF FILL | 5.06 | 458.8 ± 6.1 | 0.114 ± 0.005 |
| END OF FILL | 5.07 | 476.0 ± 1.4 | 0.160 ± 0.009 |

After autoclaving, the vials were allowed to cool at room temperature for 24 hours for the initial analysis.

A summary of stability data for nanoemulsion Lot (60% $W_{80}5EC$) comparing non-autoclaved (NA) and autoclaved (A) formulations (121° C. for 15 minutes) at T=0 through 6 months storage at 5° C., 25° C. or 40° C. in Table 11. pH after storage over 6 months at 5° C., 25° C. or 40° C. and 12 months storage at 5° C. and 25° C. are shown in FIG. 2. Data for mean particle size (Z-average) are summarized graphically in FIG. 17.

There was no significant difference when comparing autoclaved vs. non-autoclaved nanoemulsion formulations in the percent CPC label claim, pH, or mean particle size (Z-average) for the 60% $W_{80}5EC$ formulations stored at various temperatures for 6 months. No change in the mean particle size (Z-average) or % CPC label claim was detected. The autoclaved particle size profile overlays showed no signs of instability. Thus, in one embodiment, the invention provides that $W_{80}5EC$ adjuvant is stable after autoclaving at 121° C. for 15 minutes after storage at 40° C. for at least six months as determined by evaluation of biophysical parameters including pH, mean particle size (Z-average), PdI and CPC content.

TABLE 10

| 60% $W_{80}5EC$: Non-Autoclaved vs Autoclaved | | | | | | | | | |
|---|---|---|---|---|---|---|---|---|---|
| Lot # | Time Point | Storage Condition | Appearance | pH | % CPC | Particle Size (nm) | PdI | Zeta (mV) | Viscosity cP (% Torque) |
| Group 0: Non-Autoclaved | | | | | | | | | |
| Group 0 | 0 | Initial | Pass | 5.07 | 97.0 | 476.0 ± 1.5 | 0.160 ± 0.009 | 44.2 ± 2.0 | 128.0 (25.6%) |
| Group 0 | 1 month | 5° C. | Pass | 5.10 | 99.1 | 464.0 ± 5.2 | 0.133 ± 0.019 | 46.7 ± 1.7 | 123.5 (24.7%) |
| | | 25° C. | Pass | 5.07 | 98.4 | 479.0 ± 10.9 | 0.126 ± 0.053 | 58.6 ± 1.8 | 125.5 (25.1%) |
| | | 40° C./75% RH | Pass | 5.04 | 98.8 | 476.4 ± 4.8 | 0.154 ± 0.044 | 43.2 ± 0.6 | 127.5 (25.5%) |
| Group 0 | 3 months | 5° C. | Pass | 5.09 | 99.1 | 464.5 ± 2.3 | 0.171 ± 0.034 | 54.3 ± 0.8 | 124.0 (24.8%) |
| | | 25° C. | Pass | 5.05 | 98.6 | 465.0 ± 1.2 | 0.130 ± 0.023 | 58.0 ± 0.7 | 125.0 (25.0%) |
| | | 40° C./75% RH | Pass | 4.99 | 98.6 | 466.6 ± 2.7 | 0.107 ± 0.029 | 55.8 ± 0.8 | 122.0 (25.4%) |

TABLE 10-continued

| | | | 60% W$_{80}$5EC: Non-Autoclaved vs Autoclaved | | | | | | | |
|---|---|---|---|---|---|---|---|---|---|---|
| Lot # | Time Point | Storage Condition | Appearance | pH | % CPC | Particle Size (nm) | PdI | Zeta (mV) | Viscosity cP (% Torque) |
| Group 0 | 6 months | 5° C. | Pass | 5.07 | 98.3 | 468.2 ± 4.6 | 0.145 ± 0.025 | 56.5 ± 0.6 | 123.5 (24.7%) |
| | | 25° C. | Pass | 5.05 | 98.4 | 459.9 ± 3.2 | 0.117 ± 0.049 | 54.7 ± 0.8 | 125.0 (25.0%) |
| | | 40° C./75% RH | N/A | — | — | — | — | — | — |
| | | | Group 1: Autoclaved: 121° C. for 15 minutes | | | | | | |
| Group 1 | 0 | Initial | Pass | 4.98 | 96.8 | 473.1 ± 6.2 | 0.132 ± 0.018 | 41.5 ± 0.6 | 125.5 (25.1%) |
| Group 1 | 1 month | 5° C. | Pass | 4.94 | 98.4 | 471.1 ± 3.5 | 0.103 ± 0.034 | 51.6 ± 1.2 | 122.0 (24.4%) |
| | | 25° C. | Pass | 5.03 | 98.9 | 467.5 ± 8.6 | 0.136 ± 0.007 | 54.9 ± 1.0 | 125.0 (25.0%) |
| | | 40° C./75% RH | Pass | 4.94 | 98.4 | 472.3 ± 7.9 | 0.130 ± 0.014 | 45.7 ± 0.3 | 125.0 (25.0%) |
| Group 1 | 3 months | 5° C. | Pass | 5.00 | 98.4 | 469.5 ± 5.2 | 0.143 ± 0.030 | 51.9 ± 0.8 | 124.0 (24.8%) |
| | | 25° C. | Pass | 4.98 | 98.8 | 465.5 ± 5.6 | 0.101 ± 0.023 | 48.0 ± 0.8 | 125.0 (25.0%) |
| | | 40° C./75% RH | Pass | 4.89 | 99.3 | 466.7 ± 7.9 | 0.125 ± 0.003 | 53.4 ± 0.3 | 121.5 (24.3%) |
| Group 1 | 6 months | 5° C. | Pass | 5.07 | 98.3 | 454.9 ± 4.2 | 0.150 ± 0.010 | 54.4 ± 1.5 | 122.0 (24.5%) |
| | | 25° C. | Pass | 5.02 | 98.1 | 456.7 ± 5.6 | 0.118 ± 0.033 | 50.8 ± 0.6 | 125.0 (25.0%) |
| | | 40° C./75% RH | Pass | 4.82 | 97.4 | 460.2 ± 4.9 | 0.146 ± 0.025 | 51.2 ± 1.5 | 126.0 (25.2%) |

Results: Stability of 60% DODAC formulation after autoclaving at 121° C. for 15 minutes The data for the 60% DODAC nanoemulsion before and after autoclaving is shown in Table 11. Data for pH, mean particle size (Z-average) and % CPC (label claim) are summarized graphically.

There was no significant change when comparing the initial pH to the final pH after autoclaving under any of the conditions. A change of more than one pH units is considered significant. Similarly, there were no observed changes in the particle size profile before and after autoclaving the formulations (See FIG. 18). Therefore, the present invention provides that autoclaving is a feasible sterilization means.

TABLE 11

Summary of Control Samples Before and After Autoclaving 60% DODAC Formulations

| Condition | Appearance | pH | Mean Particle Size (nm) | Polydispersity Index | Zeta Potential |
|---|---|---|---|---|---|
| No Autoclaving (Control) | Pass | 5.22 | 441.3 ± 6.7 | 0.143 ± 0.017 | 53.7 ± 0.5 |
| Autoclaved at 121° C. × 15 min | Pass | 5.06 | 440.3 ± 1.9 | 0.133 ± 0.022 | 56.5 ± 0.6 |

Thus, in one embodiment the invention provides that autoclaving emulsions at 121° C. for 15 minutes is a viable option for sterilization based on the stability studies of physical appearance, CPC content, pH, particle size analysis, polydispersity and viscosity. Autoclaving at 121 C for 15 minutes is not an intuitive or standard options for sterilization of emulsion. Autoclaving of emulsions typically leads to instability of the droplets leading to larger mean particle size and an unstable product.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. An immunogenic composition formulated for administration via injection comprising:
   an oil in water emulsion comprising dioctadecyldimethylammonium chloride (DODAC), a non-ionic surfactant, an organic solvent, oil, and water, wherein the surfactant blend ratio of DODAC to non-ionic surfactant is 1:6, and
   an antigen;
   wherein the antigen is an inactivated microbial pathogen, an isolated protein from a microbial pathogen, and/or a recombinant protein from a microbial pathogen; and
   wherein the immunogenic composition produces a cell mediated immune response comprising elevated levels of IFN-γ and detectable, antigen-specific neutralizing antibody titers when administered via injection and fails to produce a cell mediated immune response comprising elevated levels of IFN-γ and detectable, antigen-specific neutralizing antibody titers when administered intranasally via the nasal mucosa.

2. The immunogenic composition formulated for administration via injection of claim 1, wherein the nonionic surfactant is selected from ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis(imidazoyl carbonyl)), nonoxynol-9, Bis(polyethylene glycol bis(imidazoyl carbonyl)), Brij 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O-(N-heptylcarbamoyl)-alpha-D-glucopyranoside, Nonaethylene glycol monododecyl ether, N-Nonanoyl- N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, a poloxamer, semi-synthetic derivatives thereof, or combinations thereof.

3. The immunogenic composition formulated for administration via injection of claim 1, wherein the oil in water emulsion is physically stable after autoclaving at 121° C. for 15 minutes.

4. A pharmaceutical composition comprising the immunogenic composition formulated for administration via injection of claim 1.

5. A vaccine comprising the immunogenic composition formulated for administration via injection of claim 1.

6. A syringe comprising the immunogenic composition formulated for administration via injection of claim 1.

* * * * *